US012696897B2

(12) United States Patent
Forbes et al.

(10) Patent No.: US 12,696,897 B2
(45) Date of Patent: Aug. 4, 2026

(54) CRYOPRESERVING MACROPHAGES

(71) Applicant: The University Court of The University of Edinburgh, Edinburgh (GB)

(72) Inventors: Stuart Forbes, Edinburgh (GB); Lara Campana, Edinburgh (GB); Benjamin Dwyer, Edinburgh (GB); John Campbell, Edinburgh (GB); Alasdair Fraser, Edinburgh (GB)

(73) Assignee: The University Court of The University of Edinburgh, Edinburgh (GB)

( * ) Notice: Subject to any disclaimer, the term of this patent is extended or adjusted under 35 U.S.C. 154(b) by 565 days.

(21) Appl. No.: 17/927,788

(22) PCT Filed: May 27, 2021

(86) PCT No.: PCT/GB2021/051304
§ 371 (c)(1),
(2) Date: Nov. 25, 2022

(87) PCT Pub. No.: WO2021/240169
PCT Pub. Date: Dec. 2, 2021

(65) Prior Publication Data
US 2023/0210105 A1      Jul. 6, 2023

(30) Foreign Application Priority Data
May 27, 2020    (GB) .................................... 2007905

(51) Int. Cl.
*A01N 1/162* (2025.01)
*A61K 35/15* (2015.01)
*A61P 1/16* (2006.01)

(52) U.S. Cl.
CPC .............. *A01N 1/162* (2025.01); *A61K 35/15* (2013.01); *A61P 1/16* (2018.01)

(58) Field of Classification Search
CPC ..................................................... A01N 1/162
See application file for complete search history.

(56) References Cited

U.S. PATENT DOCUMENTS

2011/0206776 A1    8/2011  Tom et al.
2018/0092348 A1*  4/2018  She ...................... C12N 5/0693

FOREIGN PATENT DOCUMENTS

CN          108990965 A       12/2018
WO       WO-9302205 A1 *    2/1993     ............. C07K 14/52
WO       WO-9735472 A1 *   10/1997    ............. A01N 1/125
WO          2015027354 A2     3/2015
WO       WO-2018051136 A1 *  3/2018    ........... C12N 5/0606
WO          2018170188 A2     9/2018

OTHER PUBLICATIONS

PCT International Search Report, mailed Sep. 9, 2021, in connection with International Application No. PCT/GB2021/051304, all pages.
PCT Written Opinion, mailed Sep. 9, 2021, in connection with International Application No. PCT/GB2021/051304, all pages.
Great Britain Search Report issued Nov. 24, 2020 in connection with Great Britain Application No. GB2007905.9, 2 pages.
Jin et al., "Culture of Macrophage Colony-stimulating Factor Differentiated Human Monocyte-derived Macrophages," J. Vis. Exp. (2016) 112:e54244, pp. 1-6.

* cited by examiner

*Primary Examiner* — Qiuwen Mi
(74) *Attorney, Agent, or Firm* — Morrison & Foerster LLP

(57) ABSTRACT

The present invention relates to a method of improving the viability of macrophages subjected to cryopreservation, particularly for macrophages which are to be used in therapy, wherein the method comprises a step of maintaining the macrophages at a temperature of 2-12° C. for at least 30 minutes during either freezing or thawing procedures. Following the holding step during cooling, a cooling rate of 1 to 5° C. is used until the macrophages in a medium are frozen. For thawing the macrophages, a warming rate of 1 to 5° C. per minute is used until a temperature of 35-37° C. is reached. The present invention further relates to the cryopreserved macrophages, and the thawed macrophages produced by such methods. The technique may provide macrophages that are GMP-compliant and have a viability of at least 60%.

17 Claims, 23 Drawing Sheets

CRYOPRESERVING MACROPHAGES

CROSS-REFERENCE TO RELATED APPLICATIONS

Figure 1:
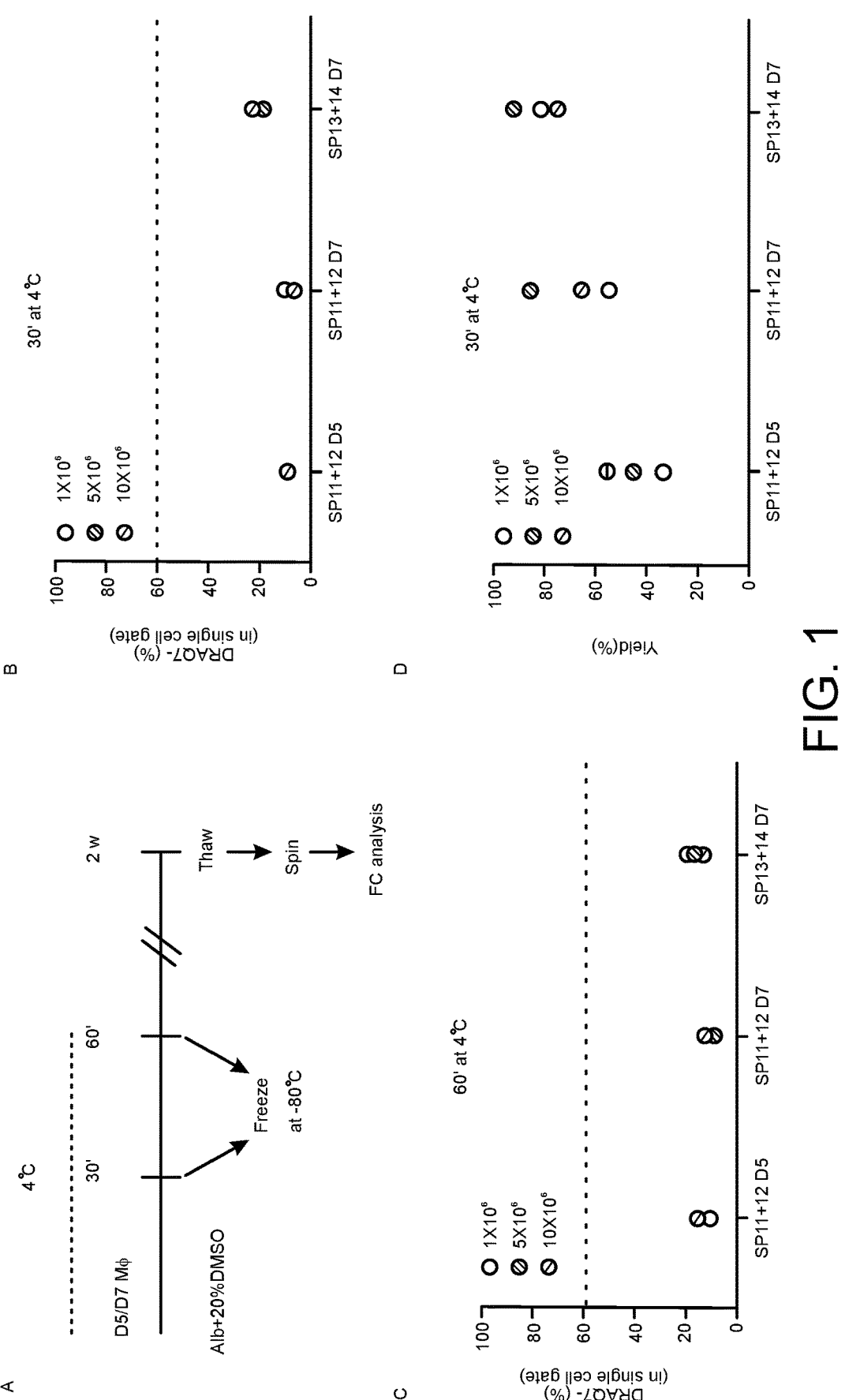
Figure 1:
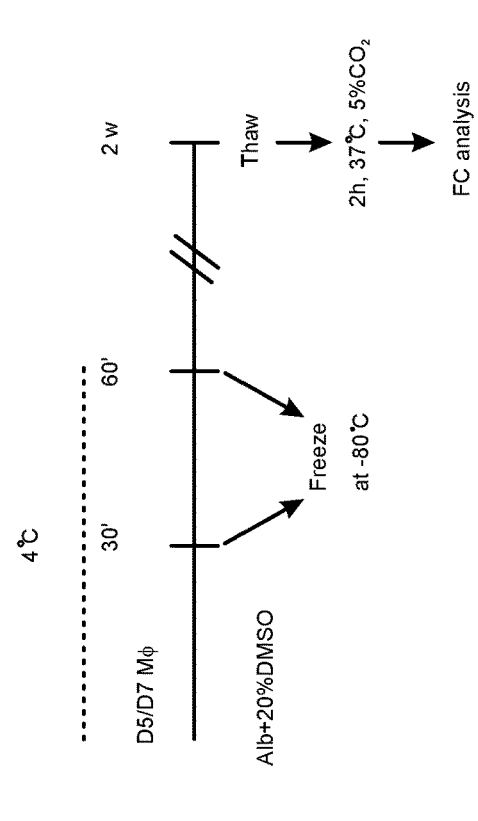
Figure 1:
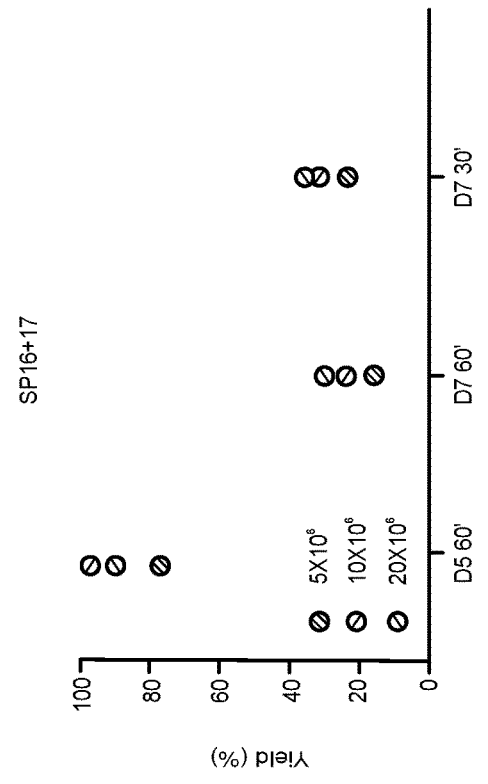
Figure 1:
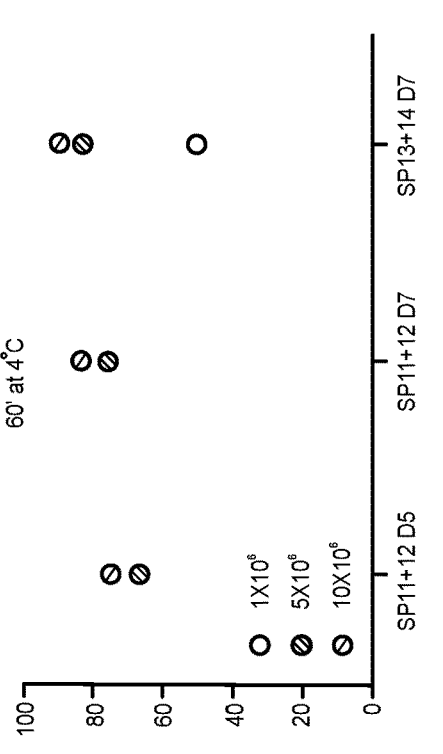

This application is a national stage entry of PCT International Application No. PCT/GB2021/051304, filed May 27, 2021, which claims benefit of priority to GB Application No. 2007905.9, filed May 27, 2020, which are incorporated herein by reference in their entireties.

TECHNICAL FIELD

The present invention relates to a method of cryopreserving macrophages, a method of thawing cryopreserved macrophages, and a combined method of cryopreserving and thawing macrophages. The present invention further relates to the cryopreserved macrophages, and the thawed macrophages produced by such methods.

BACKGROUND

One of the most important features of a cell therapy product is the possibility to be cryopreserved, shipped and efficiently thawed at the point of care. Products which do not satisfy these criteria are not commercially viable. Macrophages have proven efficacious as a potential cell therapy in a number of pre-clinical models of various human diseases (1-11). However, human macrophages have historically been difficult to cryopreserve. Instead, a variety of precursors have been cryopreserved, including monocytes, bone marrow and umbilical cord stem cells, and provided to laboratories for differentiation into macrophages on site immediately prior to therapy (12-17). However, this requires laboratory facilities to be available nearby the site of treatment and means that the macrophages cannot be stored for later use.

The standard procedure for cryopreservation is to freeze cells slowly until they reach a temperature below −70° C. in medium that includes a cryoprotectant. Vials are transferred to a liquid-nitrogen freezer to maintain them at temperatures below −130° C. The recovery of cryopreserved cells is straightforward: Cells are thawed rapidly in a water bath at 37° C., removed from the freeze-medium by gentle centrifugation and/or diluted with growth medium. However, these routine methods applied to other cells have not be found to have applicability to macrophages.

Some attempts at directly freezing human liver resident macrophages (Kupffer Cells) in non-GMP compliant conditions have been undertaken. However, the thawed product has only been used for functional in vitro assays and not for cell therapy (18).

Macrophages are highly sensitive to cryo-injury and others in this field have had difficulty with obtaining good survival of viable macrophages after cryopreservation and thawing.

When considering the use of cryopreserved macrophages as direct therapies to treat acute conditions, precursor cells are not a viable option, and a GMP-compliant protocol must be used to ensure safety. Many cryopreservation protocols require the use of agents such as bovine serum albumin to increase post freeze survival, which is not suitable for a GMP compliant protocol.

There are some companies commercialising frozen human macrophages, such as PromoCell. However, these macrophages are poorly characterised, and the viability post-thaw is only around 60%. Such a viability is not ideal for use in a clinical setting. Moreover, these cells require liquid nitrogen for storage, which is expensive and impractical in many treatment settings. Furthermore, such cells are sold for in vitro research use only and are not suitable for clinical procedures, indicating a non-GMP compliant medium is likely used.

In order to address one or more of the above-mentioned problems in the art, the present inventors have developed a novel method of cryopreserving and thawing macrophages. The method of the invention has a good yield, and the cells are well preserved with higher viability than that obtained with previous methods. Furthermore, the method is GMP-compliant and capable of being conducted in a sterile environment.

Good manufacturing practice (GMP) quality, defined by both the European Medicines Agency (EMA) and the Food and Drug Administration (FDA), is a requirement for clinical-grade cells, offering optimal defined quality and safety in cell therapy. Using animal component-free culture media and compliant cryopreservation procedures, immune reactions against animal proteins and infection risk caused by animal microbes can be avoided. In the development of cell therapies, compliant procedures must be developed to ensure the safe preparation and storage of cells prior to administration to a patient in need thereof.

It is also desirable to be able to freeze macrophages from different sources. For example, the macrophages may be simply isolated from blood, or derived from monocytes/progenitor cells or pluripotent stem cells. In some instances, the cells may be derived from a patient in need of therapy with macrophages, and either macrophages or monocytes, or other progenitor cells may be isolated from a patient. Some of these cells may be more sensitive to cryo-injury than others.

Further, the step of thawing the cryopreserved cells is a critical step in which many of the cells preserved by freezing may be lost due to cell rupture and the like. Common techniques for cell thawing include placing the frozen cells (in a suitable container) in a warm water bath to thaw the cells as rapidly as possible.

One or more aspects of the invention are directed towards solving one or more of the above-mentioned problems.

STATEMENTS OF INVENTION

The present invention relates to a novel method for cryopreserving macrophages. The present invention furthermore relates to a novel method for thawing cryopreserved macrophages. The present invention may also relate to a combined method of cryopreserving, storing and then thawing macrophages. The advantages shown by the present inventors include demonstrating good survival of the cryopreserved macrophages (such as over 60% of cells) with good viability (such as over 60% of surviving macrophages being viable). The inventors have shown that the technique may provide macrophage viability of at least 70%.

The macrophages stored via cryopreservation and subsequent thawing have been shown here to retain desirable characteristics, and may therefore be used therapeutically. The thawed macrophages may be used without further culturing techniques, or may be subjected to further culturing techniques, for example to polarise the cells into an M1 or M2 type, or to a type along this continuum. The thawed macrophages or polarised macrophages derived therefrom may be administered to a patient in need thereof.

According to a main aspect of the invention, there is provided a method of improving the viability of macrophages subjected to cryopreservation, wherein said method comprises the following steps during freezing and/or thawing of the macrophages:

i) Bringing the macrophages in a medium to a temperature of 2-12° C., and maintaining this temperature for at least 30 minutes; followed by either:

ii) cooling of the macrophages in a medium at a rate of 1 to 5° C. until the macrophages in the medium are frozen; or iii) warming of the macrophages in the medium at a rate of 1 to 5° C. per minute until a temperature of 35-37° C. is reached.

According to this main aspect of the invention, during either or both freezing and thawing, the macrophages in the medium are allowed to "acclimatise" to the changing temperature, by maintaining a temperature of 2-12° C. for at least 30 minutes. Subsequent to or following this step, the macrophages for cryopreservation are then progressively cooled at a steady rate of 1-5° C. per minute, and similarly, for thawing, the method involves the progressive warming of the cryopreserved macrophages at a steady rate of 1-5° C. per minute. Thus, following the step of maintaining the macrophages at a temperature of 2-12° C., the macrophages are exposed to a change of temperature at a constant rate of 1-5° C. The change in temperature is cooling when the macrophages are cryopreserved or warming when the cryopreserved macrophages are warmed. This cooling or warming progresses until a desired temperature is reached. In terms of cryopreserving macrophages, this temperature may be about −80° C., but alternatively can be any temperature colder than −40° C., for example −45° C., −50° C., −55° C., −60° C., −65° C., −70° C., −75° C., −80° C., −85° C. or any temperature colder than this. In terms of thawing cryopreserved macrophages, the desired temperature may be a body temperature, suitably 35° C. to 37° C. Thus, rather than using a standard technique of simply progressively cooling when cryopreserving, the inventors have found that macrophages need to be cooled, then held at a temperature of 2-12° C. for at least 30 minutes, after which further cooling to frozen can be done at a steady rate. This permits the macrophages to retain viability after thawing.

Similarly, rather than using a standard technique of fast warming in a water bath, the inventors have found that macrophages need to be warmed, then held at a temperature of 2-12° C. for at least 30 minutes, after which further warming can be done at a steady rate. Optionally, after the macrophages have been held at a temperature of 2-12° C. for at least 30 minutes, medium can be added to dilute the macrophages prior to further warming. Optionally the macrophages may be maintained at a temperature of about 37° C. once this temperature has been reached. This is prior to any further use of said macrophages.

The common step of maintaining the macrophages at 2-12° C. for 30 minutes during either freezing or thawing is unique, and provides a unifying concept for the present invention. Advantageously, this step is performed when both freezing and thawing macrophages, but equally each of the techniques may be applied in isolation, since either method alone improves viability.

According to a principle aspect of the present invention, there is provided a method of cryopreserving macrophages, the method comprising:

(a) Placing macrophages in medium;

(b) Cooling the medium containing macrophages of step (a) to a temperature of between about 2-12° C. and maintaining the cooled medium at a temperature of between about 2-12° C. for a period of at least 30 minutes; and (c) Freezing the medium containing macrophages of step (b) at a cooling rate of 1-5° C. per minute.

According to any aspect of the invention, the macrophages may be cooled to a temperature of 2-12° C. quickly, or the cooling may be progressive, for example at a cooling rate of 1-5° C. per minute.

According to any aspect of the invention, the macrophages may be cooled to a temperature of about −80° C. during the freezing step.

According to a principal aspect of the present invention, there is provided a method of cryopreserving macrophages, the method comprising:

(a) Placing macrophages in medium;

(b) Cooling the medium containing macrophages of step (a) to a temperature of between about 2-12° C. and maintaining the cooled medium at a temperature of between about 2-12° C. for a period of at least 30 minutes; and (c) freezing the medium containing macrophages of step (b) at a cooling rate of 1-5° C. per minute.

According to a primary aspect of the present invention, there is provided a method of thawing cryopreserved macrophages, wherein the cryopreserved macrophages are in a medium, the method comprising:

(a) warming cryopreserved macrophages to a temperature of between about 2-12° C. and maintaining the medium at a temperature of between about 2-12° C. for a period of at least 30 minutes; and (b) warming the cryopreserved macrophages of step (a) at a warming rate of 1-5° C. per minute until a temperature of 35-37° C. is reached.

Optionally the thawing method comprises one or more additional steps:

(i) diluting the cryopreserved macrophages of step (a) in medium; and/or (ii) maintaining the macrophages of step (b) at a temperature of about 37° C. for at least 30 minutes.

According to any aspect of the invention, the temperature at which the macrophages are maintained is between 2-12° C., suitably 2-10° C., suitably 2-8° C., suitably 2-6° C., suitably 4° C.

According to any aspect of the invention, the macrophages are maintained at the specified temperature for at least 30 minutes, at least 40 minutes, at least 50 minutes, at least 60 minutes, at least 80 minutes, at least 100 minutes or at least 120 minutes.

According to any aspect of the invention, the macrophages are in a cryoprotectant medium, suitably a GMP grade cryoprotectant medium. Suitable media are discussed herein.

According to any aspect of the invention, the macrophages are present in a medium at a specified cell concentration per mL medium. Suitably the macrophages are present in a medium in at least the following specified cell concentration per mL medium: $5 \times 10^6$/ml, $6 \times 10^6$/mL, $7 \times 10^6$/mL, $8 \times 10^6$/mL, $9 \times 10^6$/mL, $1 \times 10^7$/mL, $2 \times 10^7$/mL, $3 \times 10^7$/mL, $4 \times 10^7$/mL, $5 \times 10^7$/mL, $6 \times 10^7$/mL, $7 \times 10^7$/mL, $8 \times 10^7$/mL, $9 \times 10^7$/mL, $1 \times 10^8$/mL, $2 \times 10^8$/mL, $3 \times 10^8$/mL, $4 \times 10^8$/mL or $5 \times 10^8$/mL. Suitably the concentration is at least $1 \times 10^7$/mL.

According to a first aspect of the present invention, there is provided a method of cryopreserving macrophages, the method comprising:

(a) Placing macrophages in medium;

(b) Cooling the medium containing macrophages of step (a) to a temperature of between about 2-22° C. at a cooling rate of 1-5° C. per minute, and maintaining the cooled medium at a temperature of between about 2-22° C. for a period of at least 30 minutes; and (c) Freezing the medium containing macrophages of step (b).

According to a second aspect of the present invention, there is provided a method of thawing cryopreserved macrophages, the method comprising:

(a) Warming cryopreserved macrophages to a temperature of between about 4-10° C., and maintaining the macrophages at a temperature of between about 4-10° C. for a first period, wherein the first period is at least 30 minutes;

(b) Diluting the cryopreserved macrophages of step (a) in medium; and (c) Warming the cryopreserved macrophages of step (b) to a temperature of about 37° C. and maintaining the macrophages at a temperature of about 37° C. for a second period, wherein the second period is at least 30 minutes.

According to a third aspect of the present invention, there is provided a method comprising the steps of the first aspect and the steps of the second aspect.

In one embodiment, therefore, there is provided a method of cryopreserving and thawing macrophages, the method comprising:

(a) Placing macrophages in medium;

(b) Cooling the medium of step (a) containing macrophages to a temperature of between about 2-22° C. at a cooling rate of 1-5° C. per minute, and maintaining the cooled medium at a temperature of between about 2-22° C. for a period of at least 30 minutes;

(c) Freezing the medium of step (b) containing macrophages to produce cryopreserved macrophages;

(d) Warming the cryopreserved macrophages of step (c) to a temperature of between about 4-10° C., and maintaining the macrophages at a temperature of between about 4-10° C. for a first period, wherein the first period is at least 30 minutes;

(e) Diluting the cryopreserved macrophages of step (d) in medium; and (f) Warming the cryopreserved macrophages of step (e) to a temperature of about 37° C., and maintaining the macrophages at a temperature of about 37° C. for a second period, wherein the second period is at least 30 minutes.

In an additional aspect there is provided a method of cryopreserving and thawing macrophages, the method comprising:

(a) Placing macrophages in medium at a concentration of at least $5 \times 10^6$/ml;

(b) Cooling the medium of step (a) containing macrophages to a temperature of between about 2-12° C., and maintaining the cooled medium at a temperature of between about 2-12° C. for a period of at least 30 minutes;

(c) Freezing the medium of step (b) containing macrophages at a cooling rate of 1-5° C. per minute to produce cryopreserved macrophages;

(d) Warming the cryopreserved macrophages of step (c) to a temperature of between about 2-12° C., and maintaining the macrophages at a temperature of between about 2-12° C. for a first period, wherein the first period is at least 30 minutes;

(e) Diluting the cryopreserved macrophages of step (d) in medium; and (f) Warming the cryopreserved macrophages of step (e) to a temperature of about 37° C., and maintaining the macrophages at a temperature of about 37° C. for a second period, wherein the second period is at least 30 minutes.

Such a method may include an additional step i) after c): storing the cryopreserved macrophages in a freezer, such as a −80° C. freezer. The macrophages may be stored for at least a week, at least a month, at least 6 months or at least a year.

According to a fourth aspect of the present invention, there is provided cryopreserved macrophages produced by the method of the main, principal or first aspect.

According to a fifth aspect of the present invention, there is provided thawed macrophages produced by the method of the main, primary or second aspect.

According to a sixth aspect of the present invention, there is provided thawed macrophages produced by the method of the third or additional aspect.

According to any aspect or embodiment of the invention, the method or methods may be GMP compliant, such as a method suitable to provide a clinical grade macrophage.

Advantageously, the inventors have discovered a novel method of cryopreserving macrophages and a novel method of thawing macrophages which can be used either alone or together. The methods provide an increased yield of macrophages, which are GMP-compliant, and have a higher viability than any cryopreservation and thawing methods available in the art. Furthermore, the macrophages retain key physiological traits such as good phagocytotic ability.

The inventors have found that macrophages should not simply be cooled to a freezing temperature at a steady rate, nor indeed thawed at a rapid rate once ready to use the cryopreserved cells. As mentioned previously, commercially available cell cryopreservation methods tend to involve the slow cooling of cells progressively to the desired freezing temperature. To reverse this process, cells are generally warmed quickly to 37° C.

Surprisingly, the inventors have found that macrophages do not survive well under standard conditions, but instead require at least one temperature acclimatisation step during the freezing and thawing process. This acclimatisation step involves the maintenance of the macrophages in the medium at a particular temperature for a period of at least 30 minutes before exposing the macrophages to a further change in temperature. Such a step appears to allow the macrophages the opportunity of adapting to the either cooling or rising temperatures and prevent damage to the cells during these potentially damaging processes.

Thus, the present invention, in a further aspect, relates to a method of either cryopreserving macrophages or thawing cryopreserved macrophages comprising the steps of:

(a) warming or cooling the temperature of said macrophages to a temperature of 2-12° C.;

(b) maintaining the temperature of said macrophages at a temperature of 2-12° C. for at least 30 minutes; and (c) warming or cooling the temperature of said macrophages at a steady rate of 1-5° C. to reach the desired temperature.

In one embodiment wherein said macrophages are in a cryopreservation medium at a concentration of at least $5 \times 10^6$/ml, at least $1 \times 10^7$/mL or at least $1 \times 10^8$/mL.

Without being bound by theory, the inventors postulate that it is the step of maintaining the macrophages at a temperature of 2-12° C. during either freezing or thawing procedures that provides the macrophages with the ability to survive the process much better than the standard techniques.

In relation to cryopreservation, the temperature of the macrophages in the cryopreservation medium may be gradually reduced to 2-10° C. at a rate of 1-5° C. per minute. Suitably, the temperature of the macrophages in the cryopreservation medium may be reduced to 2-10° C. quickly (at a rate exceeding 5° C. per minute). Further, once the cells have been maintained at 2-10° C. for at least 30 minutes, they may be frozen by any suitable means. Suitably, the freezing process involves the temperature of the macrophages in the cryopreservation medium being gradually reduced at a rate of 1-5° C. per minute. This gradual reduction in temperature may be maintained until the macrophages have reached at least a temperature of −40° C., suitably −80° C.

Surprisingly, the inventors have found that during cryopreservation, the addition of a cool down step at a milder temperature prior to a steady rate of cooling to freezing at typical temperatures of −80° C. or lower allows the macrophages to adapt to the colder temperatures. It also prevents damage to the cells which occurs during rapid freezing.

In relation to thawing the cryopreserved macrophages, the temperature of the cryopreserved macrophages in the cryopreservation medium may be warmed to 2-12° C. by any suitable means. Further, once the cells have been maintained at 2-12° C. for at least 30 minutes, they may be warmed to around 37° C. by any suitable means. Once the macrophages have been warmed to around 37° C., a second acclimatisation step may be used, such that the macrophages are maintained at around 37° C. for at least 30 minutes. Around 37° C. may include 36-38° C., notably 36.5 to 37.5° C., since normal body temperature can fluctuate in this range. Once maintained at around 37° C. for at least 30 minutes, the macrophages can be further cultured or used therapeutically. Subsequent to or after the step of holding the thawing macrophages at 2-12° C., medium may be added to the macrophages to dilute them.

Similarly, the inventors have found that during thawing, the inclusion of an initial warming step at a cooler temperature than room or in vivo body temperature allows the macrophages to adapt to the warmer temperatures and become resilient. Furthermore, increasing the second warming step to at least 1 hour further allows the macrophages to recover vital functions before being used.

Therefore, the methods of the invention provide optimised cryopreservation and thawing for macrophages, particularly for macrophages which are to be used in therapy. The methods of the invention advantageously allow the long-term storage of macrophages which are suitable for clinical use for at least up to 6 months with no loss in expected physiological functions, and without requiring specialist laboratory equipment.

Furthermore, the methods of the invention apply equally to all types of macrophage, whether polarised or unpolarised, whether mature, M1-like or M2-like. The methods of the invention applies to all macrophages, regardless of source. Thus, the macrophages may be natural macrophages, derived from monocytes or other progenitor cells in the laboratory by any suitable means, or derived from pluripotent stem cells.

Further aspects of the invention are defined as follows:

In a further aspect, there is provided a cryopreserved therapeutic composition comprising a population of cryopreserved macrophages wherein upon thawing, said macrophages have a viability of at least 60%.

In one embodiment, the cryopreserved macrophages are according to the fourth aspect.

In one embodiment, the cryopreserved macrophages are thawed according to the method of the second aspect.

In a further aspect, there is provided a therapeutic composition comprising a population of thawed macrophages wherein said macrophages have a viability of at least 60%. Suitably viability may be at least 65% or at least 70%.

In one embodiment, the thawed macrophages are according to the fifth or sixth aspect.

In one embodiment, the cryopreserved macrophages are thawed according to the method of the second aspect.

In a further aspect there is provided cryopreserved macrophages according to the fourth aspect, for use as a medicament.

In a further aspect there is provided thawed macrophages according to the fifth or sixth aspect, for use as a medicament.

In a further aspect, there is provided cryopreserved macrophages according to the fourth aspect, for use in the treatment of a liver disease.

In a further aspect, there is provided thawed macrophages according to the fifth or sixth aspect, for use in the treatment of a liver disease.

In a further aspect, there is provided use of a cryopreserved macrophage according to the fourth aspect in the manufacture of a medicament for treating a disease in a subject, the manufacture comprising the steps of:

(a) Placing macrophages in medium;

(b) Cooling the medium containing macrophages of step (a) to a temperature of between about 2-22° C. at a cooling rate of 1-5° C. per minute, and maintaining the cooled medium at a temperature of between about 2-22° C. for a period of at least 30 minutes; and (c) Freezing the medium containing macrophages of step (b); and (d) Formulating some or all of said macrophages into a medicament for administration to the subject.

In a further aspect, there is provided use of a cryopreserved macrophage according to the fourth aspect in the manufacture of a medicament for treating a disease in a subject, the manufacture comprising the steps of:

(a) Placing macrophages in medium;

(b) Cooling the medium containing macrophages of step (a) to a temperature of between about 2-12° C. and maintaining the cooled medium at a temperature of between about 2-12° C. for a period of at least 30 minutes; and (c) Freezing the medium containing macrophages of step (b) at a cooling rate of 1-5° C. per minute; and (d) Formulating some or all of said macrophages into a medicament for administration to the subject.

In a further aspect, there is provided use of a thawed macrophage according to the fifth aspect in the manufacture of a medicament for treating a disease in a subject, the manufacture comprising the steps of:

(a) Warming cryopreserved macrophages to a temperature of between about 4-10° C., and maintaining the macrophages at a temperature of between about 4-10° C. for a first period, wherein the first period is at least 30 minutes;

(b) Diluting the cryopreserved macrophages of step (a) in medium; and (c) Warming the cryopreserved macrophages of step (b) to a temperature of about 37° C., and maintaining the macrophages at a temperature of about 37° C. for a second period, wherein the second period is at least 30 minutes; and (d) Formulating some or all of said macrophages into a medicament for administration to the subject.

In a further aspect, there is provided use of a thawed macrophage according to the sixth aspect in the manufacture of a medicament for treating a disease in a subject, the manufacture comprising the steps of:

(a) Placing macrophages in medium;

(b) Cooling the medium of step (a) containing macrophages to a temperature of between about 2-22° C. at a cooling rate of 1-5° C. per minute, and maintaining the cooled medium at a temperature of between about 2-22° C. for a period of at least 30 minutes;

(c) Freezing the medium of step (b) containing macrophages to produce cryopreserved macrophages;

(d) Warming the cryopreserved macrophages of step (c) to a temperature of between about 4-10° C., and maintaining the macrophages at a temperature of between about 4-10° C. for a first period, wherein the first period is at least 30 minutes;

(e) Diluting the cryopreserved macrophages of step (d) in medium; and (f) Warming the cryopreserved macrophages of step (e) to a temperature of about 37° C., and maintaining the macrophages at a temperature of about 37° C. for a second period, wherein the second period is at least 30 minutes; and (g) Formulating some or all of said macrophages into a medicament for administration to the subject.

In one embodiment, the disease is a liver disease.

In a further aspect, there is provided use of a thawed macrophage according to the sixth aspect in the manufacture of a medicament for treating a disease in a subject, the manufacture comprising the steps of:

(a) Placing macrophages in medium;

(b) Cooling the medium of step (a) containing macrophages to a temperature of between about 2-12° C., and maintaining the cooled medium at a temperature of between about 2-12° C. for a period of at least 30 minutes;

(c) Freezing the medium of step (b) containing macrophages at a cooling rate of 1-5° C. per minute to produce cryopreserved macrophages;

(d) Warming the cryopreserved macrophages of step (c) to a temperature of between about 4-10° C., and maintaining the macrophages at a temperature of between about 4-10° C. for a first period, wherein the first period is at least 30 minutes;

(e) Diluting the cryopreserved macrophages of step (d) in medium; and (f) Warming the cryopreserved macrophages of step (e) to a temperature of about 37° C., and maintaining the macrophages at a temperature of about 37° C. for a second period, wherein the second period is at least 30 minutes; and (g) Formulating some or all of said macrophages into a medicament for administration to the subject.

In one embodiment, the disease is a liver disease.

In one embodiment of any of the aspects, the macrophages are hMDMs. In one embodiment of any of the aspects, the macrophages are hMDMs produced by a 'day5' method, suitably produced from monocytes by a 'day5' method.

According to any aspect of the invention, the macrophages may be prepared from monocytes. The preparation of the macrophages from the monocytes is desirably according to GMP standards, such that the macrophages can have clinical utility. The present inventors have developed a method, described in co-pending application PCT/GB2021/051294, which may be referred to as the "day5" method, but relates to an effective and efficient way of producing macrophages from monocytes that involves the culturing of monocytes in the same culture medium together with a growth factor for a period of at least three days, at which point markers of macrophage characteristics emerge. In such a method it is not necessary to further "feed" the cells with additional materials. Such macrophages have been tested in the cryopreservation method described herein. Any alternative method of deriving macrophages from monocytes is equally applicable.

Further features and embodiments of the present invention will now be described. Features are not restricted to any particular aspect or embodiment of the invention and may be combined in any compatible way.

DESCRIPTION

The following definitions are provided.

'hMDM' as used in the present invention refers to human monocyte-derived macrophages. Monocyte-derived means macrophages differentiated from monocytes. Monocytes are the natural precursors of macrophages and dendritic cells; they are contained in blood and bone marrow.

'unpolarised macrophage' as used in the present invention refers to a mature macrophage which has not received any further stimulation to induce particular functional capacity, unpolarised macrophages may also be referred to as naive or non-activated macrophages.

'polarized macrophage' as used in the present invention refers to a macrophage which has received environmental stimulus to become activated into a particular phenotype such as the M1-like or M2-like phenotype. The M1-like and M2-like phenotypes are described hereinbelow, but may represent two states of a continuum of cell types.

'macrophage' refers to a phagocytic cell which is responsible for detecting, engulfing and destroying pathogens and apoptotic cells, and which is produced through the differentiation of monocytes. The term refers to a macrophage which may be polarised or unpolarised.

'mature macrophage' refers to a macrophage which expresses mature cell surface markers, preferably CCR2−, CD14+, CD206+, CD163+, CD169+, 25F9+, and CD86+.

An 'M1 polarising factor' as used in the present invention refers to a factor which stimulates an unpolarised macrophage into an M1-like phenotype and may refer to one or more of: GM-CSF, IFNγ, and TLR agonists, such as LPS, for example.

An 'M2 polarising factor' as used in the present invention refers to a factor which stimulates an unpolarised macrophage into an M2-like phenotype, and may refer to one or more of: IL10, IL4, IL13, and poly(I:C), for example.

'GMP-compliant' as used in the present invention means that the method complies with good manufacturing practice. By way of example a GMP-compliant medium has to be serum-free, antibiotic-free and xenoprotein-free (animal substance free). The WHO provides guidance on what is required for good manufacturing practice: "Chapter 1: WHO good manufacturing practices: Main principles for pharmaceutical products". Quality Assurance of Pharmaceuticals: A compendium of guidelines and related materials—Good manufacturing practices and inspection. 2 (2nd updated ed.). WHO Press. pp. 17-18. ISBN 9789241547086.

'treatment' as used in the present invention means an intervention in a physiological condition which prevents, reduces, or removes the clinical symptoms associated with a given physiological condition in a subject.

By 'subject' or 'individual' or 'animal' or 'patient' is meant any subject, particularly a mammalian subject, for whom diagnosis, prognosis, or therapy is desired, except where the subject is defined as a 'healthy subject'. Mammalian subjects include humans; domestic animals; farm animals, such as dogs, cats, guinea pigs, rabbits, rats, mice, horses, cattle, cows, and so on.

'day5 no feed' or 'day5' as used in the present invention in relation to a method/protocol refers to a method/protocol to produce macrophages which lasts between 3 to 5 days, optionally 4-5 days. 3-5 days typically refers to a period of about 72-120 hours. 4-5 days typically refers to a period of about 96-120 hours. These periods may vary by +/−10 hours, preferably +/−5 hours, preferably +/−2 hours.

Suitably therefore, the method of the invention may last between 62 and 130 hours, suitably between 86 and 130 hours, suitably between 90 and 125 hours suitably between 96 and 120 hours.

'day7 plus re-feed' or 'day7' as used in the present invention in relation to a method/protocol refers to a longer method/protocol to produce macrophages. These methods last for a period of around 7 days which typically refers to a period of about 168 hours. This period may vary by +/−10 hours, preferably +/−5 hours, preferably +/−2 hours.

It is to be noted that the term "a" or "an" entity refers to one or more of that entity.

'about' means +/−10% of the value given, +/−9%, +/−8%, +/−7%, +/−6%, +/−5%, +/−4%, +/−3%, +/−2%, +/−1%, unless otherwise stated.

Medium for Freezing

The present invention relates to a method of cryopreserving macrophages in which macrophages are placed in a medium prior to freezing. The inventors have found that the qualities of the medium can affect the properties of the resulting macrophages and have optimised the medium to suit the method. Such medium may also be described as a "cryopreservation medium".

Suitably therefore, the medium is suitable for freezing cells and may be known as a 'freezing medium'. Suitably the medium is GMP-compliant. Suitably the medium is serum free. Suitably the medium is free from animal substances (xeno-free).

Suitably, the medium is suitable for cryopreserving cells and contains a cryoprotectant. Those skilled in the art are aware of suitable cryopreserving mediums, which are commercially available from manufacturers.

A cryoprotectant may be described as a chemical that dissolves in water and lowers the melting point of water. Common examples are glycerol, ethylene glycol, propylene glycol, and dimethylsulfoxide (DMSO). Cryoprotectants are effective at reducing the melting point of water, do not precipitate or form hydrates, and are relatively non-toxic to cells at high concentrations. Most commonly used cryoprotectants are a class called penetrating cryoprotectants. These are small molecules that cross cell membranes, notably due to their molecular mass being typically less than 100 daltons. By entering and remaining inside cells, penetrating cryoprotectants prevent excessive dehydration of cells during the freezing process. Non-penetrating cryoprotectants are large molecules, usually polymers. They inhibit ice growth by the same mechanisms as penetrating cryoprotectants, but do not enter cells. Polyethylene glycol (PEG) and polyvinylpyrrolidone (PVP) are examples. They reduce the amount of penetrating cryoprotectants needed by mimicking outside the cell the cryoprotective effects of proteins inside the cell. Broadly, a cryoprotectant may be a polyhydroxy compound, sugar, protein, polymer, amino acid, salt, amine, surfactant, and mixtures thereof. The polyhydroxy compound is one of the typical types of cryoprotectants. Common cryoprotectant examples of this type include glycerin, mannitol, sorbitol, inositol, thiol, and polyethylene glycol. In terms of sugars, sucrose and trehalose are both cryoprotectants. Common amino-acid cryoprotectant examples are proline and tryptophan, sodium glutamate, glycine, lysine hydrochloride, sarcosine, L-tyrosine, phenylalanine and arginine, which may act to help cryopreservation by inhibiting the pH effect of the freezing of buffers. Human albumin may be a protein cryoprotectant.

Those skilled in the art will be aware of suitable cryoprotectants. DMSO is the most widely used, but in some instances alternatives are being sought in case of undesirable effects of DMSO. In the Examples provided here, media with and without DMSO were seen to be suitable for use in the methods of the invention.

Suitably, the medium suitable for cryopreserving cells will contain at least one cryoprotectant. Optionally the cryoprotectant is DMSO. Optionally the cryoprotectant is DMSO-free. Several commercially available GMP grade cryopreservation media are available commercially that do not contain DMSO:

PRIME-XV® FreezlS DMSO-Free from Irvine Scientific—Cryoprotectant used is not disclosed. Has 'cGMP' Drug Master File registration FREEZEstem™ from BioLamina, Cryoprotectant used is not disclosed. 'GMP-compliant' ISO13485

STEM-CELLBANKER® 'GMP grade' (DMSO free)—Zenoaq Resource (supplier Amsbio). Cryoprotectant used is 1,2-dihydroxypropane serum, Glucose and Polymer, Drug Master File (US) 'GMP-grade'.

Suitably the medium suitable for cryopreservation is also suitable for culturing macrophages.

Suitably, the medium used in the methods of the invention is formed by mixing at least two medium in appropriate proportions. This is done to ensure that an effective level of cryoprotectant(s) are present, and to provide the macrophages with the conditions required (such as pH, sugars and the like).

Suitably, the medium used in the methods of the invention is based upon a mixture of albumin, such as human albumin, and DMSO. Such can be prepared to a GMP grade.

Suitable commercially available medium for use in the methods in the invention include any one or more of CryoStor®CS2 (2% DMSO), CS5 (5% DMSO) or CS10 (10% DMSO)—all available from BioLife Solutions, WA, US. Such may be used alone as the medium into which the macrophages are placed, or these may be mixed with other components to provide a combined medium. Suitable components/media to combine with the CryoStor series of media (CS2, CS5 or CS10) are PlasmaLyte, human albumin (optionally recombinant), Tex MACS™ (GMP—Miltenyi Biotec), Optionally, the medium may be DMSO free, for example PRIME-XV® FreezIS DMSO-Free from Irvine Scientific or STEM-CELLBANKER® 'GMP grade'. This may be used as the sole medium, or in combination with other components to provide a mixed solution.

In one embodiment, the cryopreservation medium is a mixture of CS10 with TexMACS. In an alternative embodiment, the cryopreservation medium is a mixture of CS10 with PlasmaLyte. PlasmaLyte is a family of balanced crystalloid solutions with multiple different formulations available worldwide according to regional clinical practices and preferences. It closely mimics human plasma in its content of electrolytes, osmolality, and pH Suitably the medium is selected from any suitable macrophage medium. Suitably the medium may be a mixture of suitable macrophage medium. Suitably the medium is selected from one or more of: human albumin, plasmaLyte, TexMACS, DMSO, CS10, and PrimeXV. In one embodiment, the freezing medium is CS10. In one embodiment, the freezing medium is a mixture of CS10 and TexMACs.

Suitably the medium comprises between 40-100% CS10, CS5 or CS2, suitably between 45-100%, suitably between 50-100%, suitably between 55-100%, suitably between 60-100% CS10, CS5 or CS2. Suitably the medium comprises about 66% CS10, CS5 or CS2.

Suitably the medium comprises between 0-60% Tex-MACS, suitably between 10-50%, suitably between 20-40%, suitably between 25-35%. Suitably the medium comprises about 33% TexMACS.

In one embodiment, the medium comprises about 66% CS10 and 33% TexMACS.

In one embodiment, the medium comprises 100% CS10.

Suitably the medium may comprise further additives. Suitably the medium may comprise one or more cryoprotectants.

Suitably the concentration of cryoprotectant in the medium is between 5-30%, suitably between 7-25%, suitably between 10-20%. In one embodiment, the concentration of cryoprotectant in the medium is 10%.

Suitably the medium may comprise albumin.

Suitably the concentration of albumin in the medium is between 5-30%, suitably between 7-25%, suitably between 10-20%. In one embodiment, the concentration of albumin in the medium is 10%.

Interestingly, the inventors have determined that the cell concentration appears to be important for the process of cryopreservation. This is described in the Examples. Notably, the success of cryopreserving and subsequently thawing the cryopreserved cells appeared to increase when the macrophages were present in the medium at a cell concentration of at least $5\times10^6$/mL., suitably at least $1\times10^7$/m L.

Suitably the macrophages are placed into the medium. Suitably the macrophages are present in the medium at a cell concentration of between $1\times10^6$-$1\times10^8$/mL, suitably $1\times10^6$/mL, suitably $2\times10^6$/mL, suitably $3\times10^6$/mL, suitably $4\times10^6$/mL, suitably $5\times10^6$/mL, suitably $6\times10^6$/mL, suitably $7\times10^6$/mL, suitably $8\times10^6$/mL, suitably $9\times10^6$/mL, suitably $1\times10^7$/mL, suitably $2\times10^7$/mL, suitably $3\times10^7$/mL, suitably $4\times10^7$/mL, suitably $5\times10^7$/mL, suitably $6\times10^7$/mL, suitably $7\times10^7$/mL, suitably $8\times10^7$/mL, suitably $9\times10^7$/mL, suitably $1\times10^8$/mL, suitably $2\times10^8$/mL, suitably $3\times10^8$/mL, suitably $4\times10^8$/mL, suitably $5\times10^8$/m L.

Suitably the macrophages are present in the medium at a cell concentration of between $5\times10^6$/mL to $5\times10^8$/m L, suitably $2\times10^6$-$9\times10^7$/m L, suitably between $3\times10^6$-$8\times10^7$/m L, suitably between $4\times10^6$-$7\times10^7$/mL, suitably between $5\times10^6$-$6\times10^7$/m L, suitably between $6\times10^6$-$5\times10^7$/m L, suitably between $6\times10^6$-$5\times10^7$/m L, suitably between $7\times10^6$-$4\times10^7$/m L, suitably between $8\times10^6$-$3\times10^7$/m L, suitably between $9\times10^6$-$2\times10^7$/m L.

Suitably, the macrophages are present in the medium at a cell concentration of at least $5\times10^6$/mL, at least $1\times10^7$/mL, at least $5\times10^7$/mL, at least $1\times10^8$/mL or at least $5\times10^8$/m L.

Suitably the macrophages are present in the medium at a cell concentration of between $2\times10^7$-$5\times10^7$/m L.

In one embodiment, the macrophages are present in the medium at a cell concentration of $2\times10^7$/m L. Suitably in such an embodiment, the macrophages have been produced in vitro. Suitably the macrophages are derived from monocytes which have been isolated from a healthy subject. Suitably the macrophages are derived from progenitor cells which have been isolated from a health subject.

In one embodiment, the macrophages are present in the medium at a cell concentration of $5\times10^7$/mL. Suitably in such an embodiment, the macrophages have been produced in vitro. Suitably from monocytes which have been isolated from a subject having a disease. Suitably in such an embodiment, the monocytes have been isolated from a subject having a liver disease. Suitably the monocytes have been isolated from a subject with fibrotic disease.

Cooling

The cryopreservation methods of the invention advantageously incorporates a cool down step in which the macrophages in medium are cooled for a period of time before freezing. Advantageously, following this initial cooling step, the macrophages are maintained at a cooled temperature for a period of time, prior to the freezing step.

Typically, macrophages are kept and cultured at temperatures of around 37° C. akin to an in vivo temperature. Therefore, the cool down step of the present invention reduces the temperature below this to a temperature of around 2° C. up to room temperature, which is typically around 18-22° C. Suitably, the temperature is cooled to a temperature between 2-12° C., suitably 2-8° C., suitably 2-6° C., suitably 4° C.

Suitably this cooling step is step (b) of the method of cryopreserving macrophages. Suitably the cooling step must take place before the freezing step. Suitably the cooling step takes place immediately prior to the freezing step. Suitably the cooling step must take place after the addition of medium to the macrophages.

Suitably cooling the medium of step (a) comprises cooling to a temperature of between about 2-22° C. and maintaining the cooled medium at a temperature of between about 2-22° C. for a period of at least 30 minutes.

Suitably the cooled medium is maintained at a temperature of between about 2-22° C. for a period of between 30 to 120 minutes, suitably between 30 to 110 minutes, suitably between 30 to 100 minutes, suitably between 30 to 90 minutes, suitably between 30 to 80 minutes, suitably between 30 to 70 minutes, suitably between 30 to 60 minutes.

In one embodiment the cooled medium is maintained at a temperature of between about 2-22° C. for period of up to 60 minutes, suitably of between 30 to 60 minutes.

Suitably the cooling rate during cooling of the medium of step (a) is between 1-5° C. per minute. Suitably the cooling rate during cooling of the medium of step (a) may be selected from: 1.0° C., 1.1° C., 1.2° C., 1.3° C., 1.4° C., 1.5° C., 1.6° C., 1.7° C., 1.8° C., 1.9° C., 2° C., 2.1° C., 2.2° C., 2.3° C., 2.4° C., 2.5° C., 2.6° C., 2.7° C., 2.8° C., 2.9° C., 3° C., 3.1° C., 3.2° C., 3.3° C., 3.4° C., 3.5° C., 3.6° C., 3.7° C., 3.8° C., 3.9° C., 4° C., 4.1° C., 4.2° C., 4.3° C., 4.4° C., 4.5° C., 4.6° C., 4.7° C., 4.8° C., 4.9° C., 5° C. per minute.

Suitably the cooling rate during cooling of the medium of step (a) may be between 1° C. to 4° C. per minute, suitably between 1° C. to 3° C. per minute, suitably between 1° C. to 2° C. per minute, suitably about 1° C. per minute.

Suitably the cooling rate during cooling of the medium of step (a) may be greater than 5° C. per minute.

In one embodiment, cooling the medium of step (a) comprises cooling to a temperature of between about 2-22° C. at a rate of about 1° C. per minute.

Suitably cooling the medium of step (a) comprises cooling to a temperature of between about 2-22° C., suitably between about 2-20° C., suitably between about 2-18° C., suitably between about 2-16° C., suitably between about 2-14° C., suitably between about 2-12° C., suitably between about 2-10° C., suitably between about 2-8° C., and maintaining the cooled medium at the same temperature.

In one embodiment, cooling the medium of step (a) comprises cooling to a temperature of between about 4-6° C., and maintaining the cooled medium at the same temperature.

The macrophages in the medium may be subjected to controlled cooling by any suitable mechanism. There are several means to achieve a cooling rate of around −1° to −5° C. per minute, including a programmable electronic freezing unit (such as CryoMed Freeze), or the use of insulated freezing chambers. Such are discussed further below in relation to the freezing step.

Freezing

The cryopreservation method of the invention further incorporates a freezing step in which the cooled macrophages in medium are frozen.

Suitably the freezing step is step (c) of the method of cryopreserving macrophages. Suitably the freezing step is the final step in the method of cryopreserving macrophages. Suitably the freezing step takes place after the cooling step. Suitably the freezing step takes place immediately after the cooling step.

Suitably, the freezing step (c) takes place by a cooling the macrophages at a cooling rate of between 1-5° C. per minute. Suitably the cooling rate during the freezing step of step (c) may be selected from: 0.1° C., 1.0° C., 1.1° C., 1.2° C., 1.3° C., 1.4° C., 1.5° C., 1.6° C., 1.7° C., 1.8° C., 1.9° C., 2° C., 2.1° C., 2.2° C., 2.3° C., 2.4° C., 2.5° C., 2.6° C., 2.7° C., 2.8° C., 2.9° C., 3° C., 3.1° C., 3.2° C., 3.3° C., 3.4° C., 3.5° C., 3.6° C., 3.7° C., 3.8° C., 3.9° C., 4° C., 4.1° C., 4.2° C., 4.3° C., 4.4° C., 4.5° C., 4.6° C., 4.7° C., 4.8° C., 4.9° C., 5° C. per minute.

Suitably the cooling rate during freezing of the medium of step (c) may be between 1° C. to 4° C. per minute, suitably between 1° C. to 3° C. per minute, suitably between 1° C. to 2° C. per minute, suitably about 1° C. per minute.

Suitably freezing of the macrophage containing medium takes place at a temperature selected from: −70° C., −71° C., −72° C., −73° C., −74° C., −75° C., −76° C., −77° C., −78° C., −79° C., −80° C., −81° C., −82° C., −83° C., −84° C., −85° C., −86° C., −87° C., −88° C., −89° C., −90° C., −91° C., −92° C., −93° C., −94° C., −95° C., −96° C., −97° C., −98° C., and −100° C.

Suitably freezing of the macrophage containing medium takes place at a temperature between −70° C. to −180° C., between −70° C. to −170° C., between −70° C. to 160° C., between −70° C. to −150° C., between −70° C. to −140° C., between −70° C. to −130° C., between −70° C. to −120° C., between −70° C. to −110° C., between −70° C. to −100° C., between −70° C. to −90° C.

In one embodiment, the freezing of the macrophage containing medium takes place at a temperature of about −80° C.

Suitably freezing of the macrophage containing medium may be carried out by any known freezing method in the art. Suitably the freezing is carried out by placing the medium in a freezer, such as a controlled rate freezer, or by contacting the medium with liquid nitrogen, for example.

In one embodiment, the macrophage containing medium is frozen by placing it in a freezer. Suitably a controlled rate freezer, or by placing it in a device that enables controlled rate freezing for example Mr Frosty from ThermoFisher Scientific.

In one embodiment, a controlled-rate freezing chamber is used. There are several means to achieve a cooling rate of about −1° C. to −5° C. per minute. The best is with a computer controlled, programmable electronic freezing unit (such as CryoMed Freeze) which rigorously maintains this rate of cooling. A less costly approach used mostly in research is to place the cryopreservation vials into an insulated chamber and cool for 24 hours in a mechanical freezer at −70° C. or lower. There are several commercially available freezing chambers which achieve a cooling rate very close to −1° C. per minute (Mr. Frosty, Nalgene® 5100-0001; or StrataCooler®, Agilent Technologies 401349).

Suitably the macrophage containing medium is not frozen by liquid nitrogen. Such freezing may be too rapid.

Suitably the freezer may be any suitable freezer available in the art that can reach the appropriate temperatures for storing cells.

Suitably once the macrophages are frozen in the medium, they may be stored as such for long periods of time. Suitably the method may comprise a further step of storing the frozen medium containing the macrophages. Suitably in the freezer. Suitably the method may comprise a further step of storing the frozen medium of step (c). Suitably the frozen medium containing the macrophages may be frozen (and stored) for up to 2 years, suitably up to 1.5 years, suitably up to 1 year, suitably up to 6 months, suitably for up to 5 months, suitably for up to 4 months, suitably for up to 3 months, suitably for up to 2 months, suitably for up to 1 month, suitably for up to 3 weeks, suitably for up to 2 weeks, suitably for up to 1 week.

Suitably the frozen medium containing the macrophages may be frozen (and stored) for between 1 month to 1 year, suitably for between 6 months to 1 year. Suitably the macrophages may be stored for over a year.

Warming (Thawing)

The method of thawing macrophages of the invention comprises two steps of warming, the first warming step heats the cryopreserved macrophages to a temperature which is less than room temperature, and the second warming step heats the cryopreserved macrophages to typical in vivo temperature.

Methods in the art generally involve warming the cryopreserved cells as rapidly as possible, generally by placing the container of cryopreserved cells directly into a water bath at 37° C. The inventors have found that such is an inappropriate way to thaw cryopreserved macrophages. It is hypothesised that once cells are removed from the freezer, they warm at a rate of approximately 10° C. per minute at room temperature. The inventors have found, using their novel mechanism to thaw cryopreserved macrophages, that the gentle thawing and "acclimatisation" steps which hold the thawing macrophages at a particular temperature before thawing further, give a higher yield of viable macrophages.

Suitably the method of thawing cryopreserved macrophages may comprise a step of obtaining or producing cryopreserved macrophages. Suitably this step takes place before step (a). Suitably any cryopreserved macrophages may be used in the method of thawing of the invention. In one embodiment, this step incorporates the steps of the first aspect of the invention. Accordingly, in one embodiment, the cryopreserved macrophages are those produced by the method of the first aspect.

Suitably, the first warming step takes place before the second warming step.

Suitably the first warming step and the second warming step are separated at least by a step of diluting the cryopreserved macrophages in medium.

Suitably the first warming step takes place at a lower temperature than the second warming step.

Suitably the first warming step comprises warming the cryopreserved macrophages to a temperature of between about 2-12° C., and maintaining the macrophages at a temperature of between about 2-12° C. for a first period.

Suitably the first warming step comprises warming the cryopreserved macrophages to a temperature of between about 4-10° C. and maintaining the macrophages at a temperature of between about 4-10° C. for a first period.

Suitably the second warming step comprises warming the cryopreserved macrophages to a temperature of about 37° C. and maintaining the macrophages at a temperature of about 37° C. for a second period.

Suitably both the first and second warming steps are maintained for a first and second period of time respectively.

Suitably the first and second periods are at least 30 minutes. Suitably both the first and second periods are at least 1 hour. Suitably both the first and second periods are at least 2 hours. Suitably both the first and second periods are between 30 minutes to 5 hours, suitably between 1 to 4.5 hours, suitably between 2 to 4 hours, suitably between 2.5 to 3.5 hours. Suitably both the first and second periods are selected from any of the following: 30 minutes, 1 hour, 1.5 hours, 2 hours, 2.5 hours, 3 hours, 3.5 hours, 4 hours, 4.5 hours and 5 hours.

Suitably the first and second periods may take place for different periods of time, or the same amount of time. Suitably the first warming step comprises a first period of time and the second warming step comprises a second period of time.

In one embodiment, the first period is 1 hour.

In one embodiment, the second period is 2 hours.

Suitably the warming rate during warming of the medium of the first step and/or the second step is between 1-5° C. per minute. Suitably the warming rate during warming of the medium of the first step and/or the second step may be selected from: 1° C., 1.1° C., 1.2° C., 1.3° C., 1.4° C., 1.5° C., 1.6° C., 1.7° C., 1.8° C., 1.9° C., 2° C., 2.1° C., 2.2° C., 2.3° C., 2.4° C., 2.5° C., 2.6° C., 2.7° C., 2.8° C., 2.9° C., 3° C., 3.1° C., 3.2° C., 3.3° C., 3.4° C., 3.5° C., 3.6° C., 3.7° C., 3.8° C., 3.9° C., 4° C., 4.1° C., 4.2° C., 4.3° C., 4.4° C., 4.5° C., 4.6° C., 4.7° C., 4.8° C., 4.9° C., and 5° C. per minute.

Suitably the warming rate during warming of the medium of the first step and/or the second step may be between 1° C. to 5° C. per minute, suitably between 1° C. to 4.5° C. per minute, suitably between 1° C. to 4° C. per minute, suitably between 1° C. to 3.5° C. per minute, suitably between 1° C. to 3° C. per minute.

In one embodiment, the first warming step comprises warming to a temperature of between about 4-10° C. at a rate of about 1° C. per minute.

In one embodiment, the second warming step comprises warming to a temperature of about 37° C. at a rate of about 1° C. per minute.

Suitably the second warming step may be conducted under suitable atmospheric conditions. Suitably the macrophages are placed under atmospheric conditions that mimic the in vivo environment. Suitably the second warming step is conducted under carbon dioxide. Suitably the carbon dioxide is at a concentration of between 5 to 20%, suitably 5-10%, suitably 5%.

Suitably the first warming step comprises warming the cryopreserved macrophages to a temperature of between about 4-10° C., suitably between 4-9° C., suitably between 4-8° C., suitably between 4-7° C., suitably between 4-6° C., and maintaining the macrophages at this temperature.

In one embodiment, the first warming step comprises warming the cryopreserved macrophages to a temperature of between 4-6° C. and maintaining the macrophages at this temperature. In an alternative embodiment, the cryopreserved macrophages are warmed to a temperature of 2-12° C. and maintained at this temperature for a first period as defined above.

Those skilled in the art will be aware of suitable techniques and apparatus in which to perform controlled warming of the cryopreserved macrophages. Controlled thawing chambers are commercially available (e.g. ThawStar®, Biocision).

Medium for Diluting

In the methods of thawing cryopreserved macrophages of the invention, there may be included a step of diluting the cryopreserved macrophages in medium. Suitably this step takes place between the first and second warming steps.

Suitably this medium may be referred to as 'diluting medium'. Any appropriate diluting medium may be used, and those skilled in the art are aware of the numerous commercially available media for cell culture. A culture medium is a liquid designed to support the growth of cells. Cell culture media generally comprise an appropriate source of energy. A typical culture medium is composed of a complement of amino acids, vitamins, inorganic salts, glucose, and growth factors, hormones, and other factors. In addition to nutrients, the medium also helps maintain pH and osmolality.

The diluting medium may be any medium suitable for culturing macrophages. Since macrophages are immune cells that are a type of white blood cells, media that are suitable for culturing other types of immune cells (white blood cells) may also be applicable, for example media that are used to culture lymphoctyes such as T-lymphocytes may also be used to culture macrophages.

Suitable diluting medium may include any one or more of: TexMACS, X-Vivo 10, X-Vivo 15, AlMv, Plasma-Lyte or a mixture thereof.

Suitably the medium used for the dilution is suitable for culturing macrophages. Suitably the medium is a T-cell medium. Suitably the medium is selected from: TexMACS, X-Vivo 10, X-Vivo 15, AlMv, Plasma-Lyte Suitably the medium is GMP-compliant.

Suitably the medium is serum-free. Suitably the medium is animal substance-free (xeno-free).

Suitably the medium may be supplemented with factors. Suitable factors include growth factors, polysaccharides, cytokines and chemokines. Suitable factors may include: MCSF, IFNγ, IL10, IL4, IL13, TLR agonists such as LPS or poly(I:C). Recombinant versions may be provided for GMP compliance.

The inventors have found that supplementation with such factors is particularly useful when the macrophages have been stored in the freezer for about 3 months or more. In the Examples, rhMCSF (rhCSF-1) appear to help maintain viability during thawing when the cells were frozen for longer than 3 months.

In the diluting medium, these cytokines may be present at a concentration of 20 ng/mL, suitably within the range 10-100 mg/mL.

Suitably the medium contains a growth factor, suitably MCSF (macrophage colony stimulating factor) otherwise known as CSF-1. Suitably the MCSF may be recombinant MCSF, suitably recombinant human MCSF (rh-MCSF).

Suitably the medium contains MCSF at a concentration of between 50-150 ng/mL, suitably at a concentration of between 75-125 ng/mL, suitably at a concentration of 100 ng/mL (100 ng/mL equals $1.6 \times 10^4$ I U/m L).

Suitably the medium may be supplemented with polarisation factors. Suitably such factors stimulate the macrophages during thawing to develop into polarised macrophages. Suitably the medium may be supplemented with factors for M1-like polarisation or factors for M2-like polarisation.

Suitably the M1-like phenotype is pro-inflammatory.

Suitably the M2-like phenotype is pro-restorative.

Suitably the concentration of each polarising factor added to the medium is between 10-150 ng/mL, suitably between 25-125 ng/mL, suitably between 50-100 ng/mL. Suitably in order to produce M1-like macrophages, suitable M1 polarisation factors include: GM-CSF, IFNγ and TLR agonists such as LPS. Suitably the medium may contain at least IFNγ, or IFNγ+LPS.

Suitably the medium may contain M1 polarisation factors at a concentration of between 10-100 ng/mL, suitably at a concentration of between 20-80 mg/mL, suitably at a concentration of between 30 ng/mL to 60 ng/mL, suitably at a concentration of 50 ng/mL.

In one embodiment, the medium may contain IFNγ at a concentration of between 10-100 ng/mL, suitably at a concentration of between 20-80 mg/mL, suitably at a concentration of between 30 ng/mL to 60 ng/mL, suitably at a concentration of 50 ng/mL (equivalent to $0.1 \times 10^4$ IU/mL).

Suitably in order to produce M2-like macrophages, suitable M2 polarisation factors include: IL10, IL4, IL13 and poly(I:C). Suitably the medium may contain at least IL4 and IL13. Alternatively, the medium may contain only IL10. Alternatively, the medium may contain only poly(I:C).

Suitably the medium may contain M2 polarisation factors at a concentration of between 1-20 ng/mL, suitably at a concentration of between 5-15 mg/mL, suitably at a concentration of between 8 ng/mL to 12 ng/mL, suitably at a concentration of 10 ng/mL.

In one embodiment, the medium may contain IL4 and IL13 at a concentration of between 1-20 ng/mL, suitably at a concentration of between 5-15 mg/mL, suitably at a concentration of between 8 ng/mL to 12 ng/mL, suitably at a concentration of 10 ng/mL (equivalent to $0.29 \times 10^3$ IU/mL).

In another embodiment, the medium may contain IL10 at a concentration of between 1-20 ng/mL, suitably at a concentration of between 5-15 mg/mL, suitably at a concentration of between 8 ng/mL to 12 ng/mL, suitably at a concentration of 10 ng/mL (equivalent to $0.29 \times 10^3$ IU/mL).

Suitably the concentration of each M1 polarising factor is about 50 ng/mL. Suitably the concentration of each M2 polarising factor is about 10 ng/mL. Suitably during the polarisation step, further MCSF is added to the medium.

Suitably the further MCSF is added to the medium at a concentration of between 10-150 ng/mL, suitably at between 25-125 ng/mL, suitably between 50-100 ng/mL. Suitably the further MCSF is added to the medium at a concentration of about 50 ng/mL. Suitably 100 ng/mL of recombinant human MCSF GMP-graded=$1.6 \times 10^4$ IU/mL.

Suitably the one or more factors are added to the medium. Suitably the method of thawing cryopreserved macrophages may comprise a step of adding the one or more factors to the medium. Suitably adding the one or more factors to the medium may take place before the diluting step.

Suitably the macrophages are diluted in the medium by a ratio of between 1:2 to 1:20, suitably between 1:5 to 1:15, suitably between 1:8 to 1:12, suitably 1:10. Wherein the dilution ratio is the ratio of the volume of the initial (concentrated) solution to the volume of the final (dilute) solution.

Suitably the macrophages are diluted in the medium by a factor of between 2 to 20, suitably between 5 to 15, suitably between 8 to 12, suitably by a factor of 10.

In one embodiment, the cryopreserved macrophages are diluted in the medium by a factor of 10.

Macrophages The present invention relates to methods of cryopreserving and thawing macrophages.

Suitably the macrophages are monocyte-derived macrophages, suitably human monocyte-derived macrophages (hMDMs).

Suitably, in most embodiments the macrophages are unpolarised. Suitably the macrophages are mature. However, in some embodiments the macrophages may be polarised, suitably they may be M1-like or M2-like. Suitably the M1-like and the M2-like phenotype are generated by polarisation with various factors as explained above.

Suitably the M1-like phenotype is pro-inflammatory. Suitably the M2-like phenotype is pro-restorative. Suitably the macrophages, whether polarised or unpolarised, are GMP-compliant, suitably a composition or population comprising the macrophages is also GMP compliant.

Suitably the macrophages have been produced in vitro.

Suitably the method of cryopreserving macrophages of the invention may further comprise a step of obtaining macrophages. Suitably such a step takes place before step (a) of the method of cryopreserving macrophages. Suitably, the macrophages may be obtained from any suitable source.

Suitably this step may comprise producing macrophages in vitro. Suitably this step may comprise producing macrophages from monocytes in vitro.

Suitably, therefore, the method of cryopreserving macrophages of the invention may further comprise a step of obtaining monocytes.

Suitably the human monocytes are provided from any source such whole blood, mononuclear cells, leukapheresis or they may be iPSC-derived.

Suitably monocytes may be obtained from the blood of a subject. Suitably from a blood sample obtained from the subject. Suitably the monocytes may be obtained by isolating the monocytes from the blood of a subject. Suitably the monocytes may be obtained by isolating the monocytes from a blood sample obtained from a subject. Suitably the monocytes may be isolated from the buffy coat of blood. Suitably the monocytes may be obtained by isolating the monocytes from the buffy coat of a blood sample obtained from a subject. Suitably the monocytes may be isolated from the PBMC fraction of blood. Suitably the monocytes may be obtained by isolating the monocytes from the PBMC fraction of a blood sample obtained from a subject. Suitable methods to isolate monocytes from blood samples are known in the art.

Suitably monocytes may be obtained from peripheral blood or leukapheresis collection. Suitably from human blood, suitably a human blood sample. Suitably the monocytes are obtained from the mononuclear leukocyte fraction of human blood, suitably from the mononuclear leukocyte fraction of a human blood sample.

Suitably the methods may further comprise a step of purifying monocytes from blood, suitably from the mononuclear leukocyte fraction of blood, suitably from the mononuclear leukocyte fraction of a human blood sample. Such purification may comprise isolation of the mononuclear leukocyte fraction, and isolation of purified monocytes from the fraction using specific (markers of monocyte lineage) or non-specific (adherence) methods. Suitably isolation of the mononuclear leukocyte fraction may be carried out by various methods depending upon source material. Suitably isolation of selected purified monocytes may be carried out at small scale (magnetic bead column devices or plastic adherence) or at larger scale for manufacturing using relevant devices such as the CliniMACS Prodigy system (Miltenyi Biotec).

Suitably therefore, the method of cryopreservation of the invention may comprise a step of obtaining monocytes from a sample of blood. Suitably therefore, the method of cryopreservation of the invention may comprise a step of obtaining monocytes from a sample of human blood. Suitably therefore, the method of cryopreservation of the invention may comprise a step of isolating monocytes from a sample of blood. Suitably therefore, the method of cryopreservation of the invention may comprise a step of isolating monocytes from a sample of human blood.

Suitably the monocytes are isolated from whole blood or other cell source as above, suitably by enrichment. Suitably isolation of mononuclear cell fractions may be carried out by density centrifugation or microfluidic separation of the source material. Suitably isolation of purified monocytes may be carried out by filtration of the mononuclear cell fraction, such as for example magnetic bead to a surface marker specific for monocytes with column filtration, suitable filtration systems include the CliniMACS Prodigy system (Miltenyi Biotec). Suitably isolation of purified monocytes may be carried out by CD14 microbead selection.

Suitably the method of cryopreservation of the invention may further comprise a step of converting monocytes to macrophages. Suitably a step of converting monocytes obtained from a sample of blood into macrophages.

Suitably any method of culturing may be used to convert the monocytes into macrophages. Suitable such culturing methods are discussed below.

Suitably the monocytes may be obtained from a human subject. Suitably from an adult human subject. Suitably the monocytes may be obtained from a healthy or a diseased subject. In one embodiment, the monocytes may be obtained from a diseased subject in order to provide cryopreserved macrophages from a particular disease state or stage.

Suitably the monocytes may be obtained from a peripheral blood or leukapheresis donation from a healthy subject or a diseased subject. Suitably therefore the monocytes may be allogeneic or autologous to the subject. Suitably allogeneic monocytes are obtained from a peripheral blood or leukapheresis donation of a healthy subject. Suitably the healthy subject is blood-group matched to the subject to be treated. Suitably the healthy subject is partially HLA matched to the subject to treat. Suitably the healthy subject is H LA-matched to the subject to be treated.

Suitably, to minimise immune reactions during treatment, the monocytes are derived from a peripheral blood or leukapheresis donation from the diseased subject who is to be treated with the resulting macrophages. In one embodiment, therefore, the monocytes are autologous to subject to be treated. Suitably therefore, the resulting macrophages produced from the monocytes may be autologous.

Suitably the monocytes may be obtained from a subject having a disease. In one embodiment, the subject may have a liver disease. Examples of liver diseases are discussed elsewhere herein. Suitably the liver disease may be cirrhosis.

Suitably, to ensure supply of monocytes for the methods of the invention, the monocytes are derived from peripheral blood or leukapheresis donation from a healthy subject. In one embodiment, therefore, the monocytes are allogeneic to the subject to be treated. Suitably therefore, the resulting macrophages produced from the monocytes may be allogeneic.

Suitably the monocytes are positive for the expression of the following surface markers—CD14, CD45 and CD192 (CCR2). Suitably the isolated monocytes have low expression of surface marker 25F9 (or the identified molecule recognised by this antibody) and CD206. Suitably the monocytes have high expression of CCR2.

As stated above, the method of cryopreserving macrophages of the invention may further comprise a step of producing macrophages in vitro.

Suitably the macrophages may be produced by an in vitro method. Suitably from progenitor cells such as monocytes (as described above) alternatively from stem cells, inducible pluripotent stem cells and the like. Suitable methods for production of macrophages in vitro are known in the art.

Suitably the macrophages are produced in vitro from monocytes by a culturing method lasting between 3 to 8 days, optionally 4 to 8 days. Suitably the macrophages are produced in vitro from monocytes by a culturing method lasting between 3 to 7 days, optionally 4 to 7 days, further optionally 5 to 7 days. In one embodiment, the macrophages are produced in vitro from monocytes by a culturing method that lasts 3 days, 4 days, 5 days or 7 days, known as a 5 day method or a 7 day method respectively. One example of an in vitro method of producing macrophages from monocytes is described in WO2019/175595.

In one embodiment, the macrophages are produced by a 'day5' method comprising:

(a) Culturing monocytes in medium for 4-5 days to produce macrophages, wherein the medium comprises one or more growth factors to stimulate macrophage production;

Wherein step (a) takes place entirely in the same medium.

In one embodiment, the macrophages are produced by a 'day5' method comprising:

(a) Culturing monocytes in medium for 3-6 days to produce macrophages, wherein the medium comprises one or more growth factors to stimulate macrophage production;

Wherein step (a) takes place entirely in the same medium.

Suitably the medium comprises one or more growth factors selected from the CSF family, preferably M-CSF.

Suitably the medium contains MCSF at a concentration of between 25-150 ng/mL.

Suitably the medium may be one of those described herein above.

Suitably, the macrophages are produced from human progenitor cells. Suitably from monocytes, suitably human monocytes. Suitably therefore, producing macrophages in vitro comprises culturing progenitor cells. Suitably therefore producing macrophages in vitro comprises culturing human progenitor cells. Suitably therefore producing macrophages in vitro comprises culturing human monocytes.

In one embodiment, producing macrophages in vitro comprises culturing human monocytes for 3, 4 or 5 days.

Suitably therefore, the method of cryopreservation of the invention may comprise a step of culturing monocytes in vitro to produce macrophages. Suitably therefore, the method of cryopreservation of the invention may comprise a step of culturing human monocytes in vitro to produce macrophages.

Suitably therefore, the method of cryopreservation of the invention may comprise a step of culturing human monocytes in vitro to produce macrophages for a period of between 3-8 days, optionally 4-8 days, suitably 5 days.

Suitably, the method of cryopreservation may further comprise a step of polarizing the macrophages. Suitably such polarization may be carried out on macrophages obtained from any source. In one embodiment, the method of cryopreservation comprises a first step of obtaining macrophages, and a second step of polarization of the macrophages.

Suitably therefore the method may comprise a first step of obtaining the macrophages as described above, and a second step of polarizing the macrophages. Suitably polarizing the macrophages also takes place prior to step (a) of the method of cryopreserving macrophages.

Suitable methods of polarizing macrophages are known in the art. Suitably the macrophages are polarized by an in vitro method. Suitably into M1-like or M2-like phenotypes. Suitably therefore, the method of cryopreservation comprises a step of in vitro polarization of macrophages into an M1-like or M2-like phenotype. Suitable factors for polarizing macrophages are described elsewhere herein.

Suitably the method of cryopreserving macrophages of the invention may further comprise a step of obtaining macrophages. Suitably such a step takes place before step (a) of the method of cryopreserving macrophages. Suitably, the macrophages may be obtained from any suitable source, including deriving the macrophages from pluripotent stem cells, optionally induced pluripotent stem cells (iPSC). Such cells may be differentiated to macrophages using appropriate growth factors, which are preferably GMP compliant, xeno- and serum-free methods.

Suitably the method of cryopreserving macrophages of the invention may further comprise a step of transfecting the obtained macrophages prior to cryopreservation. The macrophage in this embodiment may be a macrophage obtained in any particular method as described herein, including isolation from a subject or derived from a progenitor or stem cell. Suitably, the cells may be transfected and then subjected to the freezing methods of the invention. The cells may be transfected after the "day5" method described herein, notably after 3, 4 or 5 days of culturing from monocytes to macrophages. The transfected cells may then be cryopreserved according to the methods of the present invention. Optionally, the cells are cultured at 37° C. for at least 12 hours, at least 18 hours, at least 24 hours, at least 30 hours or at least 36 hours prior to cryopreservation. Suitable transfection methods are described in co-pending application no. PCT/GB2021/051300.

Cryopreserved Macrophages

The present invention also provides for the cryopreserved macrophages produced by the methods of the invention.

In some embodiments, the method of cryopreservation may be a method of cryopreservation of polarised macrophages, suitably M1-like or M2-like macrophages. References to macrophages in this section include polarized macrophages.

Suitably, the macrophages produced by the cryopreservation method of the invention are novel by virtue of the method. Suitably in addition, the macrophages produced by the method are in themselves novel by virtue of their properties, in particular their high viability.

Suitably the cryopreserved macrophages are GMP compliant, suitably a composition or population comprising the cryopreserved macrophages is also GMP compliant.

Suitably the cryopreserved macrophages are mature macrophages. Suitably the cryopreserved macrophages express the expected mature macrophage cell surface markers. Suitably the cryopreserved macrophages of the invention are CD14+, CD206+, CD163+, CD169+, 25F9+, and CD86+. Suitably the cryopreserved macrophages are CCR2−.

Suitably the cryopreserved macrophages have a high viability of at least 60%, at least 62%, at least 64%, at least 66%, at least 68%, at least 70%, at least 72%, at least 74%, at least 76%, at least 78%, at least 80%, at least 82%, at least 84%, at least 86%, at least 88%, at least 90%.

In one embodiment, the cryopreserved macrophages have a viability of between 70 to 100%, suitably between 80-100%. Advantageously this viability is much higher than macrophages preserved by other cryopreservation methods.

In one embodiment, the cryopreserved macrophages have a viability of at least 80%.

Suitably the yield of the cryopreserved macrophages is at least 60%, at least 62%, at least 64%, at least 66%, at least 68%, at least 70%, at least 72%, at least 74%, at least 76%, at least 78%, least 80%, at least 82%, at least 84% at least 86%, at least 88%, at least 90%, at least 92%, at least 94%, at least 96%, at least 98%.

In one embodiment, the yield of the cryopreserved macrophages is between 70-100%. Advantageously this yield is much higher than other cryopreservation methods.

Suitably the cryopreserved macrophages of the invention have good phagocytic capacity. Suitably the cryopreserved macrophages of the invention have a phagocytic capacity of at least 10%, at least 11%, at least 12%, at least 13%, at least 14%, at least 15%, at least 16%, at least 17%, at least 18%, at least 19%, at least 20%.

Suitably the phagocytic capacity is measured by pHrodo bead analysis. Suitably the phagocytic capacity is measured by incubating the macrophages with pH sensitive fluorescent beads for 1 hour and measuring the emitted fluorescence as described in the Examples. In the Examples, the numbers reported are for a 1 hour phagocytosis determination, wherein the phagocytic target is beads coated with a pathogen such as *E. coli*.

Thawed Macrophages

The present invention also provides for the thawed macrophages produced by the methods of the invention.

In some embodiments, the method of thawing may be a method of thawing cryopreserved polarised macrophages, suitably M1-like or M2-like macrophages. References to macrophages in this section include polarised macrophages.

Suitably, the macrophages produced by the thawing method of the invention are novel by virtue of the method. Suitably in addition, the macrophages produced by the method are in themselves novel by virtue of their properties, in particular their high viability.

Suitably the thawed macrophages are GMP compliant, suitably a composition or population comprising the thawed macrophages is also GMP compliant.

Suitably the thawed macrophages are mature macrophages. Suitably the thawed macrophages express the expected mature macrophage cell surface markers. Suitably the thawed macrophages of the invention are CD14+, CD206+, CD163+, CD169+, 25F9+, and CD86+. Suitably the thawed macrophages are CCR2−. Suitably such cell surface markers are expressed by thawed macrophages a period of time after thawing, suitably around 12-16 hours after thawing.

Suitably the thawed macrophages have a viability of at least 60%, at least 62%, at least 64%, at least 66%, at least 68%, at least 70%, at least 72%, at least 74%, at least 76%, at least 78%, at least 80%, at least 82%, at least 84%, at least 86%, at least 88%, at least 90%.

In one embodiment, the thawed macrophages have a viability of between 80 to 100%. Advantageously this viability is much higher than macrophages thawed by other methods.

Suitably the yield of the thawed macrophages is at least 60%, at least 62%, at least 64%, at least 66%, at least 68%, at least 70%, at least 72%, at least 74%, at least 76%, at least 78%, least 80%, at least 82%, at least 84% at least 86%, at least 88%, at least 90%, at least 92%, at least 94%, at least 96%, at least 98%.

In one embodiment, the yield of the thawed macrophages is between 70-100%. Advantageously this yield is much higher than other thawing methods.

Suitably the thawed macrophages of the invention have good phagocytic capacity. Suitably the thawed macrophages of the invention have a phagocytosis level of at least 10%, at least 11%, at least 12%, at least 13%, at least 14%, at least 15%, at least 16%, at least 17%, at least 18%, at least 19%, at least 20%. Such figures are in relation to a 1 hour phagocytosis determination, wherein the phagocytic target is beads coated with a pathogen such as *E. coli*.

Suitable uses of the cryopreserved and/or thawed macrophages of the invention:

Suitable diseases which may be treated using either the cryopreserved macrophages of the present invention or the thawed macrophages of the present invention, or indeed the macrophages prepared by using the cryopreservation and thawing techniques described herein:

Suitably the cryopreserved and/or thawed macrophages of the invention may be used in cell therapy. Suitably the cryopreserved and/or thawed macrophages of the invention may be used in the treatment of diseases. Suitably the cryopreserved and/or thawed macrophages of the invention may be used in the treatment of diseases by reducing fibrosis, and reducing inflammation. Suitably the cryopreserved and/or thawed macrophages of the invention may be used in the treatment of liver diseases. Suitably the cryopreserved and/or thawed macrophages of the invention may be used in the treatment of liver diseases by reducing fibrosis and reducing inflammation.

Suitably therefore macrophages may be for use in the treatment of fibrotic or inflammatory diseases, suitably for use in the treatment of diseases which involve fibrosis and/or inflammation. Suitably the cryopreserved macrophages may be for use in the treatment of a disease by reducing fibrosis and/or by reducing inflammation.

Suitably the macrophages may be for use in the treatment of any inflammatory disease, or any fibrotic disease.

Suitably the macrophages may be for use in the treatment of any liver disease, kidney disease, lung disease, or muscle disease. Suitably the macrophages may be for use in the treatment of any fibrotic disease or inflammatory disease in the liver, kidney, lung, or muscle. Suitably the transfected macrophages may be for use in the treatment of any fibrotic disease or inflammatory disease in the liver.

Suitably the macrophages may be for use in the treatment of a fibrotic liver disease, fibrotic kidney disease, fibrotic lung disease, or fibrotic muscle disease. Suitably the macrophages may be for use in the treatment of inflammatory liver diseases, inflammatory kidney diseases, inflammatory lung diseases, or inflammatory muscle diseases. Suitably the macrophages may be for use in the treatment of liver diseases, kidney disease, lung diseases, or muscle diseases, by reducing fibrosis and/or inflammation. Suitably the macrophages may be for use in the treatment of fibrotic liver diseases or inflammatory liver diseases. Suitably the macrophages may be for use in the treatment of liver diseases by reducing fibrosis and/or reducing inflammation.

Suitable liver diseases include: chronic liver disease, acute liver disease, acute-on-chronic liver disease, Alagille Syndrome, Alcohol-Related Liver Disease, acute fatty liver of pregnancy, Alpha-1 Antitrypsin Deficiency, Autoimmune Hepatitis, Benign Liver Tumours, Biliary Atresia, Budd Chiari syndrome, Cirrhosis, Crigler-Najjar Syndrome, Cystic fibrosis related liver disease, Gallstones, Galactosemia, Gilbert Syndrome, Hemochromatosis, Hepatic Encephalopathy, Hepatitis A, Hepatitis B, Hepatitis C, Hepatitis E, Hepatorenal Syndrome, Intrahepatic Cholestasis of Pregnancy (ICP), Lysosomal Acid Lipase Deficiency (LAL-D), Liver Cysts, Liver abscesses, Liver Cancer, Newborn Jaundice, Non-Alcoholic Fatty Liver Disease, Non-Alcoholic Steatohepatitis, Primary Biliary Cholangitis (PBC), Porphyria, Portal hypertension, Primary Sclerosing Cholangitis (PSC), Progressive Familial Intrahepatic Cholestasis (PFIC), Reye Syndrome, Type I Glycogen Storage Disease, Wilson Disease.

Suitably lung diseases include: chronic lung disease, acute lung disease, acute-on-chronic lung disease, asthma, COPD, pneumonia, emphysema, pulmonary fibrosis, lung cancer, mesothelioma, cystic fibrosis, tuberculosis, respiratory infections, pulmonary edema, bronchitis, pulmonary embolism, pulmonary hypertension, sarcoidosis, interstitial lung disease, Langerhans cell histiocytosis, bronchiolitis obliterans, post inflammatory pulmonary fibrosis, pulmonary alveolar proteinosis, idiopathic pulmonary hemosiderosis, pulmonary alveolar microlithiasis, idiopathic interstitial pneumonia, idiopathic pulmonary fibrosis, acute interstitial pneumonitis, cryptogenic organising pneumonia, desquamative interstitial pneumonia, lymphangioleiomyomatosis, neuroendocrine cell hyperplasia, pulmonary interstitial glycogenosis, alveolar dysplasia, rheumatoid lung disease, cytokine release syndrome (CRS)—induced acute respiratory distress syndrome (ARDS) and secondary hernophagocytic iymphohistiocytosis (sHLH) and COViD-induced fibrosis.

Suitable kidney diseases include: chronic kidney disease, acute kidney disease, acute-on-chronic kidney disease, Abderhalden—Kaufmann—Lignac syndrome (Nephropathic Cystinosis), Acute Kidney Failure/Acute Kidney Injury, Acute Lobar Nephronia, Acute Phosphate Nephropathy, Acute Tubular Necrosis, Adenine Phosphoribosyltransferase Deficiency, Apparent Mineralocorticoid Excess Syndrome, Arteriovenous Malformations and Fistulas of the Urologic Tract, Autosomal Dominant Hypocalcemia, Bardet-Biedl Syndrome, Bartter Syndrome, Beer Potomania, Beeturia, β-Thalassemia Renal Disease, Bile Cast Nephropathy, Birt-Hogg-Dube Syndrome, C1q Nephropathy, C3 Glomerulopathy C3 Glomerulopathy with Monoclonal Gammopathy, C4 Glomerulopathy, CAKUT (Congenital Anomalies of the Kidney and Urologic Tract), Capillary Leak Syndrome, Cardiorenal syndrome, CFHR5 nephropathy, Charcot—Marie—Tooth Disease with Glomerulopathy, Churg—Strauss syndrome, Chyluria, Ciliopathy, Cold Diuresis, Collagenofibrotic Glomerulopathy, Collapsing Glomerulopathy, Congenital Anomalies of the Kidney and Urinary Tract (CAKUT), Congenital Nephrotic Syndrome, Congestive Renal Failure, Conorenal syndrome (Mainzer-Saldino Syndrome or Saldino-Mainzer Disease), Contrast Nephropathy, Cortical Necrosis, Cryocrystalglobulinemia, Cryoglobuinemia, Crystal-Storing Histiocytosis, Cystinuria, Dense Deposit Disease (MPGN Type 2), Dent Disease (X-linked Recessive Nephrolithiasis), Dialysis Disequilibrium Syndrome, Diabetes and Diabetic Kidney Disease, Diuresis, Drug and substance induced kidney disease, EAST syndrome, Ectopic Kidney, Erdheim-Chester Disease, Fabry's Disease, Familial Hypocalciuric Hypercalcemia, Fanconi Syndrome, Fraser syndrome, Fibrillary Glomerulonephritis and Immunotactoid Glomerulopathy, Fraley syndrome, Hypervolemia, Focal Segmental Glomerulosclerosis, Focal Glomerulosclerosis, Galloway Mowat syndrome, Hypertension, Gitelman Syndrome, Glomerular Diseases, Glomerular Tubular Reflux, Glycosuria, Goodpasture Syndrome, HANAC Syndrome, Heat Stress Nephropathy, Hemolytic Uremic Syndrome (HUS), Atypical Hemolytic Uremic Syndrome (aHUS), Hemophagocytic Syndrome, Hemorrhagic Cystitis, Nephropathis Epidemica), Hemosiderinuria, Hemosiderosis related to Paroxysmal Nocturnal Hemoglobinuria and Hemolytic Anemia, Hepatic Glomerulopathy, Hepatic Veno-Occlusive Disease, Sinusoidal Obstruction Syndrome, Hepatitis C-Associated Renal Disease, Hepatocyte Nuclear Factor 1β—Associated Kidney Disease, Hepatorenal Syndrome, HNF1B-related Autosomal Dominant Tubulointerstitial Kidney Disease, Horseshoe Kidney (Renal Fusion), Hunner's Ulcer, Hydrophilic Polymer Emboli, Hyperaldosteronism, Hypercalcemia, Hyperkalemia, Hypermagnesemia, Hypernatremia, Hyperoxaluria, Hyperphosphatemia, Hypocalcemia, Hypocomplementemic Urticarial Vasculitic Syndrome, Hypokalemia-induced renal dysfunction, Hypomagnesemia, Hyponatremia, Hypophosphatemia, Interstitial Nephritis, Infection induced kidney disease, Ivemark's syndrome, Joubert Syndrome, Kidney Stones, Nephrolithiasis, Kidney cancer, Lecithin Cholesterol Acyltransferase Deficiency (LCAT Deficiency), Liddle Syndrome, Lightwood-Albright Syndrome, Lipoprotein Glomerulopathy, Lupus, Systemic Lupus Erythematosis, Lysinuric Protein Intolerance, Lysozyme Nephropathy, Malignancy-Associated Renal Disease, Malakoplakia, McKittrick-Wheelock Syndrome, Meatal Stenosis, Medullary Cystic Kidney Disease, Urolodulin-Associated Nephropathy, Juvenile Hyperuricemic Nephropathy Type 1, Medullary Sponge Kidney, MELAS Syndrome, Membranoproliferative Glomerulonephritis, Membranous Nephropathy, MesoAmerican Nephropathy, Metabolic Acidosis, Metabolic Alkalosis, Microscopic Polyangiitis, Milk-alkalai syndrome, Dysproteinemia, MUC1 Nephropathy, Multicystic dysplastic kidney, Multiple Myeloma, Myeloproliferative Neoplasms and Glomerulopathy, Nail-patella Syndrome, NARP Syndrome, Nephrocalcinosis, Nephrocystin-1 Gene Deletions and ESRD, Nephrogenic Systemic Fibrosis, Nephronophthisis due to Nephrocystin-1 Gene Deletions, Nephroptosis (Floating Kidney, Renal Ptosis), Nephrotic Syndrome, Nodular Glomerulosclerosis, Nutcracker syndrome, Oligomeganephronia, Orotic Aciduria, Oxalate Nephropathy, Page Kidney, Papillary Necrosis, Papillorenal Syndrome (Renal-Coloboma Syndrome, Isolated Renal Hypoplasia), The Peritoneal-Renal Syndrome, POEMS Syndrome, Podocyte Infolding Glomerulopathy, Post-infectious Glomerulonephritis, Polyarteritis Nodosa, Polycystic Kidney Disease, Posterior Urethral Valves, Post-Obstructive Diuresis, Proliferative Glomerulonephritis with Monoclonal IgG Deposits (Nasr Disease), Proteinuria (Protein in Urine), Pseudohyperaldosteronism, Pseudohypobicarbonatemia, Pseudohypoparathyroidism, Pulmonary-Renal Syndrome, Pyelonephritis (Kidney Infection), Pyonephrosis, Reflux Nephropathy, Rapidly Progressive Glomerulonephritis, Renal Abscess, Peripnephric Abscess, Renal Agenesis, Renal Arcuate Vein Microthrombi-Associated Acute Kidney Injury, Renal Artery Aneurysm, Renal Artery Stenosis, Renal Cell Cancer, Renal Cyst, Renal Infarction, Renal Osteodystrophy, Renal Tubular Acidosis, Retroperitoneal Fibrosis, Rhabdomyolysis, Rheumatoid Arthritis-Associated Renal Disease, Sarcoidosis Renal Disease, Salt Wasting, Scleroderma Renal Crisis, Serpentine Fibula-Polycystic Kidney Syndrome, Exner Syndrome, Sickle Cell Nephropathy, TAFRO Syndrome, Tea and Toast Hyponatremia, Thin Basement Membrane Disease, Benign Familial Hematuria, Thrombotic Microangiopathy Associated with Monoclonal Gammopathy, Trench Nephritis, Trigonitis, Tuberculosis, Genitourinary, Tuberous Sclerosis, Tubular Dysgenesis, Immune Complex Tubulointerstitial Nephritis Due to Autoantibodies to the Proximal Tubule Brush Border, Tumour Lysis Syndrome, Uremia, Uremic Optic Neuropathy, Ureteritis Cystica, Ureterocele, Urethral Caruncle, Urethral Stricture, Urinary Tract Infection, Urogenital Fistula, Uromodulin-Associated Kidney Disease, Vasomotor Nephropathy, Vesicointestinal Fistula, Vesicoureteral Reflux, VGEF Inhibition and Renal Thrombotic Microangiopathy, viral induced kidney disease, Von Hippel-Lindau Disease, Waldenstrom's Macroglobulinemic Glomerulonephritis, Wegener's Granulomatosis, Granulomatosis with Polyangiitis, Wunderlich syndrome, Zellweger Syndrome, Cerebrohepatorenal Syndrome.

Suitable muscle diseases include: chronic muscle diseases, acute muscle diseases, acute-on-chronic muscle diseases, muscular dystrophies (e.g. Duchenne muscular dystrophy, limb girdle muscular dystrophies), idiopathic inflammatory myopathies (e.g. Dermatomyositis, Polymyositis), Myasthenia gravis, Amyotrophic Lateral Syndrome, Mitochondrial myopathies, Rhabdomyolysis, Fibromyalgia, sprains and strains, and Muscle tumours, such as leiomyomas, rhabdomyomas, and rhabdomyosarcomas.

Suitably the disease or injury may be chronic or acute or may be acute-on-chronic. Suitably an acute disease or injury may be classed as a disease or injury with an onset of less than 24 weeks from cause. Suitably a chronic disease may be classed as a disease or injury which has persisted for more than 6 months. Suitably an 'acute-on-chronic' disease or injury may be classed as a disease or injury with an onset of less than 24 weeks from cause, which occurs in a subject already having a chronic disease.

Suitably a chronic liver disease/injury may be selected from the following: hepatitis C; hepatitis B; alcohol related liver disease; non-alcoholic fatty liver disease; cryptogenic cirrhosis; Wilson's disease; autoimmune hepatitis; cholangitis; hemochromatosis; and alpha-1-antitrypsin deficiency.

Suitably an acute liver disease/injury may be caused by the following: excessive alcohol consumption; adverse reaction to medications; poisoning for example by food, chemicals, toxins; infection with microorganisms such as cytomegalovirus, Epstein Barr virus, yellow fever; acute fatty liver of pregnancy; and drug overdose, for example acetaminophen overdose (APAP).

Suitably, the cryopreserved and/or thawed macrophages may be for use in the treatment of acute, chronic or acute-on chronic liver disease.

Suitably the cryopreserved and/or thawed macrophages are for use in the treatment of liver disease or injury by reducing fibrosis and/or inflammation in a chronic liver disease. Suitably the cryopreserved or thawed macrophages are for use in the in the treatment of chronic liver disease by reducing fibrosis and/or inflammation.

In one embodiment, the cryopreserved and/or thawed macrophages of the invention are for use in the treatment of liver cirrhosis. In one embodiment, the macrophages of the invention are for use in the treatment of APAP overdose.

The invention will now be described with reference to the accompanying figures and examples in which:

FIG. 1 shows a test of various cryopreservation conditions for hMDMs from day5 (D5) and day7 (D7) methods of in vitro production; A Experimental design: GMP-graded hMDMs D5 and D7 are diluted at distinct concentration in Alburex (Alb)+20% DMSO. After 30' or 60' of cool down at 4° C., hMDMs are frozen at –80° C. After two weeks cells are thawed, diluted in TexMACS and spun before being counted and analysed by flow cytometry (FC) to establish viability; B Flow cytometry analysis of cell viability of hMDMs D5 and D7 subjected to 30 mins cool down time before freezing. Each symbol represents a donor. Distinct patterns identify distinct concentrations at freezing (empty circle=1×10$^6$/mL; double diagonal line=5×10$^6$/mL; single diagonal line=10×10$^6$/mL). The dashed line represents the minimal acceptable viability for clinical use; C Flow cytometry analysis of cell viability of hMDMs D5 and D7 subjected to 60 mins cool down time before freezing. Each symbol represents a donor. Distinct patterns identify distinct concentrations at freezing (empty dot=1×10$^6$/mL; double diagonal line=5×10$^6$/mL; single diagonal line=10×10$^6$/mL). The dashed line represents the minimal acceptable viability for clinical use; D Automated counter analysis of cell numbers of hMDMs D5 and D7 subjected to 30 mins cool down time before freezing. Each symbol represents a donor. Distinct patterns identify distinct concentrations at freezing (empty dot=1×10$^6$/mL; double diagonal line=5×10$^6$/mL; single diagonal line=10×10$^6$/mL); E Automated counter analysis of cell numbers of hMDMs D5 and D7 subjected to 60 mins cool down time before freezing. Each symbol represents a donor. Distinct patterns identify distinct concentrations at freezing (empty dot=1×10$^6$/mL; double diagonal line=5×10$^6$/mL; single diagonal line=10×10$^6$/mL); F Experimental design: GMP-graded hMDMs D5 and D7 are diluted at distinct concentration in Alburex (Alb)+20% DMSO. After 30 min or 60 min of cool down at 4° C., hMDMs are frozen at –80° C. After two weeks cells are thawed, diluted in TexMACS and left in incubator for 2 h before being counted and analysed by flow cytometry (FC) to establish viability; G Flow cytometry analysis of cell viability of hMDMs D5 and D7 subjected to 30 min and 60 min cool down time before freezing. Each symbol represents a donor. Distinct patterns identify distinct concentrations at freezing (double diagonal line=5×10$^6$/mL; single diagonal line left to right=10×10$^6$/mL; single diagonal line right to left=20×10$^6$/mL). The dashed line represents the minimal acceptable viability for clinical use; H Automated counter analysis of cell numbers of hMDMs D5 and D7 subjected to 30 min and 60 min cool down time before freezing. Each symbolrepresents a donor. Distinct patterns identify distinct concentrations at freezing (double diagonal line=5×10$^6$/mL; single diagonal line left to right=10×10$^6$/mL; single diagonal line right to left=20×10$^6$/mL).

Figure 2:
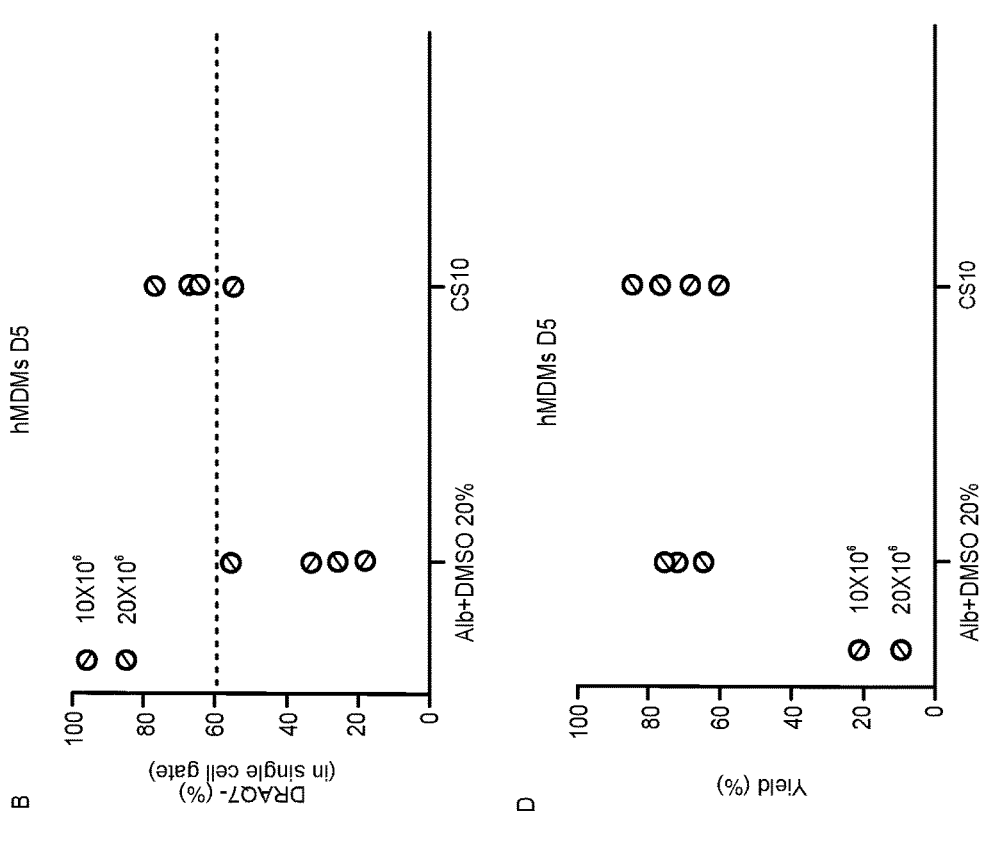
Figure 2:
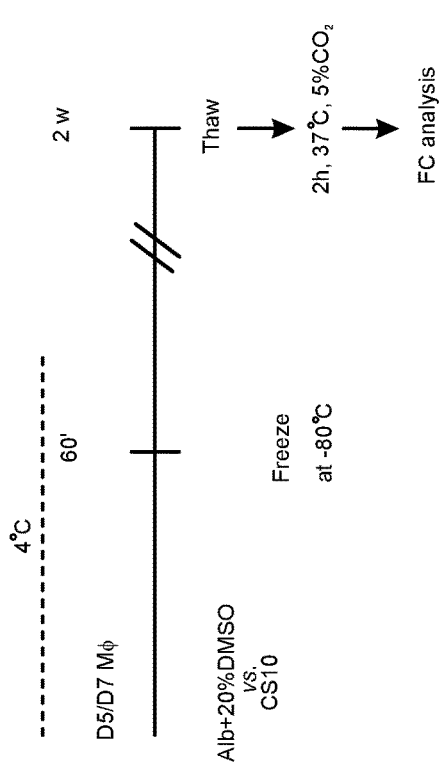
Figure 2:
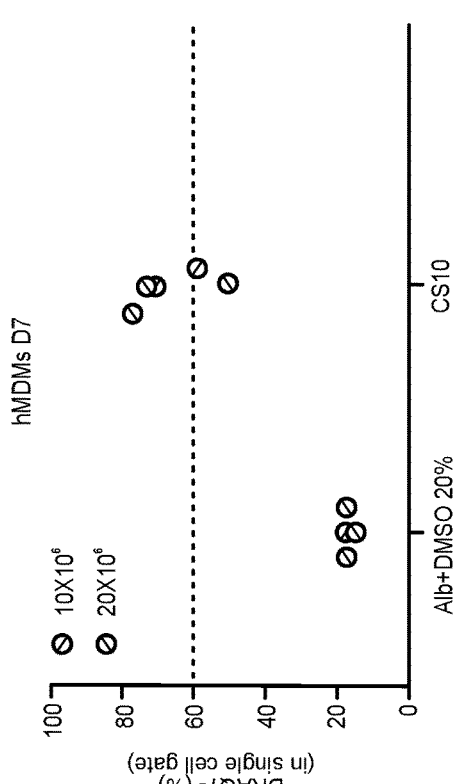
Figure 2:
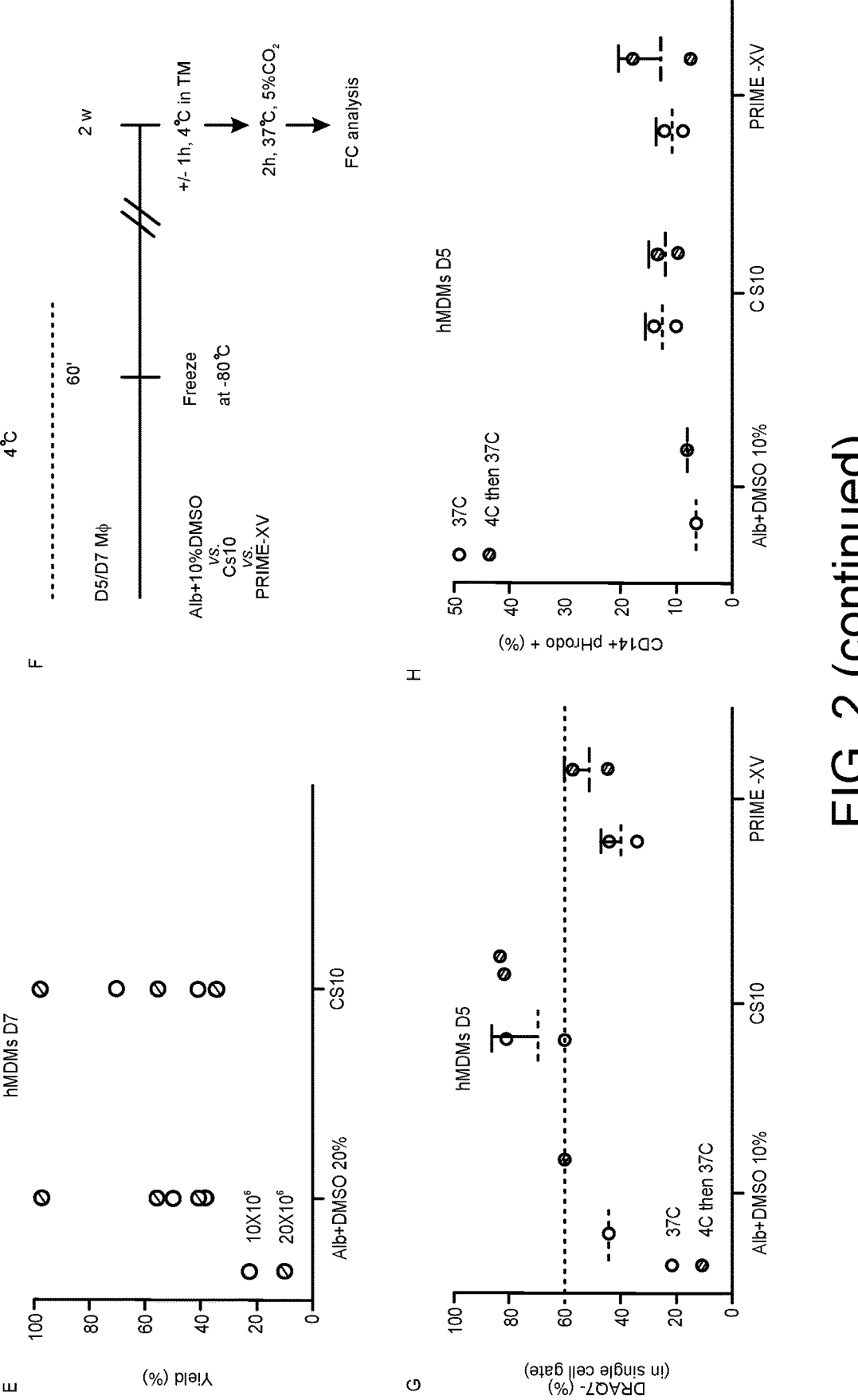
Figure 2:
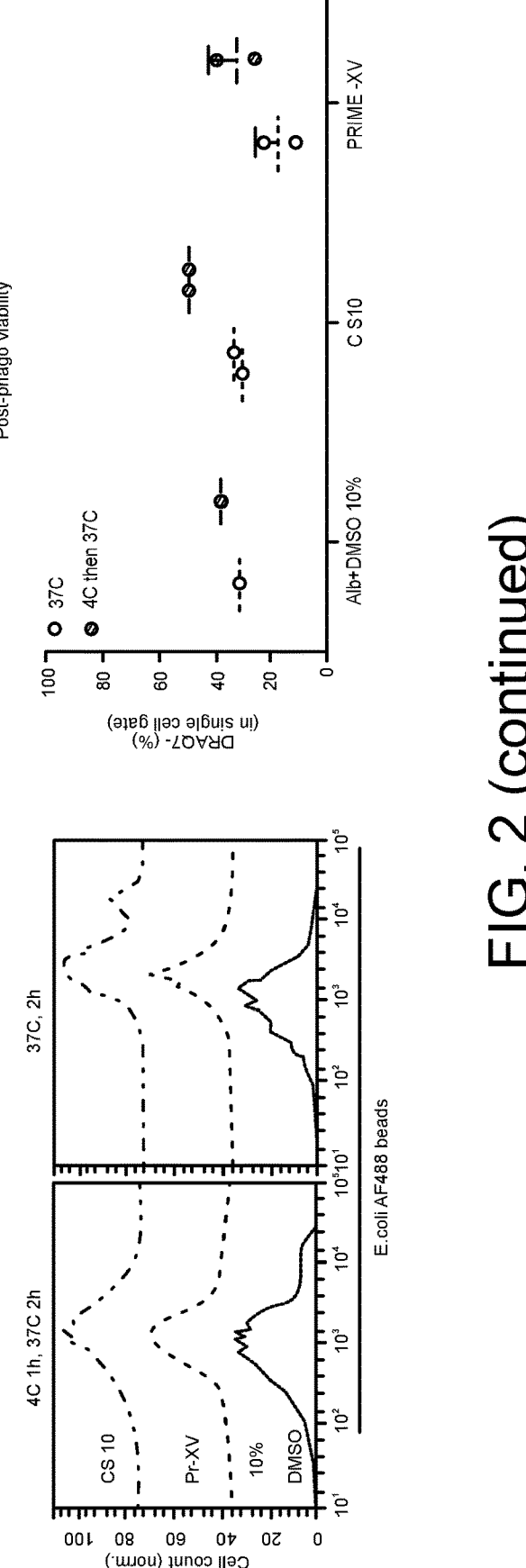

FIG. 2 shows further testing of various cryopreservation conditions for hMDMs day 5 (D5) and day7 (D7) methods of in vitro production; A Experimental design: GMP-graded hMDMs D5 and D7 are diluted at distinct concentration in Alburex (Alb)+20% DMSO or CS10 (CryoStore 10). After 60' of cool down at 4° C., hMDMs are frozen at –80° C. After two weeks cells are thawed, diluted in TexMACS and incubated for 2 h at 37° C., 5% CO$_2$, before being counted and analysed by flow cytometry (FC) to establish viability; B Flow cytometry analysis of cell viability of hMDMs D5 subjected to 60 min cool down time before freezing. Each symbol represents a donor. Distinct patterns identify distinct concentrations at freezing (single diagonal line left to right=10×10$^6$/mL; single diagonal line right to left=20×10$^6$/mL). The dashed line marks our minimal intended goal for viability for clinical use; C Flow cytometry analysis of cell viability of hMDMs D7 subjected to 60 min cool down time before freezing. Each symbol represents a donor. Distinct patterns identify distinct concentrations at freezing (single diagonal line left to right=10×10$^6$/mL; single diagonal line right to left=20×10$^6$/mL). The dashed line marks our minimal intended goal for viability for clinical use; D Automated counter analysis of cell numbers of hMDMs D5 subjected to 60 min cool down time before freezing. Each symbol represents a donor. Distinct patterns identify distinct concentrations at freezing (single diagonal line left to right=10×10$^6$/mL; single diagonal line right to left=20×10$^6$/mL); E Automated counter analysis of cell numbers of hMDMs D7 subjected to 60 min cool down time before freezing. Each symbol represents a donor. Distinct patterns identify distinct concentrations at freezing (single diagonal line left to right=10×10$^6$/mL; single diagonal line right to left=20×10$^6$/mL); F Experimental design: GMP-graded hMDMs D5 are diluted at distinct concentration in Alburex (Alb)+10% DMSO or CS10 (CryoStore 10) or Prime-XV (DMSO-free medium). After 60 mins of cool down at 4° C., hMDMs are frozen at –80° C. After two weeks cells are thawed, diluted in TexMACS and incubated or not for 1 h at 4° C., before being incubated for 2 h at 37° C., 5% CO$_2$; G hMDMs are then counted and analysed by flow cytometry (FC) to establish viability. Each symbol represents a donor. Distinct patterns identify distinct thawing protocols (double right to left stripe=37 C.; double right to left stripe=4° C. then 37° C.); H Phagocytosis analysis of hMDMs D5 incubated or not for 1 h at 4° C., before being incubated for 2 h at 37° C., 5% CO2 at thawing. Each symbol represents a donor. Distinct patterns identify distinct thawing protocols (double right to left stripe=37 C.; double right to left stripe=4° C. then 37° C.); I Histogram plots representative of the various freezing and thawing conditions. On the x axis we report the MFI of the pHrodo beads calculated in the gate of phagocytosing macrophages; J Viability post-phagocytosis (1 h) measured using DRAQ7. The percentage is calculated in the single cell gate. Each symbol represents a donor. Distinct patterns identify distinct thawing protocols (double right to left stripe=37 C.; double right to left stripe=4° C. then 37° C.).

Figure 3:
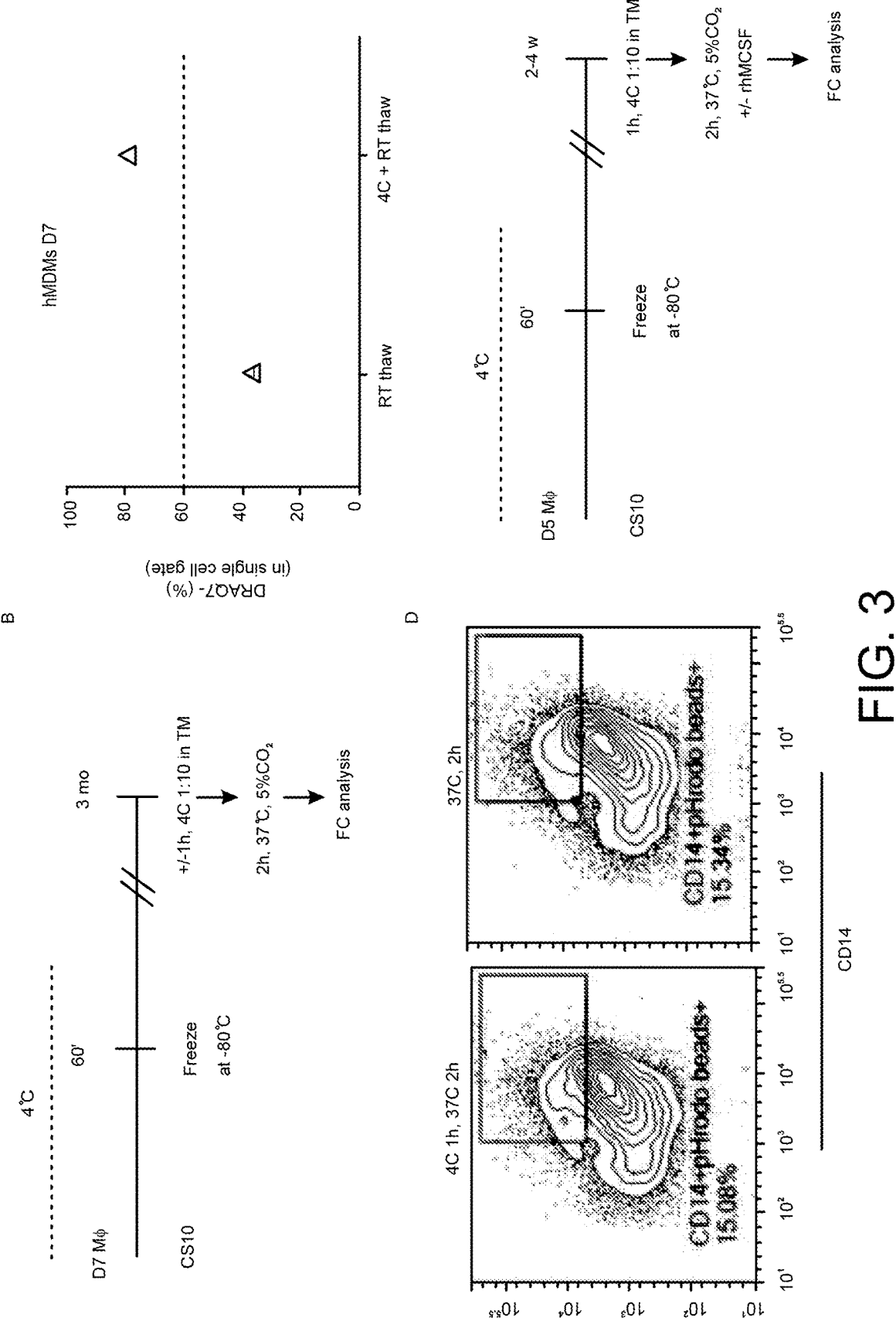
Figure 3:
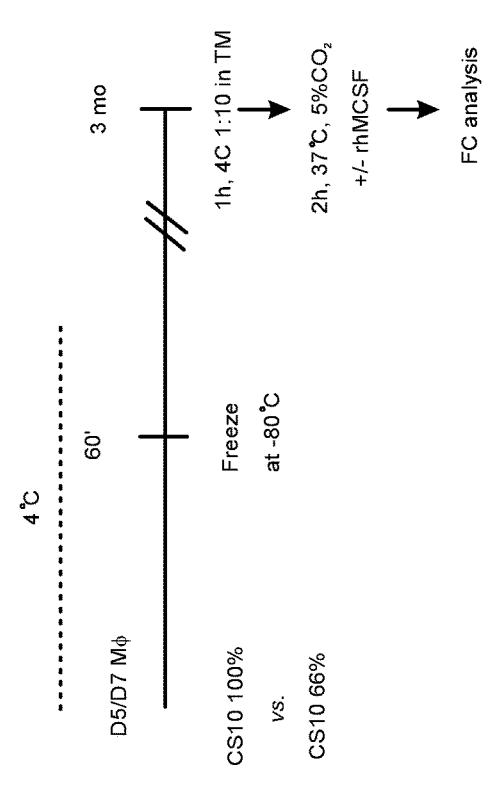
Figure 3:
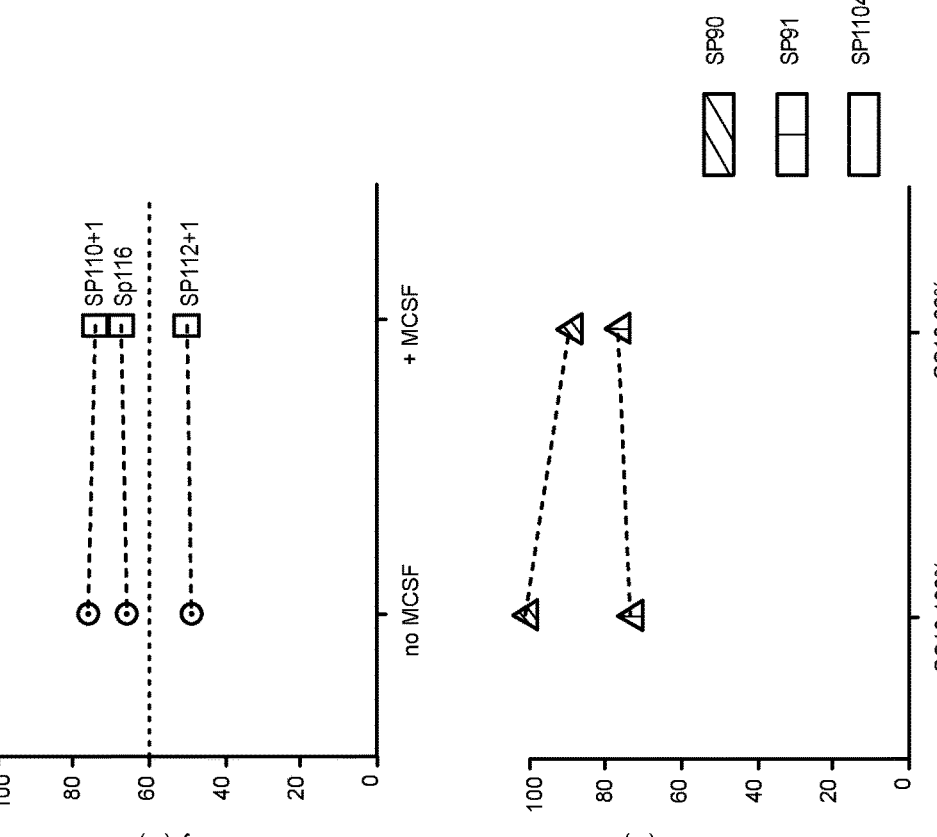

FIG. 3 shows further testing of various cryopreservation conditions for hMDMs day5 (D5) and day7 (D7) methods of in vitro production; A Experimental design: GMP-graded hMDMs D7 are diluted at 20×10$^6$/mL in CS10 (CryoStore 10). After 60 mins of cool down at 4° C., hMDMs are frozen at –80° C. After three months cells are thawed, diluted in TexMACS and incubated or not for 1 h at 4° C., before being incubated for 2 h at 37° C., 5% CO$_2$; B Flow cytometry analysis of cell viability of hMDMs D7 subjected to 60 mins cool down time before freezing. hMDMs from the same donor were compared when thawed at 37° C. for 2 h or 1 h at 4° C. followed by 2 h at at 37° C., 5% CO$_2$. The dashed line marks our minimal intended goal for viability for clinical use; C Flow cytometry analysis of phagocytosis of pHrodo beads coated with E. coli by hMDMs D7 thawed with or without the incubation at 4° C. for 1 h prior to incubation for 2 h, at 37° C., 5% CO$_2$; D Experimental design: GMP-graded hMDMs D5 are diluted at 20×10$^6$/mL in CS10. After 60 mins of cool down at 4° C., hMDMs are frozen at −80° C. After 2-4 weeks hMDMs are thawed, diluted in TexMACS and incubated for 1 h at 4° C., before being incubated for 2 h at 37° C., 5% $CO_2$ in the presence or in the absence of GMP-graded rhMCSF (100 ng/mL); E Flow cytometry analysis of cell viability of hMDMs D5 subjected to 60 mins cool down time before freezing. hMDMs from the same donors were compared when thawed for 1 h at 4° C. followed by 2 h at 37° C., 5% $CO_2$ in the presence or in the absence of GMP-graded rhMCSF. The dashed line marks our minimal intended goal for viability for clinical use; F Experimental design: GMP-graded hMDMs D5 are diluted at $20\times10^6$/mL in CS10 100% or 66%. After 60 mins of cool down at 4° C., hMDMs are frozen at −80° C. After 3 months hMDMs are thawed, diluted in TexMACS and incubated for 1 h at 4° C., before being incubated for 2 h at 37° C., 5% $CO_2$ in the presence or in the absence of GMP-graded rhMCSF; G Automated counter analysis of cell numbers of hMDMs D5 diluted at $20\times10^6$/mL in CS10 100% or 66% before freezing. Each symbol represents a donor; H Flow cytometry analysis of cell viability of hMDMs D5 diluted at $20\times10^6$/mL in CS10 100% or 66% before freezing. The same donors are compared when GMP-graded rhMCSF is used or not during the thawing process (circle=no MCSF; square=+MCSF). Each symbol represents a donor. The dashed line marks our minimal intended goal for viability for clinical use.

Figure 4:
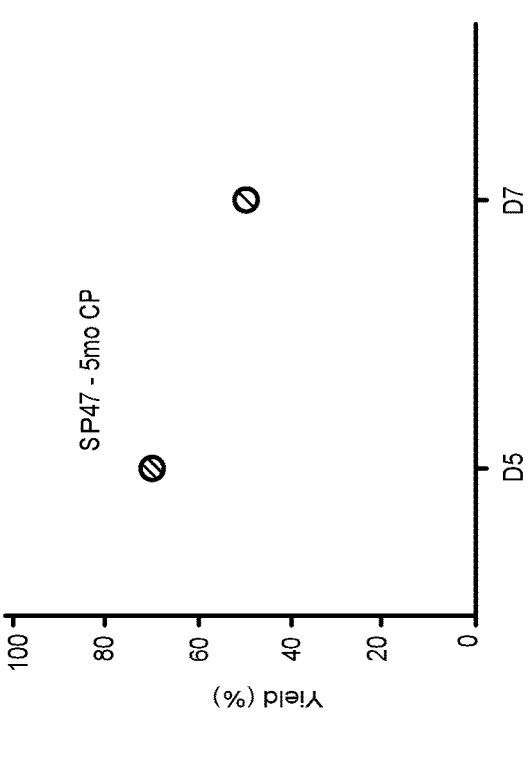
Figure 4:
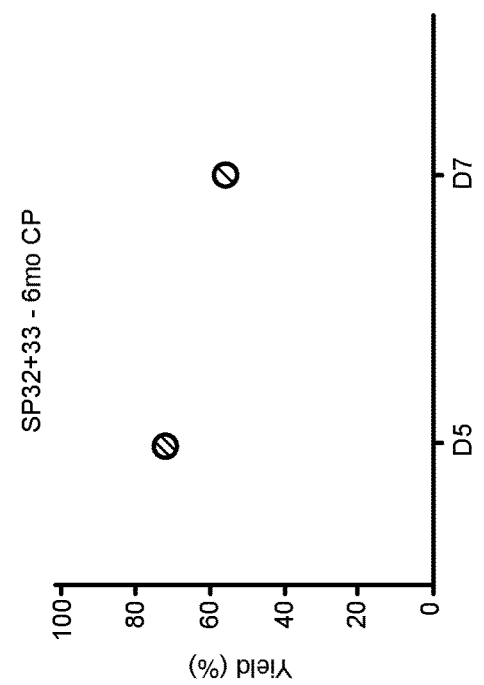
Figure 4:
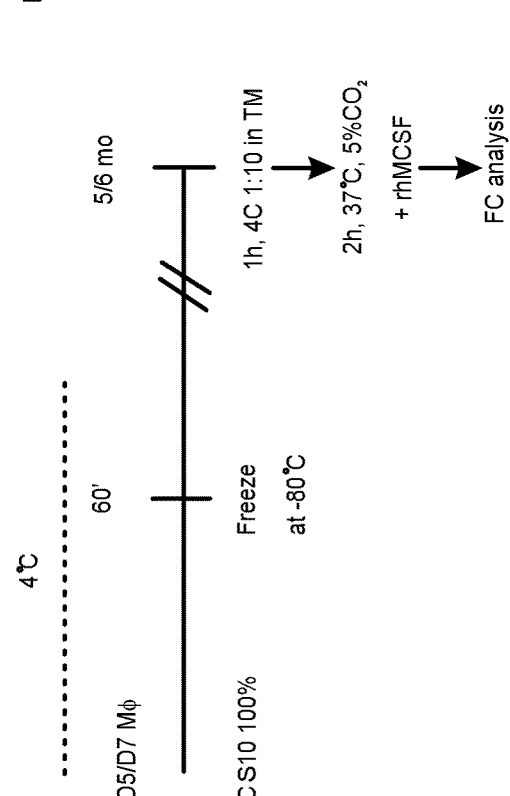
Figure 4:
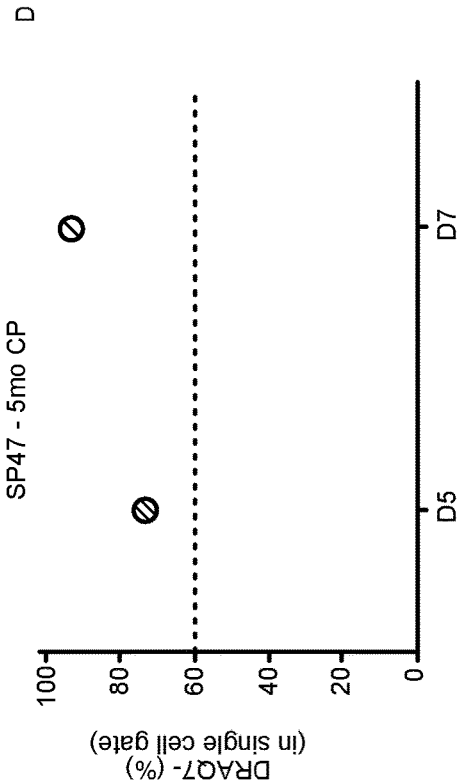
Figure 4:
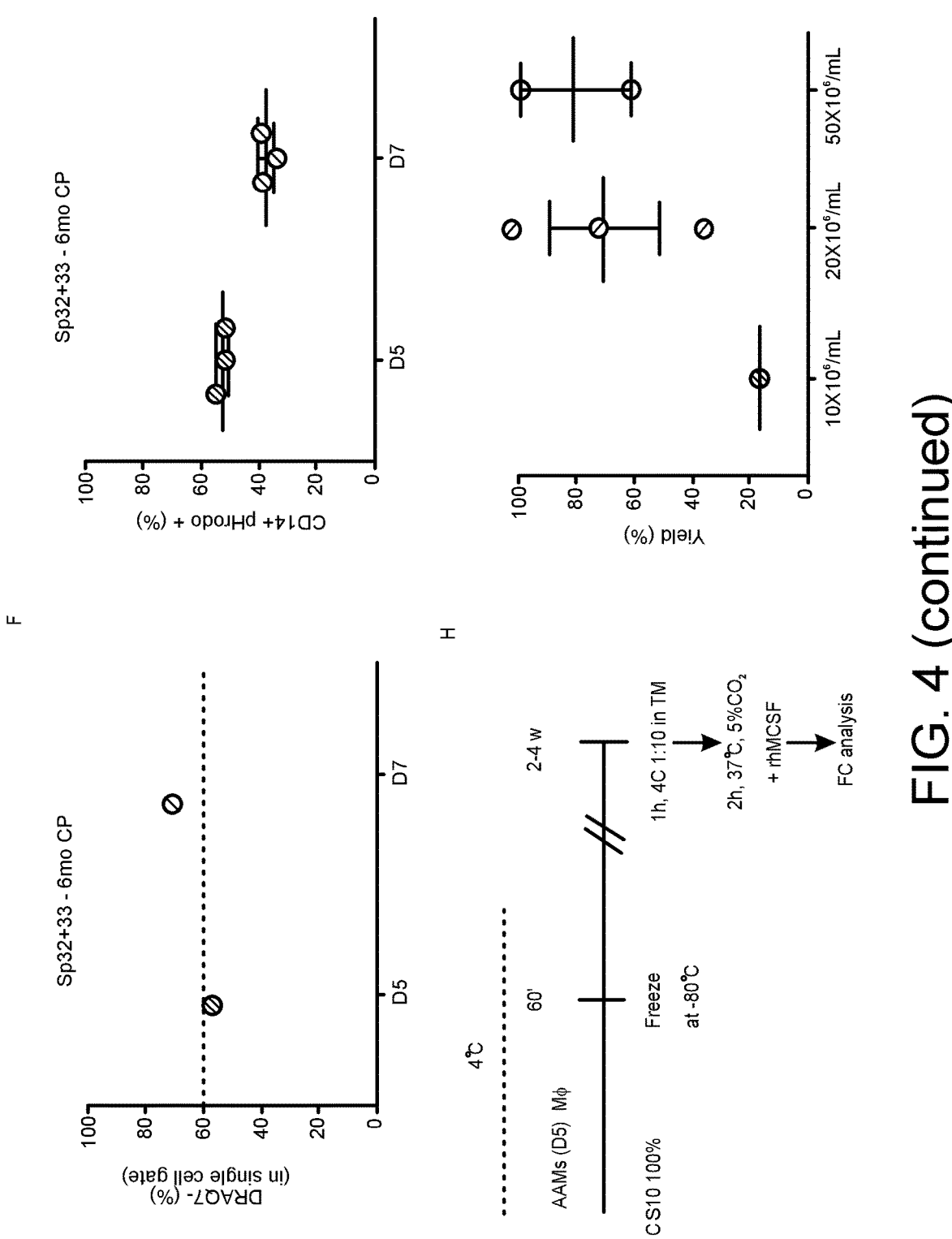
Figure 4:
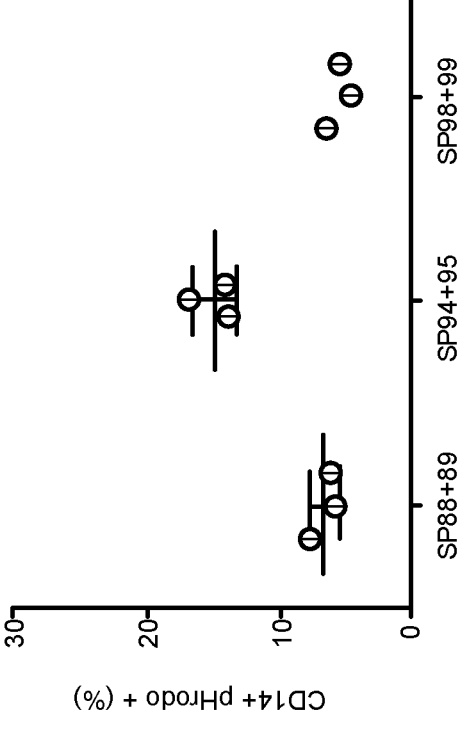
Figure 4:
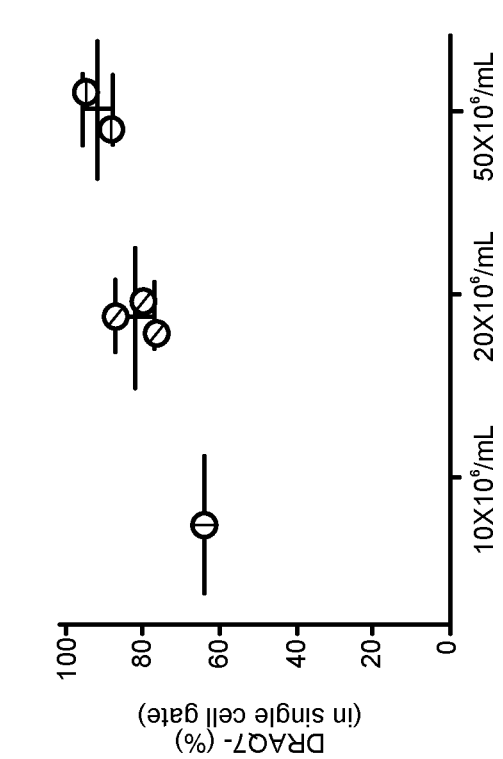

FIG. 4 shows testing of long-term cryopreservation (CP) for hMDMs day5 (D5) and day7 (D7) methods of in vitro production; A Experimental design: GMP-graded hMDMs D5/D7 are diluted at $20\times10^6$/mL in CS10 100%. After 60' of cool down at 4° C., hMDMs are frozen at −80 C. After 5-6 months hMDMs are thawed, diluted in TexMACS and incubated for 1 h at 4° C., before being incubated for 2 h at 37° C., 5% $CO_2$ in the presence of GMP-graded rhMCSF; B Automated counter analysis of cell numbers of hMDMs D5/d7 diluted at $20\times10^6$/mL in CS10 100% before freezing. hMDMs from the same donor is compared (D5 vs. D7 manufacturing protocol); C Flow cytometry analysis of cell viability of hMDMs D5 diluted at $20\times10^6$/mL in CS10 100% before freezing. The same donor is compared when hMDMs are manufactured using the D5 or the D7 protocol. The dashed line marks our minimal intended goal for viability for clinical use; D Automated counter analysis of cell numbers of hMDMs D5/D7 diluted at $20\times10^6$/mL in CS10 100% before freezing. hMDMs from the same donor is compared (D5 vs. D7 manufacturing protocol); E Flow cytometry analysis of cell viability of hMDMs D5 diluted at $20\times10^6$/mL in CS10 100% before freezing. The same donor is compared when hMDMs are manufactured using the D5 or the D7 protocol. The dashed line marks our minimal intended goal for viability for clinical use; F Flow cytometry analysis of phagocytosis of pHrodo beads coated with *E. coli* by hMDMs D5 vs D7 thawed after 6 months of cryopreservation. G Experimental design: GMP-graded hMDMs polarised with rhIL4+rhIL13 to alternatively activated macrophages (AAMs) are diluted at $10\times10^6$/mL, $20\times10^6$/mL and $50\times10^6$/mL in CS10 100%. After 60' of cool down at 4° C., hMDMs are frozen at −80 C. After 2-4 weeks AAMs are thawed, diluted in TexMACS and incubated for 1 h at 4° C., before being incubated for 2 h at 37° C., 5% CO2 in the presence of GMP-graded rhMCSF (100 ng/mL)+rhIL4 (10 ng/mL)+rhIL13 (10 ng/mL). H Automated counter analysis of cell numbers of AAMs diluted at $10\times10^6$/mL (double diagonal line), $20\times10^6$/mL (diagonal line) and $50\times10^6$/mL (empty) in CS10 100% before freezing. AAMs from the same donor are compared at the distinct concentrations; I Flow cytometry analysis of cell viability of hMDMs D5 diluted at $10\times10^6$/mL (vertical line), $20\times10^6$/mL (diagonal line) and $50\times10^6$/mL (horizontal line) in CS10 100% before freezing. The same donor is compared when AAMs are manufactured using the distinct concentrations at freezing; J Flow cytometry analysis of phagocytosis of pHrodo beads coated with *E. coli* by AAMs frozen at $20\times10^6$/mL thawed after 2-4 weeks of cryopreservation. Each column is a distinct donor, and a technical triplicate is shown for each donor.

Figure 5:
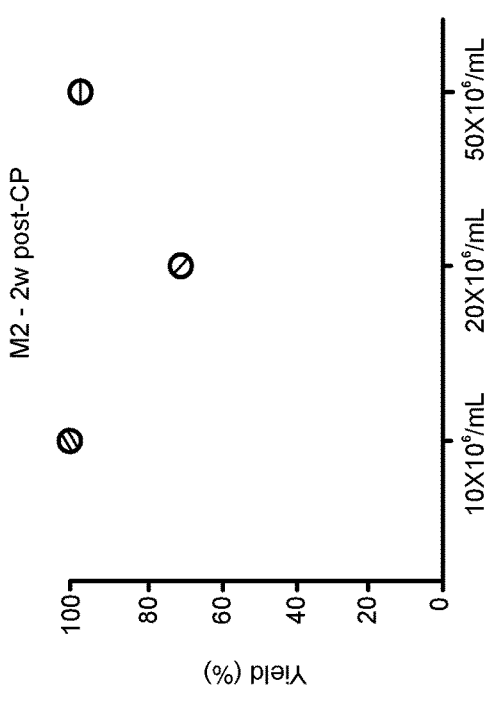
Figure 5:
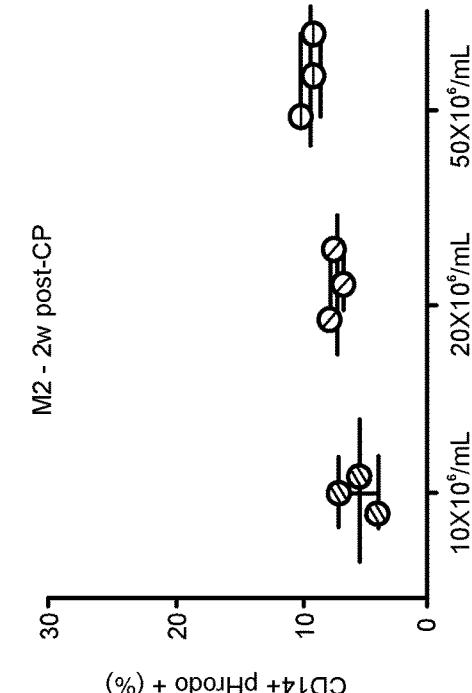
Figure 5:
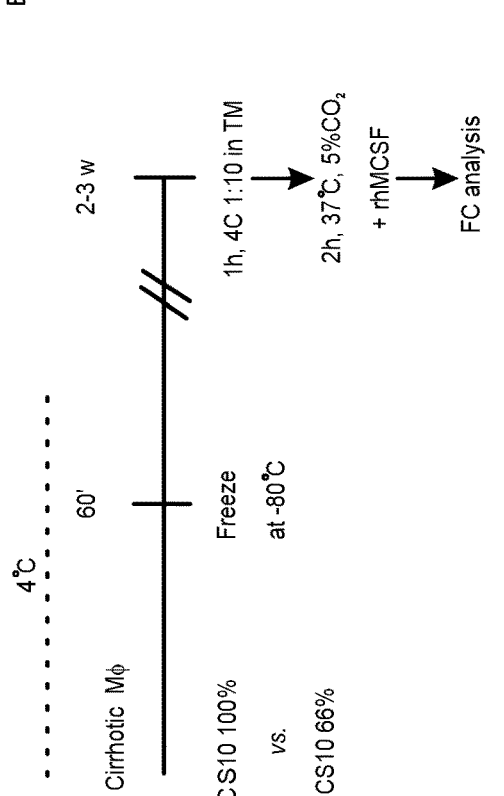
Figure 5:
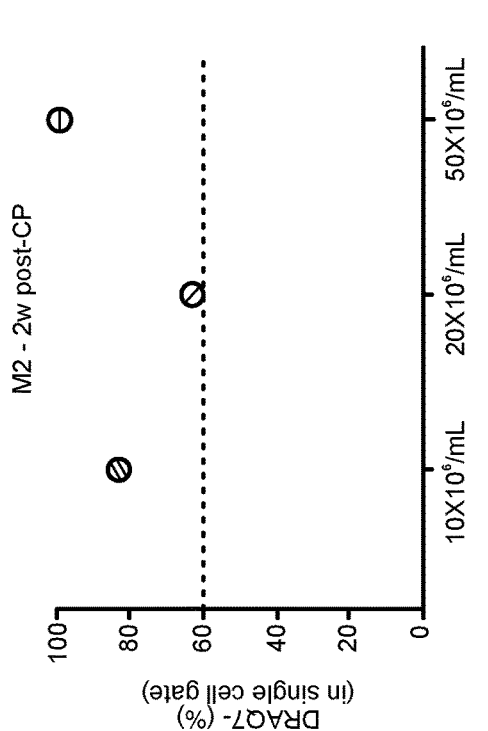
Figure 5:
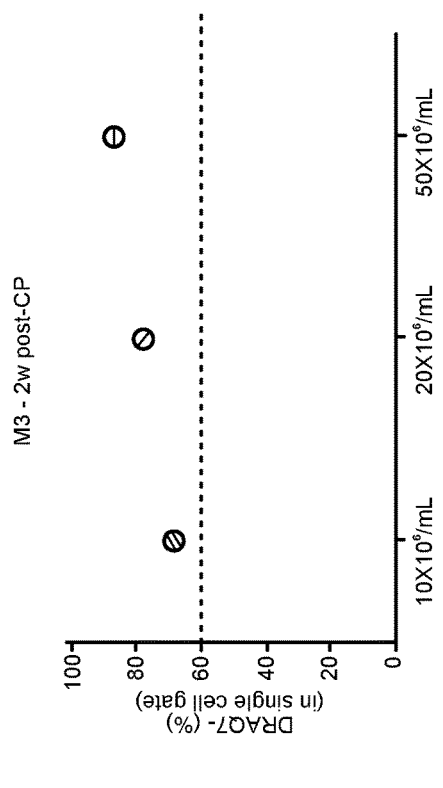
Figure 5:
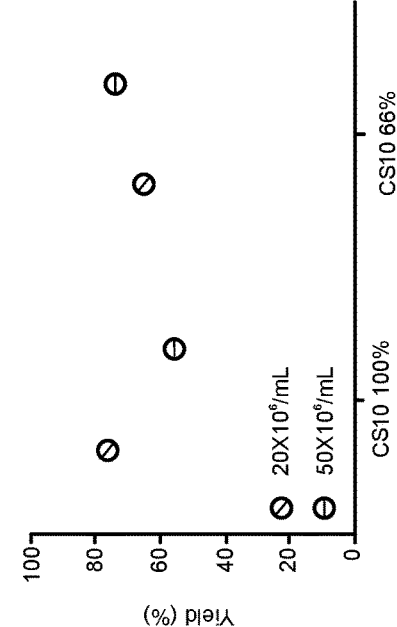
Figure 5:
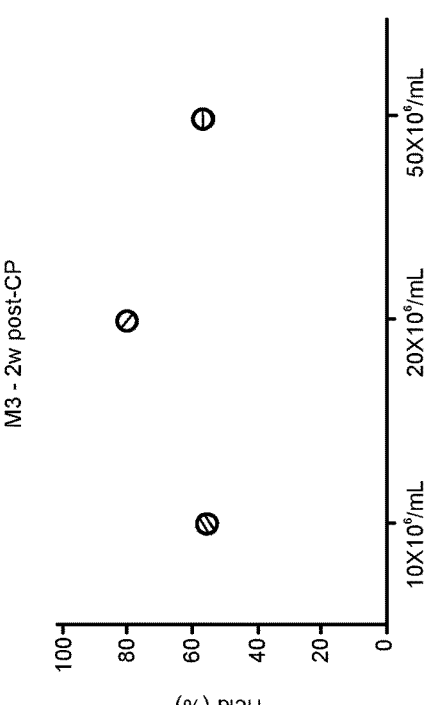
Figure 5:
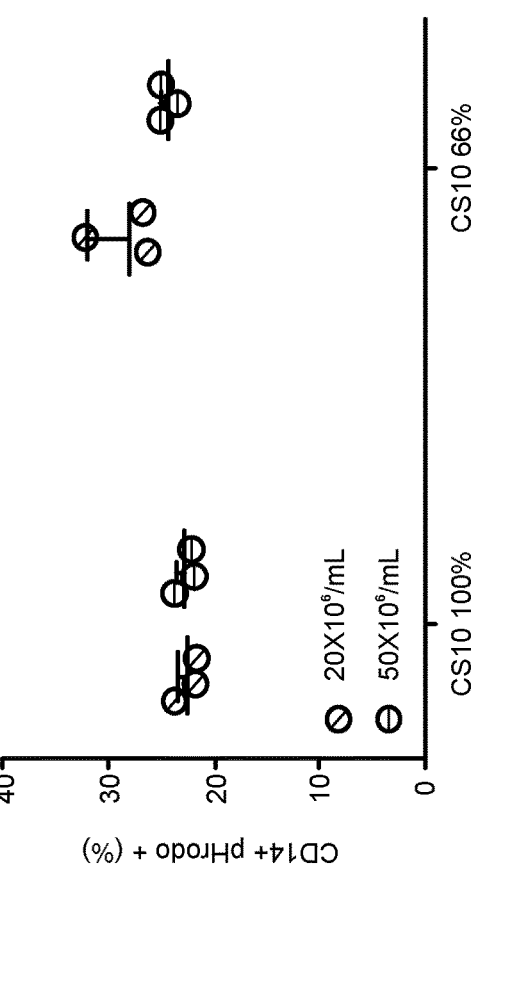

FIG. 5 shows testing of cryopreservation protocol using GMP-graded hMDMs D7 from cirrhotic patients, after overnight hold to test release criteria for clinical use; A Experimental design: GMP-graded hMDMs D7 plus o.n. hold are diluted at various concentration in CS10 100% or 66%. After 60 mins of cool down at 4° C., hMDMs are frozen at −80° C. After 2-3 weeks hMDMs are thawed, diluted in TexMACS and incubated for 1 h at 4° C., before being incubated for 2 h at 37° C., 5% $CO_2$ in the presence of GMP-graded rhMCSF; B Automated counter analysis of cell numbers of hMDMs D7+o.n. hold post-thaw (patient M2). Distinct patterns identify distinct concentrations at freezing (double diagonal line=$10\times10^6$/mL; diagonal line=$20\times10^6$/mL; horizontal line=$50\times10^6$/mL); C Flow cytometry analysis of cell viability of hMDMs D7+o.n. hold post-thaw (patient M2). Distinct patterns identify distinct concentrations at freezing (double diagonal line=$10\times10^6$/mL; diagonal line=$20\times10^6$/mL; horizontal line=$50\times10^6$/mL). The dashed line marks our minimal intended goal for viability for clinical use; D Flow cytometry analysis of phagocytosis of pHrodo beads coated with *E. coli* by hMDMs D7 plus o.n. hold after thaw (patient M2). Distinct patterns identify distinct concentrations at freezing (double diagonal line=$10\times10^6$/mL; diagonal line=$20\times10^6$/mL; horizontal line=$50\times10^6$/mL); E Automated counter analysis of cell numbers of hMDMs D7+o.n. hold post-thaw (patient M3). Distinct patterns identify distinct concentrations at freezing (double diagonal line=$10\times10^6$/mL; diagonal line=$20\times10^6$/mL; horizontal line=$50\times10^6$/mL); F Flow cytometry analysis of cell viability of hMDMs D7+o.n. hold post-thaw (patient M3). Distinct patterns identify distinct concentrations at freezing (double diagonal line=$10\times10^6$/mL; diagonal line=$20\times10^6$/mL; horizontal line=$50\times10^6$/mL). The dashed line marks our minimal intended goal for viability for clinical use; G Flow cytometry analysis of phagocytosis of pHrodo beads coated with *E. coli* by hMDMs D7 plus o.n. hold after thaw (patient M3). Distinct patterns identify distinct concentrations at freezing (double diagonal line=$10\times10^6$/mL; diagonal line=$20\times10^6$/mL; horizontal line=$50\times10^6$/mL); H Automated counter analysis of cell numbers of hMDMs D7+o.n. hold post-thaw (patient M3) cryopreserved in CS10 100% or CS10 66%. Distinct colours identify distinct concentrations at freezing (diagonal line=$20\times10^6$/mL; horizontal line=$50\times10^6$/mL); I Flow cytometry analysis of cell viability of hMDMs D7+o.n. hold post-thaw (patient M3) cryopreserved in CS10 100% or CS10 66%. Distinct colours identify distinct concentrations at freezing (diagonal line=$20\times10^6$/mL; horizontal line=$50\times10^6$/mL). The dashed blue line marks our minimal intended goal for viability for clinical use; J Flow cytometry analysis of phagocytosis of pHrodo beads coated with *E. coli* by hMDMs D7 plus o.n. hold (patient M3) cryopreserved in CS10 100% or CS10 66%. Distinct colours identify distinct concentrations at freezing (pink=$20\times10^6$/mL; yellow=$50\times10^6$/mL).

Figure 6:
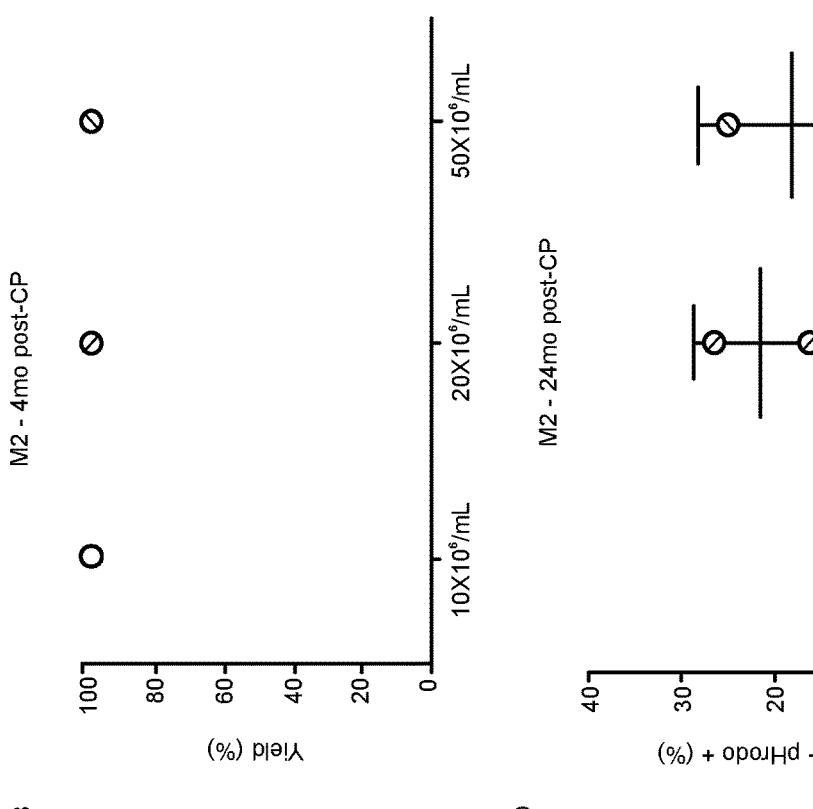
Figure 6:
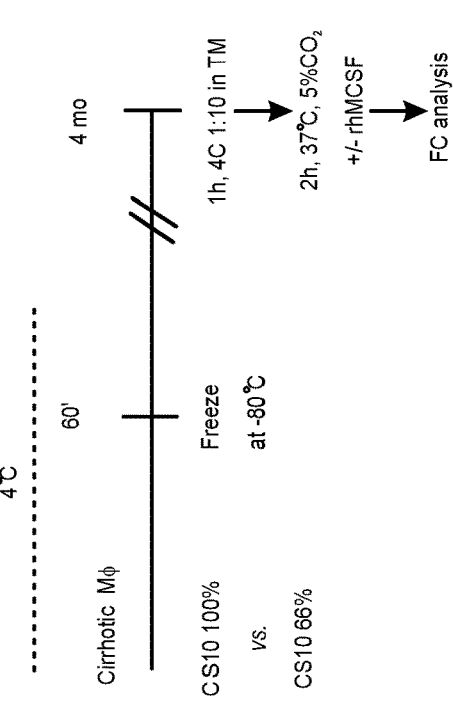
Figure 6:
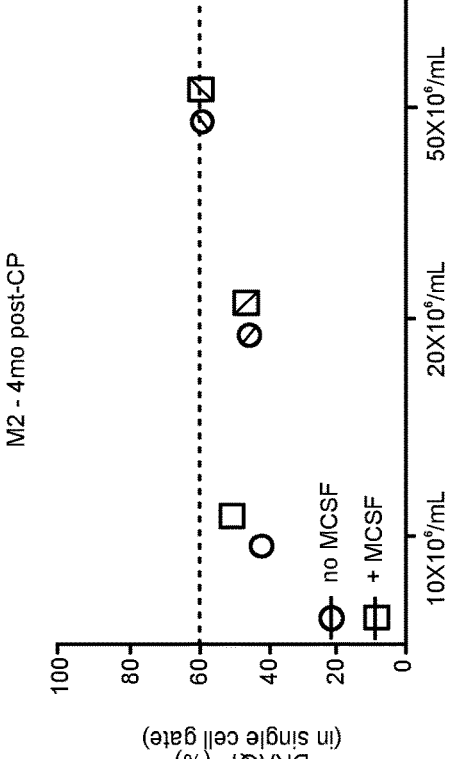
Figure 6:
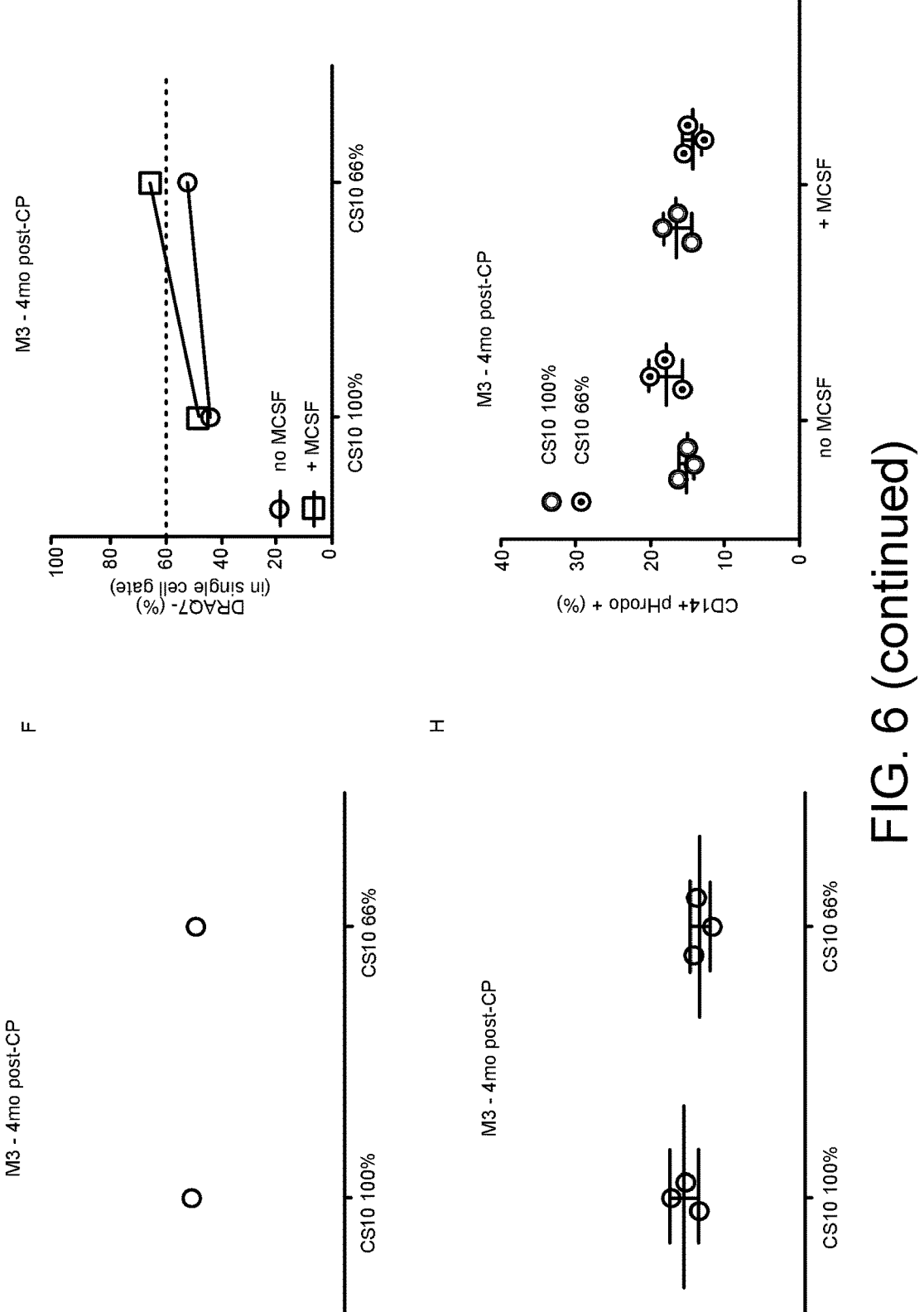

FIG. 6 shows long term cryopreservation protocols using GMP-graded hMDMs D7 from cirrhotic patients after overnight hold to test release criteria for clinical use; A Experimental design: GMP-graded hMDMs D7 plus o.n. hold are diluted at various concentration in CS10 100% or 66%. After 60 mins of cool down at 4° C., hMDMs are frozen at −80° C. After 4 months hMDMs are thawed, diluted in TexMACS and incubated for 1 h at 4° C., before being incubated for 2 h at 37° C., 5% $CO_2$ in the presence or in the absence of GMP-graded rhMCSF; B Automated counter analysis of cell numbers of hMDMs D7+o.n. hold post-thaw (patient M2). Distinct patterns identify distinct concentrations at freezing (empty=$10\times10^6$/mL; left to right diagonal line=$20\times10^6$/mL; right to left diagonal line=$50\times10^6$/mL). Cryopreservation is in 100% CS10; C Flow cytometry analysis of cell viability of hMDMs D7+o.n. hold post-thaw (patient M2). Distinct patterns identify distinct concentrations at freezing (empty=$10\times10^6$/mL; left to right diagonal line=$20\times10^6$/mL; right to left diagonal line=$50\times10^6$/mL). Circles=no MCSF; squares=+MCSF. The dashed line marks our minimal intended goal for viability for clinical use. Cryopreservation is in 100% CS10; D Flow cytometry analysis of phagocytosis of pHrodo beads coated with E. coli by hMDMs D7 plus o.n. hold after thaw (patient M2). Distinct patterns identify distinct concentrations at freezing (empty=$10\times10^6$/mL; left to right diagonal line=$20\times10^6$/mL; right to left diagonal line=$50\times10^6$/mL). Cryopreservation is in 100% CS10; E Automated counter analysis of cell numbers of hMDMs D7+o.n. hold post-thaw (patient M3). hMDMs from M3 are compared at thaw after cryopreservation in 100% CS10 vs. 66% CS10 at $20\times10^6$/mL; F Flow cytometry analysis of cell viability of hMDMs D7+o.n. hold post-thaw (patient M3). hMDMs from M3 are compared after thaw with or without the supplementation of rhMCSF. Cryopreservation is in 100% CS10 vs. 66% CS10 at $20\times10^6$/mL. Circles=no MCSF; squares=+MCSF. The dashed line marks our minimal intended goal for viability for clinical use; G Flow cytometry analysis of phagocytosis of pHrodo beads coated with E. coli by hMDMs D7 plus o.n. hold after thaw (patient M3). hMDMs from M3 are compared at thaw after cryopreservation in 100% CS10 vs. 66% CS10 at $20\times10^6$/mL; H Flow cytometry analysis of phagocytosis of pHrodo beads coated with E. coli by hMDMs D7+o.n. hold post-thaw (patient M3). hMDMs from M3 are compared after thaw with or without the supplementation of rhMCSF. Cryopreservation is in 100% CS10 vs. 66% CS10 at $20\times10^6$/mL.

Figure 7:
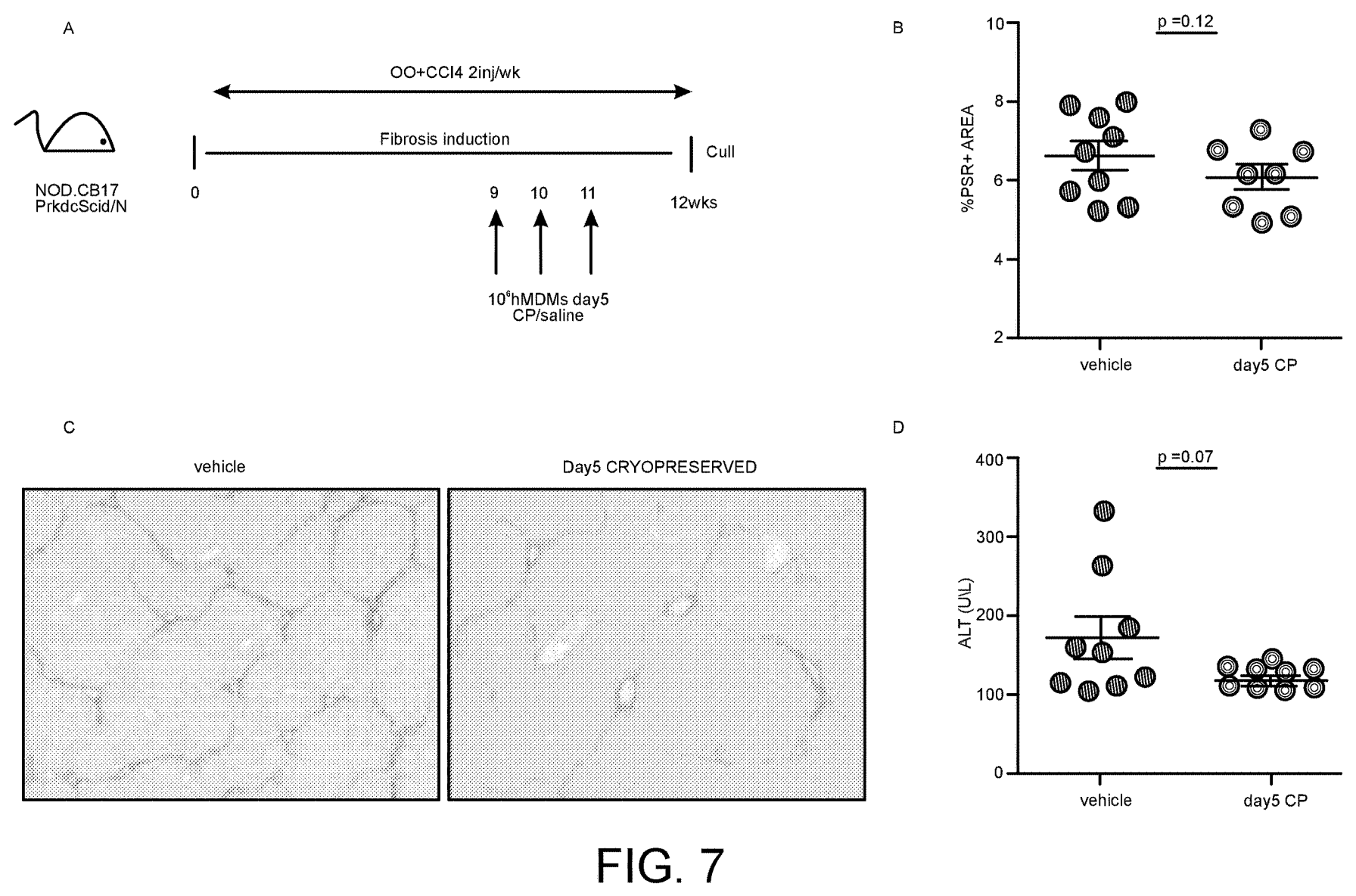
Figure 7:
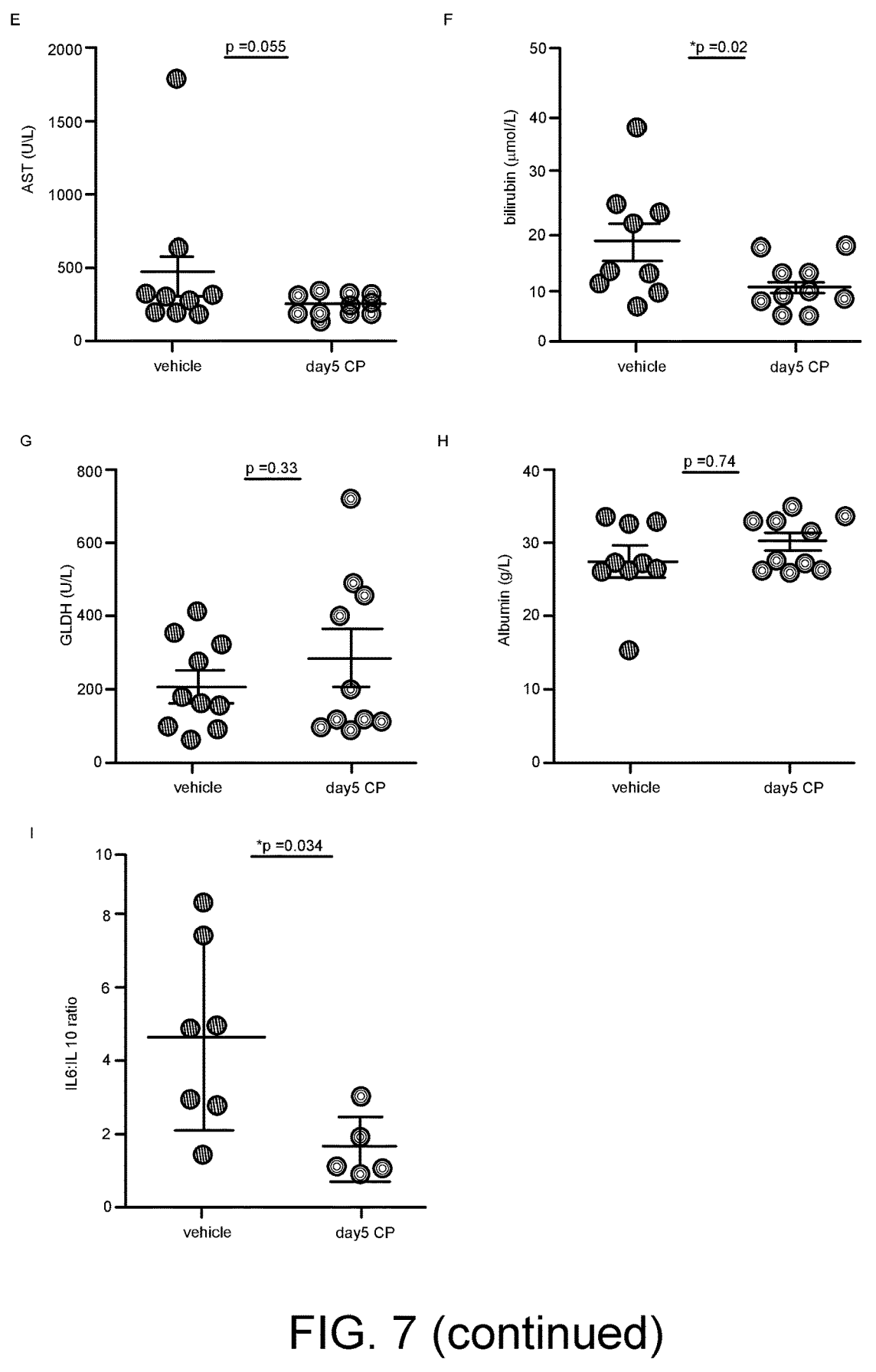

FIG. 7 shows testing of cryopreserved CP hMDMs D5 efficacy as a cell therapy in vivo; A Experimental design: NOD/SCID mice are injected twice a week for 12 weeks with $CCl_4$ to induce severe liver fibrosis. Cryopreserved (CP) hMDMs D5 are injected at the start of week 9, 10 and 11. Mice are culled one week after the last dose of macrophage therapy; B PSR staining is performed on the livers treated with cryopreserved (CP) hMDMs D5 or saline and stained areas are quantified. Each symbol represents a mouse. 6 to 10 10× fields/mouse are quantified. D'Agostino and Pearson omnibus normality test was carried out, and then a non-parametric Mann Whitney test was applied. p=0.12; C Representative pictures of day5 hMDMs and saline treated livers. (10×, brightfield); D-H Dosage of circulating serum ALT (D), AST (E), bilirubin (F), GLDH (G) and Albumin (H). Each symbol represents a mouse. D'Agostino and Pearson omnibus normality test was carried out, followed by a one-tailed t-test for unpaired data with Welch's correction for samples with unequal variances. p non-significant for ALT, AST, GLDH and Albumin. **p=0.002 for bilirubin; I Ratio of circulating levels of IL6:IL10. Dosage of circulating serum IL6 and IL10 performed using the MSD Mesoscale platform. Each symbol represents a mouse. D'Agostino and Pearson omnibus normality test was carried out, followed by a two-tailed t-test for unpaired data with Welch's correction for samples with unequal variances (*p=0.034).

Figure 8:
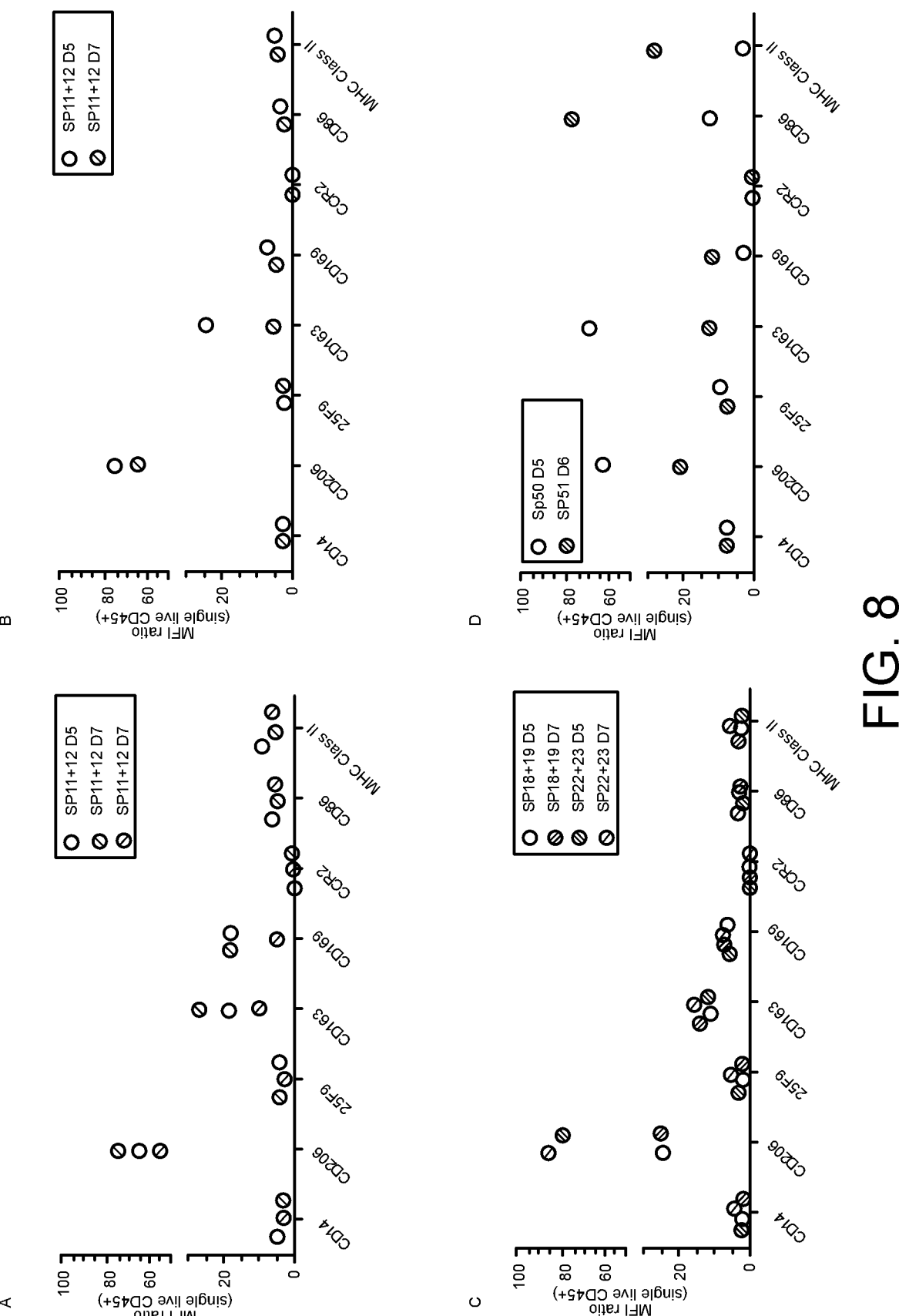
Figure 8:
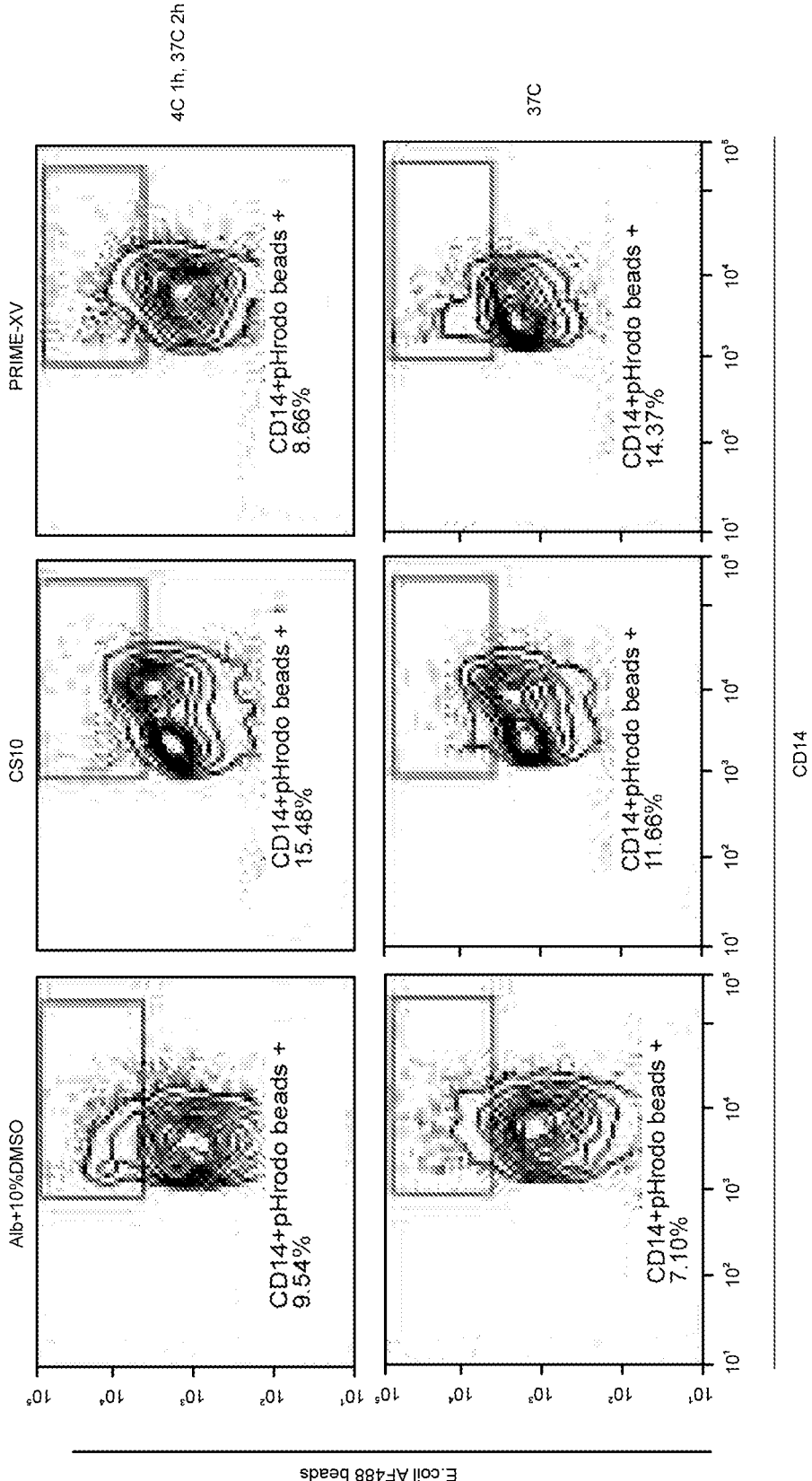

FIG. 8 shows flow cytometry analysis of cell surface markers. A-D Each symbol represents a donor. MFI ratio is calculated dividing the day5 or day7 MFI by the MFI of CD14+ monocytes at the start of the culture; E is a representative contour plot of the various thawing conditions and medium tested (4 C.=1 h at 4 degrees followed by 1 h at 37 degrees in incubator; 37 C.=2 h at 37 degrees in incubator). Contour plot are obtained by gating on the single, live (DRAQ7$^-$) CD14+ events. Gates are set on the FMO for AF488. The plots are all from a single donor (SP51).

Figure 9:
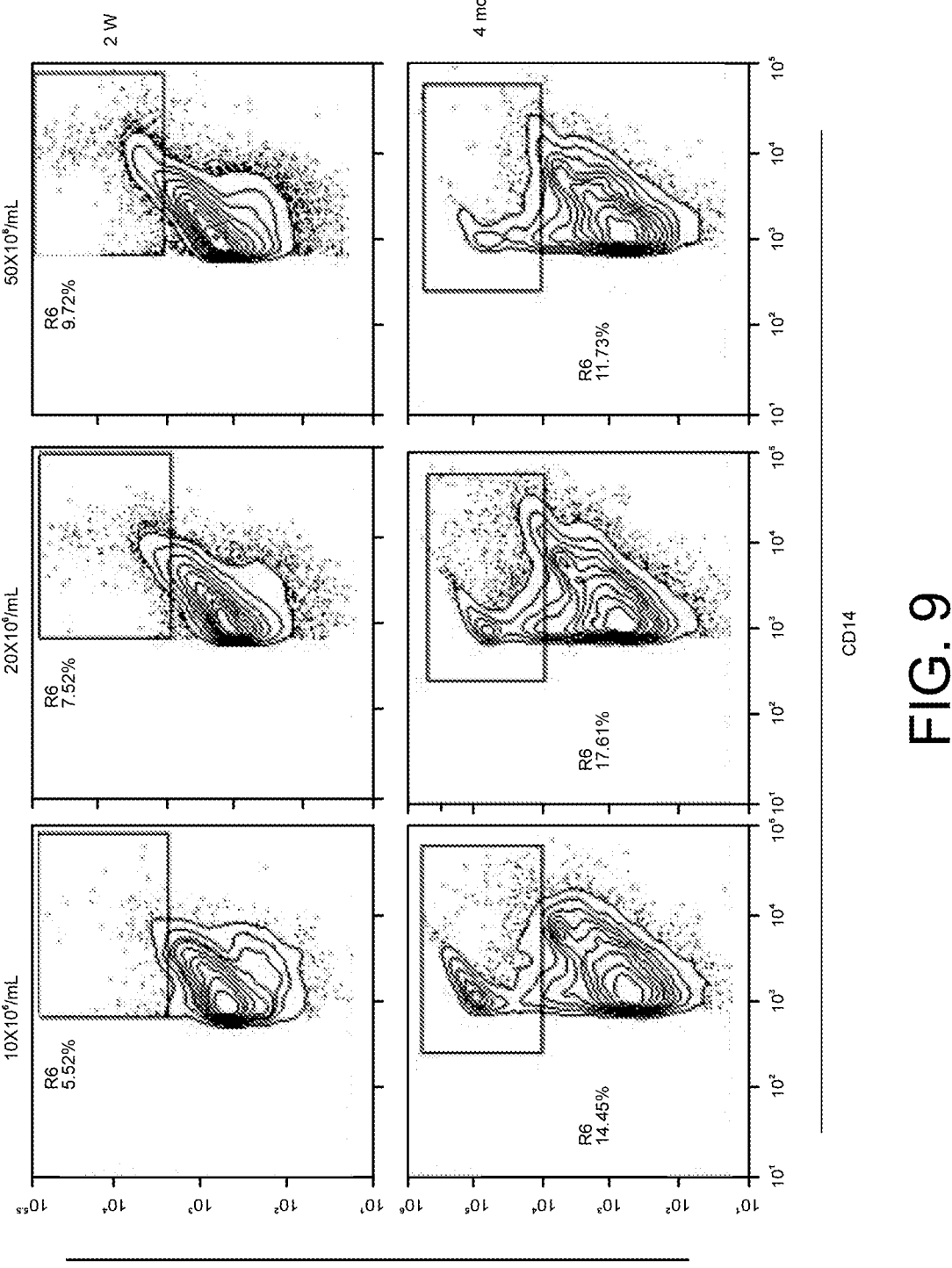
Figure 9:
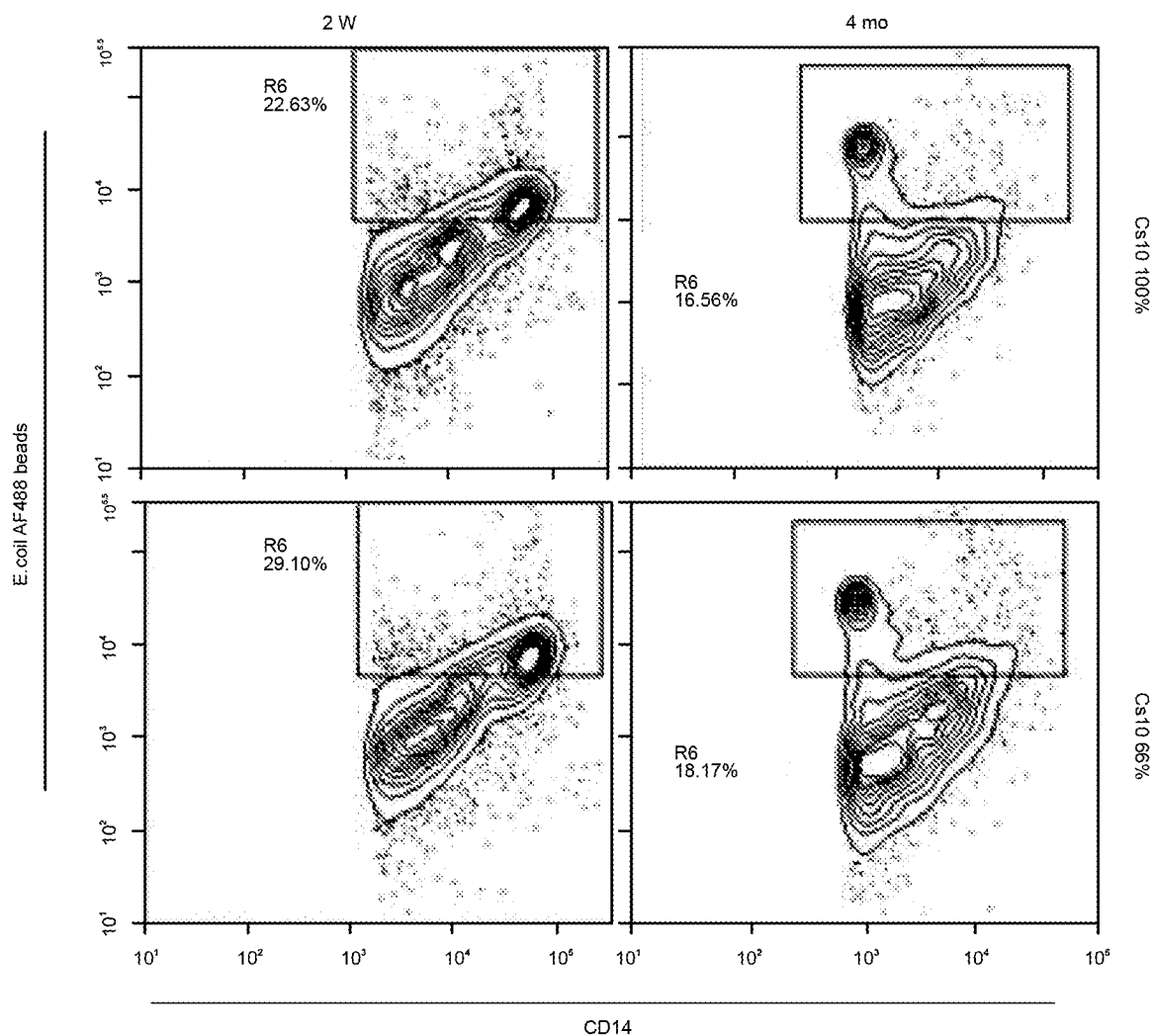
Figure 9:
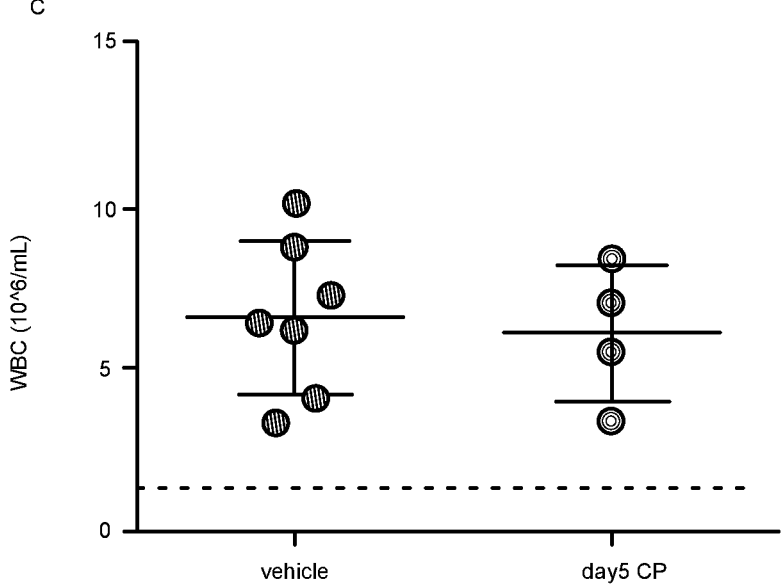
Figure 9:
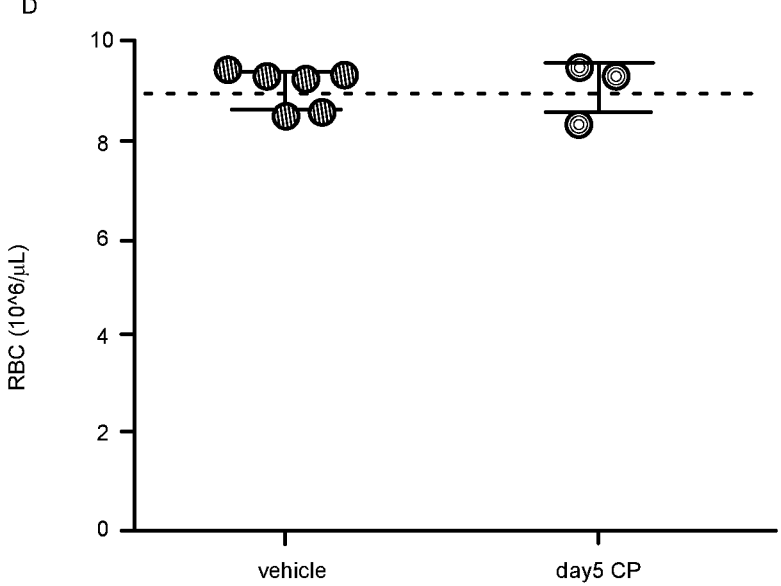
Figure 9:
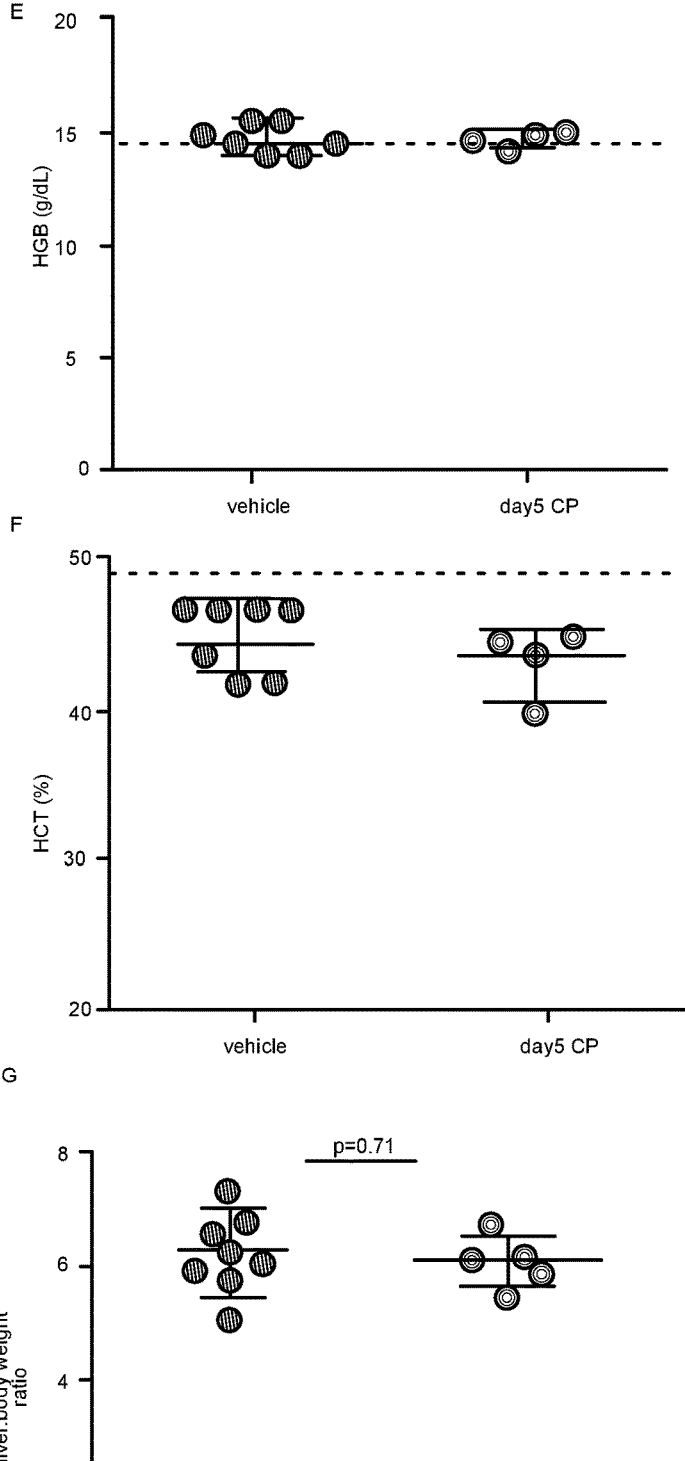

FIG. 9 shows representative plots of phagocytosis assays quantified in FIG. 5 and FIG. 6, and other clinical parameters from the in vivo test presented in FIG. 7. A Representative contour plot of thawed hMDMs from a single donor. hMDMs have been frozen at distinct concentration and thawed at distinct time points (2 weeks and 4 months post freezing); B Representative contour plot of thawed hMDMs from a single donor. hMDMs have been frozen using CS10 100% or CS10 66% and thawed at distinct time points (2 weeks and 4 months post freezing); C-EG White Blood Cells (WBC), Red Blood Cells (RBC), haemoglobin (HGB) and haematocrit (HCT) in peripheral blood are measured at the time of culling. Blood from vehicle-treated and CP hMDMs D5-treated mice is analysed. A normality test is applied, followed by an unpaired, two-tailed t-test. All results are non-significant; (G) Liver:body weight ratio expressed in percentage (%) as measured at the point of culling. HGB, HCT and Liver:body weight ratio from vehicle-treated and CP hMDMs D5-treated mice is reported. A normality test is applied, followed by an unpaired, two-tailed t-test. All results are non-significant.

EXAMPLES

The present invention is further exemplified by the following examples. The examples are for illustrative purpose only and are not intended, nor should they be construed as limiting the invention in any manner.

1. Materials and Methods

GMP Human Monocyte-Derived Macrophages (hMDMs) Cell Culture

We isolated monocytes from a buffy coat product from a healthy volunteer sourced from the Scottish National Blood Transfusion Service (SNBTS) using a Ficoll gradient (GE Healthcare) followed by a magnetic column selection using CliniMACS CD14 Reagent (Miltenyi Biotec). We then matured monocytes for 1 to 7 days in culture in TexMACS without phenol red (Miltenyi Biotec) in the presence of 100 ng/mL GMP-graded recombinant human macrophage colony-stimulating factor (rhM-CSF) (R&D System, Biotechne). hMDMs day5 and day7 are cultured in 6 wells multi-well plate (Corning Costar) at a density of $2\times10^6$/cm². hMDMs were fed at day 3 when matured for 7 days: briefly, half of the culture medium volume is added to each well, supplemented with rhM-CSF at a final concentration of 100 ng/mL. Day5 and day7 hMDMs were counted using an automated counter (TC20, BioRad).

Freezing of Human Monocyte-Derived Macrophages (hMDMs)

hMDMs day5 and hMDMs day7 were re-suspended in the following medium: Albumin+10% DMSO, Albumin+20% DMSO, CryoStore 10 (CS10), and Prime XV. hMDMs day5 and day7 were re-suspended in the various freezing medium at the following concentrations: $1\times10^6$/mL, $5\times10^6$/mL, $10\times10^6$/mL, $20\times10^6$/mL, $50\times10^6$/m L. hMDMs day5 and day7 were cooled down prior to freezing for either 30 mins or 60'mins by placing each vial at 4° C. in a Mr Frosty container, which progressively lower the temperature at a rate of about 1° C./min. hMDMs day5 and day7 were frozen at −80° C. in Mr Frosty for a period of time between 2 weeks and 6 months.

Thawing of Human Monocyte-Derived Macrophages (hMDMs)

In the first experiment, hMDMs day5 and day7 were thawed, diluted 1:10 in GMP-graded TexMACS (Miltenyi Biotec) and spun at 300×g, 5 mins at 4° C. They were then re-suspended in 10 mL of GMP-graded TexMACS and cultured for 2 h in 6-multi well plates (Cornig-Costar) at 37° C., 5% $CO_2$ prior to viability analysis as described below.

In all the other experiments, hMDMs day5 and day7 were diluted 1:10 in cold (4 C. to 15 C.) GMP-graded TexMACS (Miltenyi Biotec). The cell suspension was directly cultured for 2 h in 6-multi well plates (Cornig-Costar) at, 5% $CO_2$ prior to viability analysis. In selected experiments, the cell suspension was progressively warmed up by placing the diluted cell suspension at 4° C. for 1 h prior to culture at 37° C., 5% $CO_2$, 5% $CO_2$. In selected experiments, rhMCSF at a concentration of 100 ng/mL (R&D System, Bio-techne) was added to the GMP-graded TexMACS. After the culture at 37° C., 5% $CO_2$, the cell suspension was subjected to viability analysis as described below.

Viability Analysis

After 2 h to 4 h of cell culture at 37° C., 5% $CO_2$, hMDMs day5 and day7 were harvested and counted using a TC20 cell counter (BioRad). $10^5$ to $10^6$ cells were placed in a flow cytometry-compatible 5 mL tube (Falcon). The cell suspension was then analysed using a Milteny Vibe flow cytometer to set the baseline fluorescence. DRAQ7 (Abcam) was then added to the cell suspension at 1:500 dilution. The cell suspension was immediately analysed using a Miltenyi Vibe flow cytometer. Data were analysed and results obtained with the MACS Quant software (Miltenyi Biotec).

Phagocytosis Assay $10^5$ hMDMs day5 and day7 post-thaw were placed in a 5 mL flow cytometry-compatible tube (Falcon) in a volume of 100 uL of PBS+2.5 mM EDTA. 100 μL of green zymosan-A coated pHrodo beads (Invitrogen, Life Technologies) were added to the cell suspension. pHrodo beads were prepared following the manufacturer's instructions. After 1 h of beads-cell co-culture, 1 mL of PBS+2.5 mM EDTA was added to each tube. Tubes were then spun at 200×g, 5 mins at 4° C. The supernatant was then eliminated and cells were re-suspended 100⁴ of PBS+2.5 mM EDTA+1% human albumin (PEA). We prepared two tubes per sample, in order to have a single staining for the pHrodo beads, and a double staining with a macrophage-specific marker. An anti-mouse CD14 antibody conjugated with VioBlue (VB) was added to the cell suspension at a concentration of 1:100 to identify macrophages. After 20 mins of incubation, the excess of antibody was washed away by adding 1 mL of PEA and by spinning the cell suspension as indicated above. The cells were re-suspended in 500 μL of PEA, and DRAQ7 (Abcam) was added at a 1:500 dilution immediately prior to analysis. The cell suspension was analysed using a Miltenyi Vibe flow cytometer. Results were analysed with the MACS Quant software (Miltenyi Biotec).

Mouse Experiments

NOD CB17 Prkdc/$^{SCID}$ mice were supplied by Charles River and housed in individually ventilated cages in a sterile animal facility with a 10-14-hours dark/light cycle and free access to food and water. All procedures were performed in accordance with UK Home Office guidelines (Animals [Scientific Procedures] Act 1986). Chronic liver fibrosis was induced in adult male mice over a 12-week period by twice weekly intraperitoneal injections of carbon tetrachloride ($CCl_4$) dissolved in sterile olive oil at a concentration of 0.2 mL/kg for the first week increasing to 0.4 mL/kg for further 10 weeks. One day after the 18th $CCl_4$ injection (9 weeks), mice were randomly allocated to receive either day 5 cryo-preserved (CP) hMDMs (n=10) or saline (vehicle, n=9) injections via tail vein. The intra-splenic route would have ensured maximal cell delivery, but it does not model the administration route used in the phase I MATCH trial (day7 hMDMs in patients with chronic liver fibrosis) (19). Day 5 hMDMs were suspended in sterile saline at a density of $5\times10^7$ cells/mL and 0.1 mL was injected via a 30-gauge needle (Myjector 0.3 mL syringes, Terumo). Day5 CP hMDMs intravenous injection was repeated at week 10 and week 11. 0.2 mL/kg $CCl_4$ administration continued for an additional week.

All mice were culled at the indicated time points using anaesthesia overdose followed by cervical dislocation as confirmatory method. Organs and blood were retrieved, processed and stored for further analysis: liver left lobe was snap frozen and stored at −80° C.; the other liver lobes were fixed in formalin 10% for 8 h and then included in paraffin blocks; kidneys, spleen, heart and lungs were fixed in formalin 10% for 8 h and then included in paraffin blocks; blood was collected in Eppendorf, left to sediment for 8 h and then spun at 10000×g for 10 minutes at room temperature to obtain serum, to be stored at −80° C.; blood collected in EDTA-coated tubes (Microvette CB300, Sarstedt) were used to collect 304 of full blood to use for the analysis of the haematological parameters using the CellTac machine (Nihon Kohden).

Liver Function Tests on Sera

Serum chemistry was performed by measurement of alanine aminotransferase (ALT), aspartate aminotransferase (AST), alkaline phosphatase (ALP), total bilirubin, and serum albumin. ALT was measured using a commercial kit (Alpha Laboratories Ltd). AST and ALP were determined by a commercial kit (Randox Laboratories). Total bilirubin was determined by the acid diazo method described by Pearlman and Lee (20) using a commercial kit (Alpha Laboratories Ltd). Mouse serum albumin measurements were determined using a commercial serum albumin kit (Alpha Laboratories Ltd). All kits were adapted for use on a Cobas Fara centrifugal analyzer (Roche Diagnostics Ltd). For all assays, intra-run precision was CV<4%. In some experiments, assays were run on plasma samples with the exception of ALP activity.

V-Plex Cytokine Dosage

Cytokines in the sera of treated mice were analysed using a V-PLEX Mouse Biomarker 10-Plex kit on a MESO Quickplex SQ 120 according to the manufacturers' instructions (Meso Scale Discovery). 10 uL of serum pre-diluted 1:5 were tested. Results are in pg/mL. The results presented herein take into consideration the above mentioned dilution factor.

Histological Analysis

Picrosirius red (PSR) staining was performed according to standard protocols. Morphometric pixel analysis to quantify histological staining was performed. For fibrosis quantification PSR stained section were scanned to create a single image with Polaris slide scanner (Perkin Elmer). A second scan on the same machine was performed to obtain multi-spectral image acquisition on 10 to 15 fields/slide at 10× magnification. Multi-spectral images were analysed using the Trainable WEKA Segmentation mode using the InForm software (Perkin Elmer).

Statistical Analysis

All data are expressed as mean±standard deviation (SD). The number of replicates is indicated in each figure and each replicate represent a biological rather than an experimental replicate. Data are analysed and graphs are generated with GraphPad Prism version 8 (GraphPad Software, Inc, USA). Statistic test has been chosen depending on the biological question behind the experiment. Briefly we used Student's t-test, one- or two-way ANOVA followed by an appropriate post-hoc test. The test used is stated in each figure legend. $P<0.05$ is considered statistically significant.

For all in vitro experiments a two-sided test is considered. All data were tested for normal distribution and equal variance before performing any statistical analysis using Prism v8.

We performed power calculation for the number of mice to use in the studies on the chronic $CCl_4$ model based on the data available from previous studies on the level of ALT (indicating liver damage) at 12 weeks of $CCl_4$ treatment. We have assumed a mu1 of 100 for 12 week-$CCl_4$ mice treated with hMDMs and a mug of 200 for 12 week-$CCl_4$ mice treated with vehicle (saline), with a sigma of 50. We have set the power desired at 0.80 assuming a statistical significance at the threshold of 0.05. The power calculation returned an n=6. This is the minimal number of mice used in each experiment. We had no available data at the time of the experiment for the APAP overdose mice treated with hMDMs day5 polarised to AAMs for 24 h. We treated the present experiment as a pilot and we plan to expand the treated cohort in the future.

For all in vivo experiments a one-sided test is considered, as we are testing the hypothesis that human macrophages reduce fibrosis in $CCl_4$ models. All data were tested for normal distribution and equal variance before performing any statistical analysis using Prism v8. Specific tests used are indicated in each legend to figure. Power calculation has been performed using the free online tool available at http://www.stat.0 bc.ca 2. Results In order to optimise a GMP-graded protocol to freeze and thaw mature human monocyte-derived macrophages (hMDMs) we first tested the procedure reported in FIG. 1A. Cooling down time before freezing and choice of freezing medium are two key steps to optimise when setting up a cryopreservation protocol: the freezing process alters the cytoplasmic composition, particularly with respect to pH and salt concentrations (21, 22); moreover, cryopreservation agents such as DMSO may both protect and cause damage to the cells (23-26). In the first set of experiments, we tested two cool down times (30 minutes and 60 minutes) at 4° C. prior to transferring the hMDMs at –80° C. in Mr Frosty to guarantee a 1° C./min cooling rate. hMDMs were frozen in a standard medium containing human albumin (Alb)+20% DMSO. hMDMs matured for either five (D5) or seven (D7) days using GMP-graded recombinant hMCSF were used in this experiment. hMDMs were frozen at distinct densities, namely $1\times10^6$, $5\times10^6$ and $10\times10^6$/mL. hMDMs were thawed, spun, counted and analysed by flow cytometry to establish viability. We set 60% viability as the minimal threshold to deem the protocol viable for translation into a therapeutic setting. hMDMs cooled down both for 30 min or 60 min prior to freezing showed insufficient viability at thaw, with the $10\times10^6$/mL concentration performing slightly better than lower concentrations (FIGS. 1B-C). The calculated yield was good both for the 30 min and the 60 min cool down time. hMDMs showed a preference for a higher concentration at the point of freezing in this case too (FIGS. 1D-E).

We then reasoned that spinning hMDMs just after thaw could have been the cause of the observed drop in viability: The cell's plasma membrane is weakened by the cryopreservation process, and spinning could cause further damage, and possibly leading the cell to cell death. We therefore repeated the same freezing procedure, followed by a thawing phase in which hMDMs were left for 2 h in the incubator in complete medium (TexMACS+rhMCSF) prior to analysis of viability by flow cytometry. In this set of experiments, we also tried a higher concentration of hMDMs at point of freezing ($20\times10^6$/mL). We tested both D5 and D7 hMDMs from the same donor (FIG. 1F). We observed an improved viability for all the conditions tested. Particularly, we reached the desired 60% minimum viability with the D5 hMDMs cooled down for 60 mins and frozen at a concentration of $20\times10^6$/mL (FIG. 1G). The D5 hMDMs offered also a better yield as compared to their D7 counterparts (FIG. 1H).

To further improve the protocol, we decided to test the two highest concentrations ($10\times10^6$/mL and $20\times10^6$/mL) with various freezing medium: Alb+20% DMSO and CS10, a GMP-graded, 10% DMSO-containing medium. CS10 is normally recommended for other cryopreservation-sensitive cell types (induced pluripotent stem cells and mesenchymal stem cells) https://www.stemcell.com/cryostor-cs10.htmL). We therefore reasoned that it could be apt to efficiently cryopreserve hMDMs. We kept the 60 mins cooling down time as it gave the best results in the previous experiments (FIG. 2A). When we analysed the viability at the point of thaw, CS10 was the best performing medium, with viability up to 80% for D5 hMDMs and up to 70% for D7 hMDMs (FIGS. 2B-C). Yield was better with CS10 for D5 hMDMs frozen at $20\times10^6$/mL (FIG. 2D). D7 hMDMs gave mixed results in terms of yield (FIG. 2E), highlighting that D5 hMDMs are the best product to bring forward to be successfully cryopreserved.

DMSO is one of the most used cryopreservation agents, however a GM P-graded DMSO-free medium is available (Prime-XV). Therefore, we decided to compare viability obtained with CS10 freezing medium and with Prime-XV. Further, in the previous experiment CS10 was compared to our home-made Alb+20% DMSO. To exclude that the key to increased viability was the 10% DMSO we compared viability obtained with CS10 and with Alb+10% DMSO. Finally, we wanted to explore the possibility that a gradient of temperature at thawing could benefit viability: every preparation was split at the time of thawing and placed either at 4° C. for 1 h, before being transferred into the incubator at 37° C., or directly into the incubator (FIG. 2F). CS10 delivered the best viability, both when hMDMs were thawed at 4° C. and at 37° C. Prime XV was the next best performing medium when hMDMs were thawed at 4° C. (FIG. 2G). We therefore concluded that (i) 10% DMSO is not sufficient to guarantee optimal D5 hMDMs viability, (ii) CS10 is the best performing medium and (iii) Prime XV is the next best alternative, but hMDMs have to be thawed at 4° C. if this medium is used.

As discussed previously, the cryopreservation property can alter the intracellular concentration of salts and pH (21, 22): therefore, when evaluating a novel cryopreservation protocol, it is important to functionally test the cryopreserved cells at the point of thaw. One of the most important functions of macrophages is phagocytosis, a process that involves progressive acidification of intracellular compartments to digest the phagocytic cargo and that in turn shapes the phenotype and function of macrophages during inflammation (27-30). We therefore evaluated the ability of the thawed hMDMs of phagocytosing zymosan-A coated beads. hMDMs cryopreserved with any protocols showed a good phagocytic capacity, with hMDMs frozen in CS10 and Prime-XV performing better than hMDMs frozen in Alb+ 10% DMSO (FIGS. 2H-F). Finally, we evaluated hMDMs viability post-phagocytosis. hMDMs frozen in CS10 showed the best post-phagocytosis viability, especially when thawed at 4° C. (FIG. 2J). We therefore concluded that thawing at 4° C. makes hMDMs more resilient to demanding tasks. The drop in viability compared to the pre-phagocytosis condition is normally observed in this assay, during which hMDMs are read at room temperature using a flow cytometer over the span of few hours.

We further validated our choice to use a progressive temperature increase at thawing by comparing viability and phagocytosis of a sample of hMDMs cryopreserved for three months (FIG. 3A). The analysis of viability at the point of thaw confirmed that thawing with a progressive increase of temperature is the most efficient method (40% viability when thawing at 37° C. vs 80% viability when thawing at 4° C., then at 37° C.) (FIG. 3B). Phagocytosis was similar for hMDMs thawed with or without progressive increase in temperature (FIG. 3C).

hMDMs are cultured in TexMACS medium supplemented with 100 ng/mL of GMP-graded recombinant human MSCF (rhMCSF, also known as CSF1). The use of rhMCSF in the medium at thawing could or not be a key aspect of the protocol. Therefore, in order to define the best minimal conditions to cryopreserve hMDMs, we compared preparations from three distinct donors: half of each preparation was thawed with the usual protocol in the presence or in the absence of rhMCSF in the thawing medium (FIG. 3D). No difference was observed when viability post-thaw was analysed (FIG. 3E). It is possible that the presence of rhMCSF helps hMDMs during thawing when they have been frozen for longer periods of time. We tested the effects of rhMCSF in the thawing medium in hMDMs cryopreserved for 3 months. We are also aware that other cell types are frozen in 66% DMSO in some cell therapy protocols currently tested in clinical trials. Therefore, we compared the effect of 100% CS10 vs. 66% CS10 on yield and viability at the point of thawing (FIG. 3F). Yield was similar for hMDMs cryopreserved in 100% and 66% CS10 (FIG. 3G). Viability was slightly better for hMDMs cryopreserved in 100% CS10 vs. hMDMs cryopreserved in 66%. The effect of rhMCSF was unclear, for some donors improving, for some donors worsening viability (FIG. 3H).

We have therefore established that the ideal protocol to cryopreserve hMDMs entails cooling down hMDMs prior to freezing for 60 minutes, using CS10 or Prime-XV as freezing medium, and a concentration of $20 \times 10^6$ or higher. The ideal thawing process entails a progressive increase in temperature, and a rest time for hMDMs of at least 2 h in incubator at 37° C. prior to use. The use of rhMCSF in the thawing medium (TexMACS) is dispensable but may be used in some cases (e.g. thawing hMDMs after three or more months of cryopreservation).

The next step has been to validate the protocol for long time freezing (five to six months) (FIG. 4A). We analysed yield and viability of a prep of D5 and D7 hMDMs from a single donor cryopreserved for 5 months. Yield and viability were excellent both for D5 and D7 hMDMs (above 60% viability for both, FIGS. 4B-C). We also tested D5 and D7 hMDMs from a single donor which have been cryopreserved for 6 months. Yield was good both for D5 and D7 hMDMs. However, a drop below the 60% mark was noticed for the D5 hMDMs (FIGS. 4D-E). We also measure the phagocytic capacity of hMDMs D5 and D7 after 6 months of cryopreservation. Both D5 and D7 hMDMs were able to perform phagocytosis, with D5 hMDMs performing better than D7 hMDMs (21% vs. 14%) (FIG. 4F).

Macrophages polarise to distinct phenotypes depending on the cytokines cues they receive (31-35). Murine polarised macrophages have been used in several models of disease (2, 6, 36-39). Here we sought to prove that our cryopreservation protocol works for human GMP-graded polarised hMDMs. To this end, we produced alternatively activated macrophages (AAMs) by stimulating D5 hMDMs with a combination of IL4 and IL13 for 24 h. We then froze them using CS10 at three increasing concentrations ($10 \times 10^6$/mL, $20 \times 10^6$/mL, $50 \times 10^6$/mL) (FIG. 4G). Yield at $10 \times 106$/mL is poor (around 20%), although viability reaches the 60% threshold. Much better yield and viability are achieved using a freezing concentration of $20 \times 10^6$/mL and $50 \times 10^6$/mL (FIG. 4H-I). We analysed the phagocytic capacity of AAMs from three distinct donors frozen at a concentration of $20 \times 10^6$/mL; AAMs with all three donors were able to phagocytose, albeit at different levels depending on the donor (FIG. 4J). We therefore concluded that our protocol can be utilised to cryopreserve polarised hMDMs, and that polarised macrophages have a preference for higher concentrations at the point of freezing.

We reasoned that the present cryopreservation protocol will be first used to cryopreserve unpolarised macrophages from cirrhotic patients to perform autologous cell therapy in the future stages of our clinical trial ((19) and clinical trial number ISRCTN 10368050). Hence, we proceeded to validate our cryopreservation protocol on D7 hMDMs from cirrhotic patients that exit the production line for quality control. We took D7 hMDMs from two patients (M2 and M3) and we froze them in 100% CS10 at increasing concentration ($10 \times 10^6$/mL, $20 \times 10^6$/mL, $50 \times 10^6$/mL) and we tested yield, viability and phagocytosis at the point of thaw after two weeks of cryopreservation. We also froze D7 hMDMs from patients M3 in 66% CS10 and we compared yield, viability and phagocytosis at the point of thaw with D7 hMDMs from the same patient frozen in 100% CS10 (FIG. 5A). Patient M2 showed a drop of yield and viability at a freezing concentration of $20 \times 10^6$/m L. The best yield and viability were achieved when a freezing concentration of $50 \times 10^6$/mL was used (FIGS. 5B-C). Phagocytosis was progressively more efficient moving from a freezing concentration of $10 \times 10^6$/mL to $50 \times 10^6$/mL (FIG. 5D). Conversely, D7 hMDMs from patients M3 showed a peak yield of almost 80% when a freezing concentration of $20 \times 10^6$/mL was used (FIG. 5E). Viability at the point of thawing progressively increased with the increase of the freezing concentration and peaked at $50 \times 106$/mL (FIG. 5F). Phagocytosis at thawing was similar for $20 \times 10^6$/mL and $50 \times 10^6$/mL concentrations, and slightly higher for $10 \times 10^6$/mL (FIG. 5G). We concluded that hMDMs from cirrhotic patients need higher concentration at the point of freezing to preserve high viability. Yield and phagocytic ability vary, and are possibly more patient-dependent than method-dependent. Using 66% CS10 at the point of freezing increases the yield for D7 hMDMs frozen at a concentration of $50 \times 10^6$/mL, while decreases the yield for the same cells frozen at a concentration of $20 \times 10^6$/mL (FIG. 5H). Viability at the point of thaw was similar for D7 hMDMs frozen in 100% CS10 and 66% CS10 at both $20 \times 10^6$/mL and $50 \times 10^6$/mL (FIG.

5L). Phagocytosis was higher for D7 hMDMs frozen at a concentration of $20\times10^6$/mL in 66% CS10, and similar for all the other conditions tested (FIG. 5J). We concluded that our protocol effectively cryopreserves hMDMs from cirrhotic patients, both when using 100% and 66% CS10, and a high freezing concentration.

We further the validation of our protocol by measuring yield, viability and phagocytosis of hMDMs from cirrhotic patients cryopreserved for long period of time (4 months). hMDMs were frozen at $10\times10^6$/mL, $20\times10^6$/mL and $50\times10^6$/mL, and thawed in the presence or in the absence of rhMCSF in the thawing medium (TexMACS). We also compared yield and viability for hMDMs cryopreserved in 100% or 66% CS10 (FIG. 6A). We analysed hMDMs from patient M2 after four months of cryopreservation, and we recorded an excellent yield (nearing 100%) for all the freezing concentrations (FIG. 6B). Satisfactory viability (60%) was reached only for hMDMs frozen at a concentration of $50\times10^6$/mL. The addition of rhMCSF in the thawing medium slightly improved viability for the $10\times10^6$/mL freezing concentration (FIG. 6C). Phagocytosis was similar for all freezing concentrations tested and in line with previously obtained results (FIG. 6D). hMDMs from patient M3 were frozen at a concentration of $20\times10^6$/mL in either 100% or 66% CS10. When thawed after four months the yield was around 60% both when hMDMs were frozen in 100% and 66% CS10 (FIG. 6E). Viability was slightly higher when 66% CS10 was used as freezing medium. The addition of rhMCSF to the thawing medium improved viability, especially when 66% CS10 was used as freezing medium, pushing viability above the 60% target (FIG. 6F). Phagocytosis was similar for hMDMs frozen in 100% and 66% CS10 (FIG. 6F), and addition of rhMCSF to the thawing medium failed to change the hMDMs phagocytic ability either (FIG. 6G).

We therefore concluded that long term cryopreservation of cirrhotic hMDMs is feasible with our protocol. Ideally, a freezing concentration between $10\times10^6$/mL and $50\times10^6$/mL should be used, with a preference for higher concentrations. Freezing can be performed with 100% or 66% CS10, and the addition of rhMCSF in the thawing medium (TexMACS) could be beneficial to increase viability.

Mouse models of liver cirrhosis triggered by reiterative $CCl_4$-induced hepatocyte injury are a useful tool to test the safety and efficacy of cell therapy product. The induction phase of liver cirrhosis commonly last 4 to 12 weeks, depending on the extent of fibrosis desired (40-42). We envisage our cell therapy being used in cases of advanced fibrosis therefore we chose to treat our mice for 12 weeks with $CCl_4$. Testing a cryopreserved macrophage-based cell therapy product requires a xenotransplant of human cell into mice. To avoid rejection, we opted to use immunodeficient mice. However, because these mice lack an appropriate immune response to liver fibrosis, they are unlikely to benefit from the paracrine effect of macrophage cell therapy on the mouse own immune response. In the present experiment, we inject $1\times10^6$ cryopreserved hMDMs at week 9, 10 and 11 of $CCl_4$ treatment. Control mice are injected with an equivalent volume of saline only (vehicle). Mice are culled at week 12 and blood and organs collected for further analysis (FIG. 7A). Histological analysis of the quantity of fibrosis in the liver by PSR staining and quantification revealed an average decrease in fibrosis of 13% in cryopreserved hMDMs treated vs. saline treated mice (FIG. 7B). Sera analysis confirmed a positive effect of the cryopreserved hMDMs cell therapy: Results show a trend towards a decrease in liver enzymes ALT and AST (FIGS. 7C-D)

and, more importantly, a significant reduction in bilirubin circulating levels (FIG. 7E), one of the main factors in monitoring the results of macrophage cell therapy in the clinic (19). No change in circulating GLDH and Albumin was noted (FIGS. 7G-H). Despite the cell therapy being carried out on an immunodeficient background, we were able to detect some signal of an anti-inflammatory activity following the injection of our cryopreserved hMDMs cell therapy: we show herein a decrease in circulating IL6 and an increase in circulating IL10 (FIGS. 7I-J).

In conclusion, we have shown that we have establish a novel protocol to cryopreserve functional hMDMs for cell therapy, we have validated the protocol in cirrhotic patients, and we have shown that the cryopreserved cell therapy product is effective at reducing fibrosis in a mouse model of liver cirrhosis. The protocol entails a cool down time in freezing medium prior to transfer at $-80°$ C. of at least 30 minutes, preferentially up to 60 minutes. The freezing medium of choice should be CS10, either at 100% or lower concentration down to 66%. Alternatively, Prime XV should be considered as DMSO-free freezing medium option. hMDMs prefer to be cryopreserved at high concentrations (from $10\times10^6$ to over $50\times10^6$/mL). Using rhMCSF at the point of thaw delivers mixed result and may be consider when hMDMs are cryopreserved for long period of times ($\geq 3$ months). hMDMs have a preference for being thawed with a progressive increase in temperature: hMDMs should be left at $4°$ C. for at least 1 h prior to be diluted in cell culture medium (TexMACS) and left to recover in incubator ($37°$ C., 5% $CO_2$) for at least another hour. hMDMs are then ready for functional assays (e.g. phagocytosis) and/or for transplant as cell therapy.

Clauses of the Invention:

A. A method of cryopreserving macrophages, the method comprising:
  (a) Placing macrophages in medium;
  (b) Cooling the medium of step (a) to a temperature of between about $2$-$22°$ C. at a cooling rate of $1$-$5°$ C. per minute, and maintaining the cooled medium at a temperature of between about $2$-$22°$ C. for a period of at least 30 minutes; and
  (c) Freezing the medium of step (b).

B. The method according to clause A, wherein the cooled medium is maintained at a temperature of between about $2$-$22°$ C. for a period of between 30 to 120 minutes, preferably for a period of between 30 to 60 minutes.

C. The method of clauses A or B, wherein the medium is cooled to a temperature of between about $2$-$20°$ C., preferably between about $2$-$18°$ C., preferably between about $2$-$16°$ C., preferably between about $2$-$14°$ C., preferably between about $2$-$12°$ C., preferably between about $2$-$10°$ C., preferably between about $2$-$8°$ C., and maintained at the same temperature, preferably the medium is cooled to a temperature of between about $4$-$6°$ C. and maintained at the same temperature.

D. The method of any preceding clause, wherein the cooling rate during cooling of the medium is selected from: $1°$ C., $1.1°$ C., $1.2°$ C., $1.3°$ C., $1.4°$ C., $1.5°$ C., $1.6°$ C., $1.7°$ C., $1.8°$ C., $1.9°$ C., $2°$ C., $2.1°$ C., $2.2°$ C., $2.3°$ C., $2.4°$ C., $2.5°$ C., $2.6°$ C., $2.7°$ C., $2.8°$ C., $2.9°$ C., $3°$ C., $3.1°$ C., $3.2°$ C., $3.3°$ C., $3.4°$ C., $3.5°$ C., $3.6°$ C., $3.7°$ C., $3.8°$ C., $3.9°$ C., $4°$ C., $4.1°$ C., $4.2°$ C., $4.3°$ C., $4.4°$ C., $4.5°$ C., $4.6°$ C., $4.7°$ C., $4.8°$ C., $4.9°$ C., and $5°$ C. per minute.

E. The method of clause D, wherein the cooling rate during cooling of the medium is about $1°$ C. per minute.

F. The method according to any preceding clause, wherein the medium is selected from one or more of: human albumin, PlasmaLyte, TexMACS, DMSO CS10, and PrimeXV.

G. The method according to clause F, wherein the medium is a mixture of CS10 and TexMACS.

H. The method according to clause G, wherein the medium comprises about 66% CS10 and 33% Tex-MACS.

I. The method according to any preceding clause, wherein the macrophages are present in the medium at a cell concentration of between $1\times10^6$-$1\times10^8$/mL.

J. The method according to clause I, wherein the macrophages are present in the medium at a cell concentration of between $2\times10^7$-$5\times10^7$/mL.

K. The method according to any preceding clause wherein the freezing of the medium takes place at a temperature selected from $-70°$ C., $-71°$ C., $-72°$ C., $-73°$ C., $-74°$ C., $-75°$ C., $-76°$ C., $-77°$ C., $-78°$ C., $-79°$ C., $-80°$ C., $-81°$ C., $-82°$ C., $-83°$ C., $-84°$ C., $-85°$ C., $-86°$ C., $-87°$ C., $-88°$ C., $-89°$ C., $-90°$ C., $-91°$ C., $-92°$ C., $-93°$ C., $-94°$ C., $-95°$ C., $-96°$ C., $-97°$ C., $-98°$ C., and $-100°$ C.

L. A method of thawing cryopreserved macrophages, the method comprising:
(a) Warming cryopreserved macrophages to a temperature of between about 4-10° C., and maintaining the macrophages at a temperature of between about 4-10° C. for a first period, wherein the first period is at least 30 minutes;
(b) Diluting the cryopreserved macrophages of step (a) in medium; and
(c) Warming the cryopreserved macrophages of step (b) to a temperature of about 37° C., and maintaining the macrophages at a temperature of about 37° C. for a second period, wherein the second period is at least 30 minutes.

M. The method of clause L, wherein the first and second periods are between 1 to 5 hours.

N. The method of clause M, wherein the first period is about 1 hour.

O. The method of clause M or N, wherein the second period is about 2 hours.

P. The method of any of clauses L-O wherein the warming rate during warming of the medium in step (a) or step (c) is selected from: 1° C., 1.1° C., 1.2° C., 1.3° C., 1.4° C., 1.5° C., 1.6° C., 1.7° C., 1.8° C., 1.9° C., 2° C., 2.1° C., 2.2° C., 2.3° C., 2.4° C., 2.5° C., 2.6° C., 2.7° C., 2.8° C., 2.9° C., 3° C., 3.1° C., 3.2° C., 3.3° C., 3.4° C., 3.5° C., 3.6° C., 3.7° C., 3.8° C., 3.9° C., 4° C., 4.1° C., 4.2° C., 4.3° C., 4.4° C., 4.5° C., 4.6° C., 4.7° C., 4.8° C., 4.9° C., and 5° C. per minute, preferably the warming rate during warming of the medium in step (a) or step (c) is about 1° C. per minute.

Q. The method of clause P, wherein step (a) comprises warming the cryopreserved macrophages to a temperature of between about 4-9° C., preferably between 4-8° C., preferably between 4-7° C., preferably between 4-6° C., and maintaining the macrophages at this temperature.

R. The method according to any of clauses L-Q, wherein the medium for diluting contains MCSF (macrophage colony stimulating factor).

S. The method according to clause R, wherein the MCSF is at a concentration of between 50-150 ng/mL in the medium.

T. The method according to any of clauses L-S, wherein the macrophages are diluted in the medium by a factor of between 2 to 20.

U. The method according to any preceding clause wherein the method is GMP compliant.

V. A method according to any preceding clause, wherein the macrophages are human monocyte derived macrophages (hMDMs).

W. A method comprising the steps of the method of cryopreserving macrophages according to any of clauses A-K, and the steps of the method of thawing macrophages according to any of clauses L-T.

X. Cryopreserved macrophages produced by the method of any one of clauses A-K.

Y. Thawed macrophages produced by the method of any one of clauses L-W.

Z. A cryopreserved therapeutic composition comprising a population of cryopreserved macrophages according to clause X, wherein upon thawing, said macrophages have a viability of at least 60%.

AA. The composition of clause Z, wherein the macrophages are at a concentration of $10\times10^6$-$50\times10^6$/mL, BB. The composition of clause Z or AA, said viability being at least 60% after at least 3 months of cryopreservation, preferably at least 6 months of cryopreservation, preferably at least 1 year of cryopreservation.

CC. The composition of clause Z wherein the cryopreserved macrophages are thawed according to the method of clause L.

DD. Cryopreserved macrophages according to clause X or thawed macrophages according to clause Y, for use as a medicament.

EE. Cryopreserved macrophages according to clause X or thawed macrophages according to clause Y, for use in the treatment of a liver disease.

FF. Cryopreserved or thawed macrophages for use according to clause EE, wherein the liver disease is liver cirrhosis.

REFERENCES

1. T. Suzuki et al., Pulmonary macrophage transplantation therapy. *Nature* 514, 450-454 (2014).
2. M. Bacci et al., Macrophages are alternatively activated in patients with endometriosis and required for growth and vascularization of lesions in a mouse model of disease. *Am J Pathol* 175, 547-556 (2009).
3. A. Capobianco et al., Proangiogenic Tie2(+) macrophages infiltrate human and murine endometriotic lesions and dictate their growth in a mouse model of the disease. *Am J Pathol* 179, 2651-2659 (2011).
4. D. Danon, M. A. Kowatch, G. S. Roth, Promotion of wound repair in old mice by local injection of macrophages. *Proc Natl Acad Sci USA* 86, 2018-2020 (1989).
5. D. Danon et al., Treatment of human ulcers by application of macrophages prepared from a blood unit. *Exp Gerontol* 32, 633-641 (1997).
6. M. Z. Zhang et al., IL-4/IL-13-mediated polarization of renal macrophages/dendritic cells to an M2a phenotype is essential for recovery from acute kidney injury. *Kidney Int* 91, 375-386 (2017).
7. J. K. Moore et al., Phenotypic and functional characterization of macrophages with therapeutic potential generated from human cirrhotic monocytes in a cohort study. *Cytotherapy* 17, 1604-1616 (2015).

8. J. K. Moore et al., Patients with the worst outcomes after paracetamol (acetaminophen)-induced liver failure have an early monocytopenia. *Aliment Pharmacol Ther*, (2016).

9. J. A. Thomas et al., Macrophage therapy for murine liver fibrosis recruits host effector cells improving fibrosis, regeneration, and function. *Hepatology* 53, 2003-2015 (2011).

10. M. S. Hu et al., Delivery of monocyte lineage cells in a biomimetic scaffold enhances tissue repair. *JCI Insight* 2, (2017).

11. L. Arnold et al., Inflammatory monocytes recruited after skeletal muscle injury switch into antiinflammatory macrophages to support myogenesis. *J Exp Med* 204, 1057-1069 (2007).

12. F. W. van der Meulen, M. Reiss, E. A. Stricker, E. van Elven, A. E. von dem Borne, Cryopreservation of human monocytes. *Cryobiology* 18, 337-343 (1981).

13. M. J. ASHWOOD-SMITH, Preservation of mouse bone marrow at −79 degrees C. with dimethyl sulphoxide. *Nature* 190, 1204-1205 (1961).

14. H. E. Broxmeyer, S. Cooper, High-efficiency recovery of immature haematopoietic progenitor cells with extensive proliferative capacity from human cord blood cryopreserved for 10 years. *Clin Exp Immunol* 107 Suppl 1, 45-53 (1997).

15. H. E. Broxmeyer et al., High-efficiency recovery of functional hematopoietic progenitor and stem cells from human cord blood cryopreserved for 15 years. *Proc Natl Acad Sci USA* 100, 645-650 (2003).

16. M. Mandl, S. Schmitz, C. Weber, M. Hristov, Characterization of the CD14++CD16+ monocyte population in human bone marrow. *PLoS One* 9, e112140 (2014).

17. A. Delforge, E. Ronge-Collard, P. Stryckmans, T. Spiro, M. A. Malarme, Granulocyte-macrophage progenitor cell preservation at 4 degrees C. *Br J Haematol* 53, 49-54 (1983).

18. P. Walbrun et al., Characterization of rat and human Kupffer cells after cryopreservation. *Cryobiology* 54, 164-172 (2007).

19. F. Moroni et al., Safety profile of autologous macrophage therapy for liver cirrhosis. *Nat Med*, (2019).

20. F. C. Pearlman, R. T. Lee, Detection and measurement of total bilirubin in serum, with use of surfactants as solubilizing agents. *Clin Chem* 20, 447-453 (1974).

21. P. Mazur, Freezing of living cells: mechanisms and implications. *Am J Physiol* 247, C125-142 (1984).

22. P. Mazur, K. W. Cole, Influence of cell concentration on the contribution of unfrozen fraction and salt concentration to the survival of slowly frozen human erythrocytes. *Cryobiology* 22, 509-536 (1985).

23. J. K. SHERMAN, DIMETHYL SULFOXIDE AS A PROTECTIVE AGENT DURING FREEZING AND THAWING OF HUMAN SPERMATOZOA. *Proc Soc Exp Biol Med* 117, 261-264 (1964).

24. J. K. Sherman, Low temperature research on spermatozoa and eggs. *Cryobiology* 1, 103-129 (1964).

25. J. K. Sherman, Pretreatment with protective substances as a factor in freeze-thaw survival. *Cryobiology* 1, 298-300 (1965).

26. J. E. LOVELOCK, M. W. BISHOP, Prevention of freezing damage to living cells by dimethyl sulphoxide. *Nature* 183, 1394-1395 (1959).

27. M. R. Elliott, K. S. Ravichandran, Clearance of apoptotic cells: implications in health and disease. *J Cell Biol* 189, 1059-1070 (2010).

28. M. Lucas et al., Requirements for apoptotic cell contact in regulation of macrophage responses. *J Immunol* 177, 4047-4054 (2006).

29. J. Savill, I. Dransfield, C. Gregory, C. Haslett, A blast from the past: clearance of apoptotic cells regulates immune responses. *Nat Rev Immunol* 2, 965-975 (2002).

30. C. N. Serhan, J. Savill, Resolution of inflammation: the beginning programs the end. *Nat Immunol* 6, 1191-1197 (2005).

31. A. Mantovani et al., The chemokine system in diverse forms of macrophage activation and polarization. *Trends Immunol* 25, 677-686 (2004).

32. D. M. Mosser, J. P. Edwards, Exploring the full spectrum of macrophage activation. *Nat Rev Immunol* 8, 958-969 (2008).

33. S. Gordon, A. Pluddennann, Tissue macrophages: heterogeneity and functions. *BMC Biol* 15, 53 (2017).

34. S. Gordon, A. Pluddennann, The Mononuclear Phagocytic System. Generation of Diversity. *Front Immunol* 10, 1893 (2019).

35. W. J. de Villiers, I. P. Fraser, S. Gordon, Cytokine and growth factor regulation of macrophage scavenger receptor expression and function. *Immunol Lett* 43, 73-79 (1994).

36. G. Casella et al., IL4 induces IL6-producing M2 macrophages associated to inhibition of neuroinflammation in vitroand in vivo. *J Neuroinflammation* 13, 139 (2016).

37. L. Bosurgi et al., Transplanted mesoangioblasts require macrophage IL-10 for survival in a mouse model of muscle injury. *J Immunol* 188, 6267-6277 (2012).

38. L. Bosurgi et al., Vessel-associated myogenic precursors control macrophage activation and clearance of apoptotic cells. *Clin Exp Immunol* 179, 62-67 (2015).

39. L. Bosurgi et al., Macrophage function in tissue repair and remodeling requires IL-4 or IL-13 with apoptotic cells. *Science* 356, 1072-1076 (2017).

40. I. Montfort, R. Perez-Tamayo, Collagenase in experimental carbon tetrachloride cirrhosis of the liver. *Am J Pathol* 92, 411-420 (1978).

41. R. Perez Tamayo, Is cirrhosis of the liver experimentally produced by CCl4 and adequate model of human cirrhosis? *Hepatology* 3, 112-120 (1983).

42. J. Shi, K. Aisaki, Y. Ikawa, K. Wake, Evidence of hepatocyte apoptosis in rat liver after the administration of carbon tetrachloride. *Am J Pathol* 153, 515-525 (1998).

EQUIVALENTS

Those skilled in the art will recognise, or be able to ascertain using no more than routine experimentation, equivalents of the specific embodiments described herein. Such equivalents are intended to be encompassed by the following claims. Any combination of the embodiments disclosed in the any plurality of the dependent claims or Examples is contemplated to be within the scope of the disclosure.

INCORPORATION BY REFERENCE

The disclosure of each and every patent, patent application publication, and scientific publication referred to herein is specifically incorporated herein by reference in its entirety, as are the contents of its Figures.

The invention claimed is:

1. A method of improving the viability of macrophages subjected to cryopreservation, wherein said method comprises the following steps during freezing of the macrophages:

(a) bringing the macrophages in a medium to a temperature of 2-12° C., and maintaining this temperature for at least 30 minutes; followed by:

(b) cooling of the macrophages in a medium at a rate of 1 to 5° C. per minute until the macrophages in the medium are frozen.

2. The method according to claim 1, wherein the method comprises thawing the cryopreserved macrophages produced according to claim 1, wherein the cryopreserved macrophages are in a medium, the method comprising:

(c) warming cryopreserved macrophages to a temperature of between about 2-12° C. and maintaining the medium at a temperature of between about 2-12° C. for a period of at least 30 minutes; and (d) warming the cryopreserved macrophages of step (c) at a warming rate of 1-5° C. per minute until a temperature of 35-37° C. is reached.

3. The method of claim 2, further comprising one or more additional steps:

(i) diluting the cryopreserved macrophages of step (a) in medium; and/or (ii) maintaining the macrophages of step (b) at a temperature of about 37° C. for at least 30 minutes.

4. The method of claim 1, wherein the macrophages are isolated macrophages or macrophages produced in vitro.

5. The method of claim 1, wherein the macrophages are present in the medium at a concentration of at least $5 \times 10^6$ cells/mL.

6. The method of claim 1 wherein the macrophages are present in a medium containing a cryoprotectant.

7. The method of claim 3, wherein the medium for diluting contains rhMCSF (recombinant human macrophage colony stimulating factor), optionally at a concentration of between 50-150 ng/mL.

8. The method of claim 1, wherein the method is GMP compliant.

9. The method of claim 1, wherein the macrophages are present in the medium at a concentration of at least $1 \times 10^7$ cells/mL.

10. A population of cryopreserved macrophages produced according to the method of claim 1.

11. A population of thawed macrophages produced according to the method of claim 3.

12. A cryopreserved therapeutic composition comprising a population of cryopreserved macrophages according to claim 11, wherein said macrophages have a viability of at least 60%.

13. The composition of claim 12, wherein said viability is at least 60% after at least 3 months of cryopreservation, at least 6 months of cryopreservation, or at least 1 year of cryopreservation.

14. A cryopreserved therapeutic composition comprising a population of cryopreserved macrophages produced according to the method of claim 1, wherein upon thawing, said macrophages have a viability of at least 60%, wherein the cryopreserved macrophages are thawed according to the method of claim 2.

15. A method of treating a subject with macrophages having a disease in need thereof, comprising administering to the subject an effective amount of a population of thawed macrophages cryopreserved according to claim 11 before administration to the subject.

16. The method of claim 15, wherein the disease is a liver disease.

17. The method of claim 16, wherein the liver disease is liver cirrhosis.

* * * * *